US010307492B2

(12) United States Patent
Pan et al.

(10) Patent No.: US 10,307,492 B2
(45) Date of Patent: Jun. 4, 2019

(54) MODIFIED MGLUR6 PROMOTER AND METHODS OF USE

(71) Applicant: Wayne State University, Detroit, MI (US)

(72) Inventors: Zhuo-Hua Pan, Troy, MI (US); Qi Lu, Detroit, MI (US); Tushar H. Ganjawala, Canton, MI (US); JrGang Cheng, Chapel Hill, NC (US)

(73) Assignee: Wayne State University, Detrot, MI (US)

( * ) Notice: Subject to any disclaimer, the term of this patent is extended or adjusted under 35 U.S.C. 154(b) by 0 days.

(21) Appl. No.: 15/125,066

(22) PCT Filed: Mar. 11, 2015

(86) PCT No.: PCT/US2015/019985
§ 371 (c)(1),
(2) Date: Sep. 9, 2016

(87) PCT Pub. No.: WO2015/138616
PCT Pub. Date: Sep. 17, 2015

(65) Prior Publication Data
US 2017/0021038 A1   Jan. 26, 2017

Related U.S. Application Data

(60) Provisional application No. 61/951,360, filed on Mar. 11, 2014.

(51) Int. Cl.
*A61K 48/00* (2006.01)
*A61K 38/17* (2006.01)
*A61K 9/00* (2006.01)
*C07K 14/705* (2006.01)
*C12N 15/86* (2006.01)
*C12N 15/67* (2006.01)
*C12N 15/85* (2006.01)

(52) U.S. Cl.
CPC ........ *A61K 48/0058* (2013.01); *A61K 9/0048* (2013.01); *A61K 38/1787* (2013.01); *A61K 48/0075* (2013.01); *C07K 14/70571* (2013.01); *C12N 15/67* (2013.01); *C12N 15/85* (2013.01); *C12N 15/86* (2013.01); *C12N 2750/14143* (2013.01); *C12N 2830/008* (2013.01); *C12N 2830/42* (2013.01)

(58) Field of Classification Search
CPC .. A61K 48/005; A61K 38/177; C07K 14/705; C12N 15/86
See application file for complete search history.

(56) References Cited

U.S. PATENT DOCUMENTS 5,872,005 A   2/1999 Wang et al.
8,470,790 B2   6/2013 Pan et al.

2010/0015095 A1* 1/2010 Pan .................. A61K 48/005
424/93.2
2012/0093772 A1   4/2012 Horsager et al.
2013/0005795 A1   1/2013 Bayla et al.

FOREIGN PATENT DOCUMENTS

EP          0815227 A1     1/1998
WO      WO 00/15822 A1     3/2000
WO      WO 00/54813 A2     9/2000
WO    WO 2007/131180 A2   11/2007
WO    WO 2013/134295 A1    9/2013

OTHER PUBLICATIONS

Altschul et al., "Basic Local Alignment Search Tool", J. Mol. Biol. 215, p. 403-410, (1990).
Altschul et al., "Gapped BLAST and PSI-BLAST: a new generation of protein database search programs", Nucleic Acids Research, vol. 25, No. 17, p. 3389-402, (1997).
Bookstein et al. "Promoter deletion and loss of retinoblastoma gene expression in human prostate carcinoma", PNAS, vol. 87, No. 19, p. 7762-7766 (1990).
Cronin, T. et al., "Efficient transduction and optogenetic stimulation of retinal bipolar cells by a synthetic adeno-associated virus capsid and promoter," EMBO Molecular Medicine, vol. 6, No. 9, p. 1175-1190, (2014).
Dalkara, D. et al., "In Vivo-Directed Evolution of a New Adeno-Associated Virus for Therapeutic Outer Retinal Gene Delivery from the Vitreous," Sci. Transl. Med. 5(189):ra76 (2013).
Database accession No. AL627215, "Mouse DNA sequence from clone RP23-292E3 on chromosome" XP002742174, retrieved from NCBI accession No. EMBL: AL627215, Oct. 21, 2001.
Database accession No. AXS83215, Sep. 30, 2010 (Sep. 30, 2010), "Human metabotropic glutamate receptor 6 cis-regulatory element (CRE)", XP002742175, retrieved from EBI accession No. GSN: AXS83215, Sep. 30, 2010.
Database accession No. JB126099, "Sequence 35126 from Patent EP2021499", XP002742176, retrieved from NCBI accession No. EM PAT: JB126099, Apr. 11, 2013.
Doroudchi et al., "Virally delivered Channelrhodopsin-2 Safely and Effectively Restores Visual Function in Multiple Mouse Models of Blindness", Molecular Therapy, vol. 19, No. 7, p. 1220-1229, (2011).
GenBank Accession No. BC041684.1 (Jul. 15, 2006).
GenBank accession No. AB058890 (Mar. 26, 2002).
GenBank accession No. AF385748 (Jan. 8, 2007).
GenBank accession No. AB058891 (Mar. 26, 2002).
GenBank accession No. AF461397(Jan. 8, 2007).
GenBank Accession No. EU285658.1 (Sep. 8, 2009).
GenBank accession No. EF474018 (Apr. 4, 2007).
GenBank accession No. 6693702 (Jan. 15, 2000).
GenBank accession No. BC113558.1 (Jun. 9, 2008).
Kay, C. N. et al., "Targeting Photoreceptors via Intravitreal Delivery Using Novel, Capsid-Mutated AAV Vectors," *PLoS One*, vol. 8, Issue 4, p. e62097 (2013).

(Continued)

*Primary Examiner* — Antonio Galisteo Gonzalez
(74) *Attorney, Agent, or Firm* — Mintz Levin Cohn Ferris Glovsky and Popeo, P.C.

(57) ABSTRACT

The invention provides nucleic acids and nucleic acid expression vectors containing optimized mGluR6 promoters for expression of transgenes in the retina. The compositions and methods of the invention are useful for expression of gene products to preserve, improve, or restore phototransduction or vision.

17 Claims, 6 Drawing Sheets

Specification includes a Sequence Listing.

(56) References Cited

OTHER PUBLICATIONS

McCarty et al., "Self-complementary AAV Vectors; Advances and Applications", *Molecular Therapy*, vol. 16, No. 10, p. 1648-1656, (2008).

McGowen at al. "Characterization of the Mouse Aldose Reductase Gene and Promoter in a Lens Epithelial Cell Line", *Molecular Vision*, 4(2), 8 pages, (1998).

McLaughlin, S.K. et al., "Adeno-Associated Virus General Transduction Vectors: Analysis of Proviral Structures", *Journal of Virology*, vol. 62, No. 6, p. 1963-1973, (1988).

Petrs_Silva, H. et al., "Novel Properties of Tyrosine-mutant AAV2 Vectors in the Mouse Retina," *Molecular Therapy*, vol. 19, No. 2, p. 293-301 (2011).

Vicente, T. et al. "Virus production for clinical gene therapy," *Methods in Molecular Biology*, vol. 542, p. 447-470 (2009).

Pan, Zhuo-Hua, et al. "AAV-mediated expression targeting of retinal rod bipolar cells with an optimized mGluR6 promoter." Investigative Ophthalmology & Visual Science, vol. 55, Issue 13, (2014):2638; 2 pages, ARVO, United States, https://iovs.arvojournals.org/article.aspx?articleid=2268000, accessed on Jan. 4, 2019.

Kim Ds, et al. "A core paired-type and POU homeodomain-containing transcription factor program drives retinal bipolar cell gene expression." J Neurosci. Jul. 30, 2008;28(31):7748-64, Society for Neuroscience, Washington, D.C., United States.

Lagali PS, et al. (2008) "Light-activated channels targeted to ON bipolar cells restore visual function in retinal degeneration." Nat Neurosci. Jun. 2008;11(6):667-75, Nature Research, London, United Kingdom.

Bi et al., "Ectopic expression of a microbial-type rhodopsin restores visual responses in mice with photoreceptor degeneration." Neuron. Apr. 6, 2006;50(1):23-33, Cell Press, United States.

Ueda et al., "The mGluR6 5' upstream transgene sequence directs a cell-specific and developmentally regulated expression in retinal rod and ON-type cone bipolar cells." J Neurosci. May 1, 1997;17(9):3014-23, Society for Neuroscience, Washington, D.C., United States.

\* cited by examiner

SEQUENCE LISTING

```
<160> NUMBER OF SEQ ID NOS: 34

<210> SEQ ID NO 1
<211> LENGTH: 202
<212> TYPE: DNA
<213> ORGANISM: Mus musculus

<400> SEQUENCE: 1
gatctccaga tggctaaact tttaaatcat gaatgaagta gatattacca aattgctttt      60
tcagcatcca tttagataat catgtttttt gcctttaatc tgttaatgta gtgaattaca     120
gaaatacatt tcctaaatca ttacatcccc caaatcgtta atctgctaaa gtacatctct     180
ggctcaaaca agactggttg tg                                              202

<210> SEQ ID NO 2
<211> LENGTH: 198
<212> TYPE: DNA
<213> ORGANISM: Homo sapiens

<400> SEQUENCE: 2
gatccttaga ttatgaaaca tttacaatta tgaatgaata ttagatgtta tcaaatgctt      60
tttctgcatc catttagata atcatgtttt tcctttaatc tgttaatgcg gtgaattaca     120
ttaatagatt tcctaagtca ttaatctgct aaagtgcatt tctgggacaa accagacttg     180
gttatgacat tgtatgta                                                   198

<210> SEQ ID NO 3
<211> LENGTH: 1095
<212> TYPE: DNA
<213> ORGANISM: Mus musculus

<400> SEQUENCE: 3
taaccatgca cgctcgcaca cgatagataa tacatacacc aatatctgaa aagagaaaag      60
gttctagtgg tcaggacaga gaatgaaaac ggcaggaagg caagaaagtt tgagaacgta     120
gggggtgggg tagggagaca ctacgagtgg aataagccac gtttggagaa cgtctaggca     180
gatacagaaa tgcagaacac agagagaccg agaccagagc agcgtcagac cggctgcaag     240
gctcttgtta ggggctttag aaacacctgt gtgctctccc ggaagcctgg tgcagtcaga     300
gaggaagctt gcttcccaga cagagatgac acagtttcac aacctgtcag accaccttgc     360
aggagagact gaaccccagc aaccagaacc acttggctat gcatgtcctt ttctgtttaa     420
```

-continued

| | |
|---|---|
| acctaagtct ctgaagaccg accaggggag tccctggact tctttgttcc tcttctcggg | 480 |
| gtggcgggac tgattgtgta aatctcttat ctccaacttt cactcttatc tgtctcttta | 540 |
| atcggcatat tgaggatgag tggccaagct tattggtgtt gctgggtcag acaatttaaa | 600 |
| ggcagtctag gggagaagca gacccaggga gtcagagagg cagagagaga agagagccct | 660 |
| tcctccactc tcaagctctg gagggggtct ctgccctcac cctcatccct ccccagaatc | 720 |
| cttaaatcct ctagactgta gctctgattt tacagctgtc acagactcgt cctactagcc | 780 |
| agaggttggc tcaggtaagc accactgggg aggtagccta gggtgcgctg gggtgggtcc | 840 |
| agaggaagag ctgcccagaa ctgtggggga aggagcggga ccgaccatca acaggggac | 900 |
| ttttcaggga gaatgagagc aatcctctgg aggcctggga gaggctgctg agttgctggt | 960 |
| gcgcgagtca ccaactttc ctgcgctctc ggtgtccggc cagaatcccg aagtggcagc | 1020 |
| tgagcacggg gtggcagctt cgtccgccgg ctctcaaggc gtcccggtaa cttccttcc | 1080 |
| cgcagtccag gagca | 1095 |

<210> SEQ ID NO 4
<211> LENGTH: 1784
<212> TYPE: DNA
<213> ORGANISM: Homo sapiens

<400> SEQUENCE: 4

| | |
|---|---|
| caagcaggag gctgctgtgt gctgggagct gtcaggctcg tcctgaacag ggaagggccc | 60 |
| atccacctcc caaacccagt ttatgcagtc cttcgcaatg tcaggctcag ggcctggcac | 120 |
| cagccaagct ccccacccctt cccactgtta aaatggatag gagcagggct aggcccagcc | 180 |
| tgttgactct gggcttccac caggagaagt ggttctggca gtagaaacta tcggggcctg | 240 |
| ggagaggcgg gggaagagag aaaggtggca tgtttcttgc ttgctccctc taccagcctt | 300 |
| gtccaaatcc ccgcagccac cctaatccag cctgtctaat ggagcccaag ccggctcagg | 360 |
| ccctcggacg aggagcctgc taatcccgt ggctaggagc tcaccacctg tctccaggac | 420 |
| gcccttgct ctcttggcat cagagagcca atcctgggc ctcggatggg gggatgataa | 480 |
| aagcatcttt tggccaagcc ccctcacctt ggcctccacg atgagatggg gagttaggtg | 540 |
| cagagagcgt tggcacagtg agcaccgcag ctcgagtggc tgcctcagac ccagagcccg | 600 |
| aggagacttt atacggagcc agaacgaccc cgcggggttc catcctccca agcaataggc | 660 |
| gggagtggga gctgcgagga aagccggccc ctccctcc tccatccaag gcagtgtggg | 720 |
| ctgtttgttt catgccattc tgggtgtgaa tcctgatgcc cacacatgcc agctgcatgc | 780 |
| acttgggcaa ctcaactcac tcctcgaggg ctgtttctcg actgcagggt gttgtaagtt | 840 |
| cgctaatact aaaggcttct ccctcctggc cccttcctgc ccctcgctct tcctcctctt | 900 |
| ccttaggccc tcccagctca ggcagcccct gccccctgca gggttctgca aggagaaagc | 960 |
| tggggaatac cttaggcaac tgcagtcagg agcactggtg gccaggacag agacagagag | 1020 |
| acagaaaagg ggtcagggac agagagagat aaccgcaggg agagacagga agggacagag | 1080 |
| acagaaaaga tttccaagaa gaggacagag gcagaaagcc agggacagag actgagaaac | 1140 |
| agagacctag aggcagaaga agactgagat agagatggac agagattgtg tcagacacag | 1200 |
| ccccagagac agccagacag tctgagtcag acgcaaacca aagacaagaa aacaggaaaa | 1260 |
| cagacccaga gattgggaga gggagggaa ggagatgcgg ggagagccag caccgccacc | 1320 |
| ccccacactc aggagggtc tccacccctcg gagcggtctc tcatccctcc ctagaatcct | 1380 |
| taaatcctct ctcgctcagg gcctcggccg catctgtcac agacttgtcc tgaaccgaca | 1440 |

```
gcggctggcg caggtgactg gcttggggcg ggagcctggg tgtgcgctgg ggatggaccc    1500
cgaggaagag gggccaagct gtcgggaagc ggcagggctg gaggggtgga ggcagtggtc    1560
gggcgggacc ccgggcgaca gggttcggcg cttgtaagag cgagacggag gcccgggcag    1620
gccggctgag ctaactcccc agagccgaag tggaaggcgc cccccgagcg ccttctcccc    1680
aggaccccgg tgtccctccc cgcgccccga gcccgcgctc ccttccccc gccctcagag     1740 cgctccccgc ccctctgtct ccccgcagcc cgctagacga gccg                     1784

<210> SEQ ID NO 5
<211> LENGTH: 500
<212> TYPE: DNA
<213> ORGANISM: Mus musculus

<400> SEQUENCE: 5
ttaaaggcag tctaggggag aagcagaccc agggagtcag agaggcagag agagaagaga     60
gcccttcctc cactctcaag ctctggaggg ggtctctgcc ctcaccctca tccctcccca    120
gaatccttaa atcctctaga ctgtagctct gattttacag ctgtcacaga ctcgtcctac    180
tagccagagg ttggctcagg taagcaccac tggggaggta gcctagggtg cgctggggtg    240
ggtccagagg aagagctgcc cagaactgtg ggggaaggag cgggaccgac catcaacagg    300 gggactttc agggagaatg agagcaatcc tctggaggcc tggagaggc tgctgagttg      360 ctggtgcgcg agtcaccaac ttttcctgcg ctctcggtgt ccggccagaa tcccgaagtg    420
gcagctgagc acgggtggc agcttcgtcc gccggctctc aaggcgtccc ggtaacttcc     480
tttcccgcag tccaggagca                                                500

<210> SEQ ID NO 6
<211> LENGTH: 547
<212> TYPE: DNA
<213> ORGANISM: Homo sapiens

<400> SEQUENCE: 6
ccaaagacaa gaaaacagga aaacagaccc agagattggg agaggagggg gaaggagatg     60
cggggagagc cagcaccgcc accccccaca ctcaggaggg gtctccaccc tcggagcggt    120
ctctcatccc tccctagaat ccttaaatcc tctctcgctc agggcctcgg ccgcatctgt    180
cacagacttg tcctgaaccg acagcggctg gcgcaggtga ctggcttggg gcgggagcct    240
gggtgtgcgc tggggatgga ccccgaggaa gaggggccaa gctgtcggga agcggcaggg    300 ctggagggt ggaggcagtg gtcgggcggg accccgggcg acagggttcg gcgcttgtaa     360
gagcgagacg gaggcccggg caggccggct gagctaactc cccagagccg aagtggaagg    420
cgcgccccga gcgccttctc ccaggaccc cggtgtccct ccccgcgccc cgagcccgcg     480
ctctccttcc ccgccctca gagcgctccc cgcccctctg tctccccgca gcccgctaga    540
cgagccg                                                              547

<210> SEQ ID NO 7
<211> LENGTH: 690
<212> TYPE: DNA
<213> ORGANISM: Mus musculus

<400> SEQUENCE: 7
ggtgagtccc ccaccccact catcctccct gatgcttcct gtgtgggatg ctcatttcca     60
catttgtctc ggagtcccac atgctgagta actctgagat ttgcttaaa atgccatgca    120
```

```
ggtaatttaa atgggaaggt ctgatccaag tgatgaagtg cagccttgat agcatgcttc    180
ctccgccctc ccacaggctt ccatcttttg tggggtgccc acctccacac cttttctttt    240
agctagagtg gtcaagtgga caagctggtc attagcaatc aaggcgtttc agatctggaa    300
gtgggtggtg ccattatgga tcagtgagcc ctgtattttt tgtgcctctg cacaaggtgg    360
gtagtgaagc cctgtccatt acataaccat ggcatcccct agccatgaca taaagggcag    420
tgaaaaattc tttaaggatg ccagagctgc ttttccatt tgtgtgtatg cgtgcaggtg     480
tgtgttgtac atgacacaag tgtatgtgtg tgcatgtgga ggcctgaggt tgatttcagg    540
aatcatcctc aattctttt ctaccttatt cactgaggca gggtctgtgg agagatcacc     600
gatatggcta ctgtgggatt ccctgtctc tgccttcaga gccactcctg atacacagt      660 acacctggct cagatggtca ccaccctcct                                     690

<210> SEQ ID NO 8
<211> LENGTH: 807
<212> TYPE: DNA
<213> ORGANISM: Homo sapiens

<400> SEQUENCE: 8
tcccccaccc cacacgtctc cccagcaccc cctcttgggg atgctcattt tctgcatctg     60
tgtaattggt gccataatcc agatcccttc tcagatcccc agatcctatg agtccgatca    120
tctgtggacg cgtccctcca agcagcgctt gactgggatg gcgtgcgagg aaagcacgct    180
gacggggagg aattgttggg ttttggttt tgtttcttaa tttagtgcct gtatttctag     240
aaaccaagga tacggaatat accatcctgg tgatcagagt gatgaggcag gaacagatgg    300
ctcactttac ataggattg ctcattttcc ccaagttgat gacatccttc agggctattt     360
tatgaaacac attaggggga tatataccat cacgcctggt gcaggtggca gcctggactg    420
agagtagttt tagcgataaa ggcatctcat cacaagacag gaggtctgag agttggtgac    480
tttaggcatg gggcagtgag tgtgtggttg ccttgggtct tcctgcatag tcacaagatg    540
gctgctgagg ctccacccat tacatcttca cagcagcatc ctaacaggaa agagaggctc    600
tgagtttgca tcagcatgta agtgccacc aatcagaact tggtcacctg gccacgccta    660
gctcacctgg ctcacctggc cacgcctaac tcacctggcc actcctagct cacctggcca    720
tgcctagttc acctgccac tcctagctca cctggccact cctagctgaa agtgagcaag    780
tggcagaaac acaccctccc ccttctt                                        807

<210> SEQ ID NO 9
<211> LENGTH: 807
<212> TYPE: DNA
<213> ORGANISM: Mus musculus

<400> SEQUENCE: 9
actccaggcc atgagcaact cctcacatct ccctaagccc ttcctgtcgc cctctggagt     60
cttttgttct gggaatgaga caggcttgac tggctgaagg ttctccgggc ctggcctggg    120
aaacacagga aaacacgact attttttattg ttcattgtgg gagagagaac tggtaggcaa    180
acccaagagc agaaaatgta ccgtgaggga cactgcccca gtaaacctg aaacctacat     240 tatcctaagc cagccaaggt tcttttccag cctgggaagt tgagcgtgac attggtggct    300
gaatttgtag acagaatggc ttctgagtgc ccctgacatt ccccaaaagg aggctctctg    360
cattaatcca tttgtcttta ttataataaa atatccaagt cagggcgttt tttaaggaaa    420
agacttattt ttaacatcaa ctcttggagg tgaaagttca ggcagcgtga caccagctct    480
```

-continued

```
gctgaggacc tagcttgcat cacattttga caaatgttat ggaaagaggg agtagagaag      540
gaaagagtgc atggagagaa ggaacatcag aaagaagagg acagggttc actctttgat      600 agctattcac cttcacagaa ttacctcacc cttccagagg tcaagagcaa catccccagt      660
gacccaataa ccttgcacta agccacacct ctttttttatt ttttatgaga cagggcctca    720
ctctgtatcc ctgaacttgc tatgtggacc aagctgtcct cttgagtgct gggattaaag    780
gcattcagta tcagggctgg tttataa                                          807
```

<210> SEQ ID NO 10
<211> LENGTH: 673
<212> TYPE: DNA
<213> ORGANISM: Homo sapiens

<400> SEQUENCE: 10

```
gggacagtgg cacaatcacc gggcccctgg ggctctccct gagggtccca cccctcctct      60
tgcacatcgc caccttacac actctccctg cctcccttc cctgctccc cgcaccccc       120 accttccctg ctgctgcctc tgagtctggt gcccaggctc agaagcagcc tggtctgggg    180
agatgccaca agcccagact gaatagcgca cagaacatgt gtctgtgttt acagctcctg    240
ggggtgcggg gagggacctg tggcagaac ctagtgcaga aaatgagctg tgagggaagg    300
agcccagggt ccatacagag gctgcggacc ccagcccgag acccaccggc ccgagttcat    360
ctccagccta ggaggctggg tgtgacgctg gtggaggcat gtggggaggg gctggcttcg    420
aactggattt tcccccaagg agtccctctg aaccccctga acagtgggtt acagtgggca    480
gagcaagtgg gcaggcctag ggtcagagga aagcccaggg aaggtgccct aaatgcccc    540 ggccccgttt ttcctgagaa acaaggatct ggtgagtgat tatagagcag ggagatggga   600
tagagtggga agggatgggg gccgagctgg aggaggctcc caggccctcc ctcacccag    660 ccctgctcct acc                                                        673
```

<210> SEQ ID NO 11
<211> LENGTH: 712
<212> TYPE: PRT
<213> ORGANISM: Chlamydomonas reinhardtii

<400> SEQUENCE: 11

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140
```

```
Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Met Glu Val Glu
                325                 330                 335

Thr Met Val His Glu Glu Asp Asp Glu Thr Gln Lys Val Pro Thr Ala
            340                 345                 350

Lys Tyr Ala Asn Arg Asp Ser Phe Ile Ile Met Arg Asp Arg Leu Lys
            355                 360                 365

Glu Lys Gly Phe Glu Thr Arg Ala Ser Leu Asp Gly Asp Pro Asn Gly
        370                 375                 380

Asp Ala Glu Ala Asn Ala Ala Gly Gly Lys Pro Gly Met Glu Met
385                 390                 395                 400

Gly Lys Met Thr Gly Met Gly Met Gly Met Ala Gly Met Gly Met
                405                 410                 415

Ala Thr Ile Asp Ser Gly Arg Val Ile Leu Ala Val Pro Asp Ile Ser
            420                 425                 430

Met Val Asp Phe Phe Arg Glu Gln Phe Ala Arg Leu Pro Val Pro Tyr
        435                 440                 445

Glu Leu Val Pro Ala Leu Gly Ala Glu Asn Thr Leu Gln Leu Val Gln
    450                 455                 460

Gln Ala Gln Ser Leu Gly Gly Cys Asp Phe Val Leu Met His Pro Glu
465                 470                 475                 480

Phe Leu Arg Asp Arg Ser Pro Thr Gly Leu Leu Pro Arg Leu Lys Met
                485                 490                 495

Gly Gly Gln Arg Ala Ala Ala Phe Gly Trp Ala Ala Ile Gly Pro Met
            500                 505                 510

Arg Asp Leu Ile Glu Gly Ser Gly Val Asp Gly Trp Leu Glu Gly Pro
        515                 520                 525

Ser Phe Gly Ala Gly Ile Asn Gln Gln Ala Leu Val Ala Leu Ile Asn
    530                 535                 540

Arg Met Gln Gln Ala Lys Lys Met Gly Met Met Gly Met Gly Met
545                 550                 555                 560
```

```
Gly Met Gly Gly Gly Met Gly Met Gly Met Gly Met
              565             570             575

Ala Pro Ser Met Asn Ala Gly Met Thr Gly Gly Met Gly Gly Ala Ser
            580                 585                 590

Met Gly Gly Ala Val Met Gly Met Gly Met Gly Met Gln Pro Met Gln
        595                 600                 605

Gln Ala Met Pro Ala Met Ser Pro Met Met Thr Gln Gln Pro Ser Met
        610                 615                 620

Met Ser Gln Pro Ser Ala Met Ser Ala Gly Ala Met Gln Ala Met
625                 630                 635                 640

Gly Gly Val Met Pro Ser Pro Ala Pro Gly Gly Arg Val Gly Thr Asn
            645                 650                 655

Pro Leu Phe Gly Ser Ala Pro Ser Pro Leu Ser Ser Gln Pro Gly Ile
            660                 665                 670

Ser Pro Gly Met Ala Thr Pro Ala Ala Thr Ala Ala Pro Ala Ala
            675                 680                 685

Gly Gly Ser Glu Ala Glu Met Leu Gln Gln Leu Met Ser Glu Ile Asn
            690                 695                 700

Arg Leu Lys Asn Glu Leu Gly Glu
705                 710

<210> SEQ ID NO 12
<211> LENGTH: 737
<212> TYPE: PRT
<213> ORGANISM: Chlamydomonas reinhardtii

<400> SEQUENCE: 12

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220
```

-continued

```
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
            340                 345                 350

Arg Ala Ala Met Met Met Met Asn Gly Asn Gly Met Gly Met Gly Met
            355                 360                 365

Gly Met Asn Gly Met Asn Gly Met Gly Gly Met Asn Gly Met Ala Gly
370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415

Gln Phe Ala Gln Leu Ser Val Thr Tyr Glu Leu Val Pro Ala Leu Gly
            420                 425                 430

Ala Asp Asn Thr Leu Ala Leu Val Thr Gln Ala Gln Asn Leu Gly Gly
            435                 440                 445

Val Asp Phe Val Leu Ile His Pro Glu Phe Leu Arg Asp Arg Ser Ser
450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gln Gly Ile Leu
            500                 505                 510

Pro Ala His Ile Val Ala Leu Val Ala Lys Met Gln Gln Met Arg Lys
            515                 520                 525

Met Gln Gln Met Gln Gln Ile Gly Met Met Thr Gly Gly Met Asn Gly
530                 535                 540

Met Gly Gly Gly Met Gly Gly Gly Met Asn Gly Met Gly Gly Gly Asn
545                 550                 555                 560

Gly Met Asn Asn Met Gly Asn Gly Met Gly Gly Gly Met Gly Asn Gly
                565                 570                 575

Met Gly Gly Asn Gly Met Asn Gly Met Gly Gly Gly Asn Gly Met Asn
            580                 585                 590

Asn Met Gly Gly Asn Gly Met Ala Gly Asn Gly Met Gly Gly Gly Met
            595                 600                 605

Gly Gly Asn Gly Met Gly Gly Ser Met Asn Gly Met Ser Ser Gly Val
            610                 615                 620

Val Ala Asn Val Thr Pro Ser Ala Ala Gly Gly Met Gly Gly Met Met
625                 630                 635                 640
```

```
Asn Gly Gly Met Ala Ala Pro Gln Ser Pro Gly Met Asn Gly Gly Arg
                        645                 650                 655

Leu Gly Thr Asn Pro Leu Phe Asn Ala Ala Pro Ser Pro Leu Ser Ser
            660                 665                 670

Gln Leu Gly Ala Glu Ala Gly Met Gly Ser Met Gly Gly Met Gly Gly
        675                 680                 685

Met Ser Gly Met Gly Gly Met Gly Gly Met Gly Gly Met Gly Gly Ala
690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 13
<211> LENGTH: 315
<212> TYPE: PRT
<213> ORGANISM: Chlamydomonas reinhardtii

<400> SEQUENCE: 13

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270
```

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys
305                 310                 315

<210> SEQ ID NO 14
<211> LENGTH: 837
<212> TYPE: PRT
<213> ORGANISM: Volvox carteri

<400> SEQUENCE: 14

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
                20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp Asp Thr Val Lys
    290                 295                 300

Gln Ser Thr Ala Lys Tyr Ala Ser Arg Asp Ser Phe Ile Thr Met Arg
305                 310                 315                 320

Asn Arg Met Arg Glu Lys Gly Leu Glu Val Arg Ala Ser Leu Asp Ala
                325                 330                 335

-continued

Gly Gly Gly Asp Ser Gly Met Glu Ala Gly Gly Gly Ala Ala His
            340                 345                 350

Ala Gln Pro His Met Ala Lys Pro Gly Thr Glu Leu Gly Lys Thr Met
            355                 360                 365

Ser Ala Ser Phe Thr Asn Gly Ala Ala Thr Ser Leu Glu Pro Gly Arg
370                 375                 380

Val Ile Leu Ala Val Pro Asp Ile Ser Met Val Asp Phe Phe Arg Glu
385                 390                 395                 400

Gln Phe Ala Gln Leu Pro Val Pro Tyr Glu Val Pro Ala Leu Gly
                405                 410                 415

Ala Glu Asn Thr Val Gln Leu Val Gln Gln Ala Ala Met Leu Gly Gly
            420                 425                 430

Cys Asp Phe Val Leu Met His Pro Glu Phe Leu Arg Asp Arg Gly Pro
            435                 440                 445

Thr Gly Leu Leu Pro Gln Val Lys Met Met Gly Gln Arg Thr Ala Ala
            450                 455                 460

Phe Gly Trp Ser Gln Met Gly Pro Met Arg Asp Leu Ile Glu Ser Ser
465                 470                 475                 480

Gly Val Gly Ala Trp Leu Glu Gly Pro Ser Phe Gly Ser Gly Ile Ser
                485                 490                 495

Gln Ala Ala Leu Gln Gln Leu Val Val Lys Met Gln Gln Ala Lys Arg
            500                 505                 510

Met Ala Ala Met Gly Ser Met Met Gly Gly Gly Met Gly Asn Gly Met
            515                 520                 525

Gly Met Gly Met Gly Met Gly Met Gly Met Gly Met Gly Asn Gly Met
            530                 535                 540

Gly Asn Gly Met Gly Met Gly Asn Gly Met Gly Asn Gly Met Gly Met
545                 550                 555                 560

Gly Asn Gly Met Gly Asn Gly Met Gly Met Gly Asn Gly Met Gly Met
                565                 570                 575

Gly Asn Gly Met Gly Met Gly Asn Gly Met Gly Met Gly Asn Gly Met
            580                 585                 590

Gly Asn Gly Met Gly Asn Gly Met Gly Met Gly Asn Gly Met Gly Asn
            595                 600                 605

Gly Met Gly Asn Gly Met Gly Asn Gly Met Gly Asn Gly Met Gly Asn
            610                 615                 620

Gly Met Gly Met Gly Asn Gly Met Gly Met Gly Asn Gly Met Gly Asn
625                 630                 635                 640

Gly Met Gly Asn Gly Met Gly Asn Gly Met Gly Asn Gly Met Gly Met
                645                 650                 655

Met Thr Pro Gly Ala Met Gly Met Gly Met Gly Gly Met Gly Asn Leu
            660                 665                 670

Ala Ala Ala Ala Gly Asn Ala Met Tyr Gly Gly Gly Gly Gly Gly
            675                 680                 685

Gly Ser Thr Met Gly Ser Gly Asn Ala Ala Met Met Thr Gly Leu Val
            690                 695                 700

Met Gly Gly Gly Asn Gly Val Gly Ala Gly Pro Gly Gly Val Val Ala
705                 710                 715                 720

Asn Leu Gly Ser Ser Ala Leu Gln Pro Gln Ser Gln Met Met Gly Gly
                725                 730                 735

Gly Asn Val Val Gly Met Ser Ser Pro Gln Leu Gln Leu Gln Gln Ser
            740                 745                 750

```
Ser Ser Met Pro Leu Gly Gly Leu Ala Pro Asn Arg Ile Gly Asn Asn
        755                 760                 765

Pro Leu Phe Gly Ala Ala Pro Ser Pro Leu His Ser Gln Pro Gly Ala
        770                 775                 780

Ser Pro Thr Gly Leu Ser Ser Pro Gln Leu Gly Met Gly Ala Met Leu
785                 790                 795                 800

Pro Ala Gly Thr Ser Val Gly Ala Gly Gly Ser Val Gly Pro Thr
                805                 810                 815

Glu Thr Asp Met Leu Gln Gln Leu Met Thr Glu Ile Asn Arg Leu Lys
                820                 825                 830

Asp Glu Leu Gly Glu
        835

<210> SEQ ID NO 15
<211> LENGTH: 747
<212> TYPE: PRT
<213> ORGANISM: Volvox carteri

<400> SEQUENCE: 15

Met Asp His Pro Val Ala Arg Ser Leu Ile Gly Ser Ser Tyr Thr Asn
1               5                   10                  15

Leu Asn Asn Gly Ser Ile Val Ile Pro Ser Asp Ala Cys Phe Cys Met
                20                  25                  30

Lys Trp Leu Lys Ser Lys Gly Ser Pro Val Ala Leu Lys Met Ala Asn
            35                  40                  45

Ala Leu Gln Trp Ala Ala Phe Ala Leu Ser Val Ile Ile Leu Ile Tyr
        50                  55                  60

Tyr Ala Tyr Ala Thr Trp Arg Thr Thr Cys Gly Trp Glu Glu Val Tyr
65                  70                  75                  80

Val Cys Cys Val Glu Leu Thr Lys Val Val Ile Glu Phe Phe His Glu
                85                  90                  95

Phe Asp Glu Pro Gly Met Leu Tyr Leu Ala Asn Gly Asn Arg Val Leu
                100                 105                 110

Trp Leu Arg Tyr Gly Glu Trp Leu Leu Thr Cys Pro Val Ile Leu Ile
            115                 120                 125

His Leu Ser Asn Leu Thr Gly Leu Lys Asp Asp Tyr Asn Lys Arg Thr
        130                 135                 140

Met Arg Leu Leu Val Ser Asp Val Gly Thr Ile Val Trp Gly Ala Thr
145                 150                 155                 160

Ala Ala Met Ser Thr Gly Tyr Ile Lys Val Ile Phe Phe Leu Leu Gly
                165                 170                 175

Cys Met Tyr Gly Ala Asn Thr Phe Phe His Ala Ala Lys Val Tyr Ile
            180                 185                 190

Glu Ser Tyr His Thr Val Pro Lys Gly Leu Cys Arg Gln Leu Val Arg
        195                 200                 205

Ala Met Ala Trp Leu Phe Phe Val Ser Trp Gly Met Phe Pro Val Leu
210                 215                 220

Phe Leu Leu Gly Pro Glu Gly Phe Gly His Leu Ser Val Tyr Gly Ser
225                 230                 235                 240

Thr Ile Gly His Thr Ile Ile Asp Leu Leu Ser Lys Asn Cys Trp Gly
            245                 250                 255

Leu Leu Gly His Phe Leu Arg Leu Lys Ile His Glu His Ile Leu Leu
        260                 265                 270

Tyr Gly Asp Ile Arg Lys Val Gln Lys Ile Arg Val Ala Gly Glu Glu
        275                 280                 285
```

```
Leu Glu Val Glu Thr Leu Met Thr Glu Glu Ala Pro Asp Thr Val Lys
    290                 295                 300
Lys Ser Thr Ala Gln Tyr Ala Asn Arg Glu Ser Phe Leu Thr Met Arg
305                 310                 315                 320
Asp Lys Leu Lys Glu Lys Gly Phe Glu Val Arg Ala Ser Leu Asp Asn
                325                 330                 335
Ser Gly Ile Asp Ala Val Ile Asn His Asn Asn Asn Tyr Asn Asn Ala
            340                 345                 350
Leu Ala Asn Ala Ala Ala Ala Val Gly Lys Pro Gly Met Glu Leu Ser
        355                 360                 365
Lys Leu Asp His Val Ala Ala Asn Ala Ala Gly Met Gly Gly Ile Ala
    370                 375                 380
Asp His Val Ala Thr Thr Ser Gly Ala Ile Ser Pro Gly Arg Val Ile
385                 390                 395                 400
Leu Ala Val Pro Asp Ile Ser Met Val Asp Tyr Phe Arg Glu Gln Phe
                405                 410                 415
Ala Gln Leu Pro Val Gln Tyr Glu Val Val Pro Ala Leu Gly Ala Asp
            420                 425                 430
Asn Ala Val Gln Leu Val Gln Ala Ala Gly Leu Gly Gly Cys Asp
        435                 440                 445
Phe Val Leu Leu His Pro Glu Phe Leu Arg Asp Lys Ser Ser Thr Ser
    450                 455                 460
Leu Pro Ala Arg Leu Arg Ser Ile Gly Gln Arg Val Ala Ala Phe Gly
465                 470                 475                 480
Trp Ser Pro Val Gly Pro Val Arg Asp Leu Ile Glu Ser Ala Gly Leu
                485                 490                 495
Asp Gly Trp Leu Glu Gly Pro Ser Phe Gly Leu Gly Ile Ser Leu Pro
            500                 505                 510
Asn Leu Ala Ser Leu Val Leu Arg Met Gln His Ala Arg Lys Met Ala
        515                 520                 525
Ala Met Leu Gly Gly Met Gly Gly Met Leu Gly Ser Asn Leu Met Ser
    530                 535                 540
Gly Ser Gly Gly Val Gly Leu Met Gly Ala Gly Ser Pro Gly Gly Gly
545                 550                 555                 560
Gly Gly Ala Met Gly Val Gly Met Thr Gly Met Gly Met Val Gly Thr
                565                 570                 575
Asn Ala Met Gly Arg Gly Ala Val Gly Asn Ser Val Ala Asn Ala Ser
            580                 585                 590
Met Gly Gly Gly Ser Ala Gly Met Gly Met Gly Met Met Gly Met Val
        595                 600                 605
Gly Ala Gly Val Gly Gly Gln Gln Gln Met Gly Ala Asn Gly Met Gly
    610                 615                 620
Pro Thr Ser Phe Gln Leu Gly Ser Asn Pro Leu Tyr Asn Thr Ala Pro
625                 630                 635                 640
Ser Pro Leu Ser Ser Gln Pro Gly Gly Asp Ala Ser Ala Ala Ala Ala
                645                 650                 655
Ala Ala Ala Ala Ala Ala Ala Thr Gly Ala Ala Ser Asn Ser Met Asn
            660                 665                 670
Ala Met Gln Ala Gly Gly Ser Val Arg Asn Ser Gly Ile Leu Ala Gly
        675                 680                 685
Gly Leu Gly Ser Met Met Gly Pro Pro Gly Ala Pro Ala Ala Pro Thr
    690                 695                 700
```

```
Ala Ala Ala Thr Ala Ala Pro Ala Val Thr Met Gly Ala Pro Gly Gly
705                 710                 715                 720

Gly Gly Ala Ala Ala Ser Glu Ala Glu Met Leu Gln Gln Leu Met Ala
            725                 730                 735

Glu Ile Asn Arg Leu Lys Ser Glu Leu Gly Glu
        740                 745
```

<210> SEQ ID NO 16
<211> LENGTH: 291
<212> TYPE: PRT
<213> ORGANISM: Natronomonas pharaonis

<400> SEQUENCE: 16

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290
```

<210> SEQ ID NO 17
<211> LENGTH: 521
<212> TYPE: PRT
<213> ORGANISM: Mus musculus

<400> SEQUENCE: 17

```
Met Asp Ser Pro Ser Gly Pro Arg Val Leu Ser Ser Leu Thr Gln Asp
1               5                   10                  15

Pro Ser Phe Thr Thr Ser Pro Ala Leu Gln Gly Ile Trp Asn Gly Thr
            20                  25                  30

Gln Asn Val Ser Val Arg Ala Gln Leu Leu Ser Val Ser Pro Thr Thr
            35                  40                  45

Ser Ala His Gln Ala Ala Trp Val Pro Phe Pro Thr Val Asp Val
    50                  55                  60

Pro Asp His Ala His Tyr Thr Leu Gly Thr Val Ile Leu Leu Val Gly
65              70                  75                  80

Leu Thr Gly Met Leu Gly Asn Leu Thr Val Ile Tyr Thr Phe Cys Arg
                85                  90                  95

Asn Arg Gly Leu Arg Thr Pro Ala Asn Met Phe Ile Ile Asn Leu Ala
            100                 105                 110

Val Ser Asp Phe Leu Met Ser Val Thr Gln Ala Pro Val Phe Phe Ala
            115                 120                 125

Ser Ser Leu Tyr Lys Lys Trp Leu Phe Gly Glu Thr Gly Cys Glu Phe
130                 135                 140

Tyr Ala Phe Cys Gly Ala Val Phe Gly Ile Thr Ser Met Ile Thr Leu
145                 150                 155                 160

Thr Ala Ile Ala Met Asp Arg Tyr Leu Val Ile Thr Arg Pro Leu Ala
                165                 170                 175

Thr Ile Gly Arg Gly Ser Lys Arg Arg Thr Ala Leu Val Leu Leu Gly
            180                 185                 190

Val Trp Leu Tyr Ala Leu Ala Trp Ser Leu Pro Pro Phe Phe Gly Trp
            195                 200                 205

Ser Ala Tyr Val Pro Glu Gly Leu Leu Thr Ser Cys Ser Trp Asp Tyr
210                 215                 220

Met Thr Phe Thr Pro Gln Val Arg Ala Tyr Thr Met Leu Leu Phe Cys
225                 230                 235                 240

Phe Val Phe Phe Leu Pro Leu Leu Ile Ile Ile Phe Cys Tyr Ile Phe
                245                 250                 255

Ile Phe Arg Ala Ile Arg Glu Thr Gly Arg Ala Cys Glu Gly Cys Gly
            260                 265                 270

Glu Ser Pro Leu Arg Gln Arg Arg Gln Trp Gln Arg Leu Gln Ser Glu
            275                 280                 285

Trp Lys Met Ala Lys Val Ala Leu Ile Val Ile Leu Leu Phe Val Leu
290                 295                 300

Ser Trp Ala Pro Tyr Ser Thr Val Ala Leu Val Ala Phe Ala Gly Tyr
305                 310                 315                 320

Ser His Ile Leu Thr Pro Tyr Met Ser Ser Val Pro Ala Val Ile Ala
                325                 330                 335

Lys Ala Ser Ala Ile His Asn Pro Ile Ile Tyr Ala Ile Thr His Pro
            340                 345                 350

Lys Tyr Arg Val Ala Ile Ala Gln His Leu Pro Cys Leu Gly Val Leu
            355                 360                 365

Leu Gly Val Ser Gly Gln Arg Ser His Pro Ser Leu Ser Tyr Arg Ser
370                 375                 380

Thr His Arg Ser Thr Leu Ser Ser Gln Ser Ser Asp Leu Ser Trp Ile
385                 390                 395                 400

Ser Gly Arg Lys Arg Gln Glu Ser Leu Gly Ser Glu Ser Glu Val Gly
```

```
                    405                 410                 415
Trp Thr Asp Thr Glu Thr Thr Ala Ala Trp Gly Ala Ala Gln Gln Ala
            420                 425                 430

Ser Gly Gln Ser Phe Cys Ser Gln Asn Leu Glu Asp Gly Glu Leu Lys
            435                 440                 445

Ala Ser Ser Pro Gln Val Gln Arg Ser Lys Thr Pro Lys Val Pro
            450                 455                 460

Gly Pro Ser Thr Cys Arg Pro Met Lys Gly Gln Gly Ala Arg Pro Ser
465             470                 475                 480

Ser Leu Arg Gly Asp Gln Lys Gly Arg Leu Ala Val Cys Thr Gly Leu
                485                 490                 495

Ser Glu Cys Pro His Pro His Thr Ser Gln Phe Pro Leu Ala Phe Leu
                500                 505                 510

Glu Asp Asp Val Thr Leu Arg His Leu
                515                 520

<210> SEQ ID NO 18
<211> LENGTH: 478
<212> TYPE: PRT
<213> ORGANISM: Homo sapiens

<400> SEQUENCE: 18

Met Asn Pro Pro Ser Gly Pro Arg Val Leu Pro Ser Pro Thr Gln Glu
1               5                   10                  15

Pro Ser Cys Met Ala Thr Pro Ala Pro Pro Ser Trp Trp Asp Ser Ser
                20                  25                  30

Gln Ser Ser Ile Ser Ser Leu Gly Arg Leu Pro Ser Ile Ser Pro Thr
            35                  40                  45

Ala Pro Gly Thr Trp Ala Ala Trp Val Pro Leu Pro Thr Val Asp
50                  55                  60

Val Pro Asp His Ala His Tyr Thr Leu Gly Thr Val Ile Leu Leu Val
65                  70                  75                  80

Gly Leu Thr Gly Met Leu Gly Asn Leu Thr Val Ile Tyr Thr Phe Cys
                85                  90                  95

Arg Ser Arg Ser Leu Arg Thr Pro Ala Asn Met Phe Ile Ile Asn Leu
                100                 105                 110

Ala Val Ser Asp Phe Leu Met Ser Phe Thr Gln Ala Pro Val Phe Phe
            115                 120                 125

Thr Ser Ser Leu Tyr Lys Gln Trp Leu Phe Gly Glu Thr Gly Cys Glu
130             135                 140

Phe Tyr Ala Phe Cys Gly Ala Leu Phe Gly Ile Ser Ser Met Ile Thr
145                 150                 155                 160

Leu Thr Ala Ile Ala Leu Asp Arg Tyr Leu Val Ile Thr Arg Pro Leu
                165                 170                 175

Ala Thr Phe Gly Val Ala Ser Lys Arg Arg Ala Ala Phe Val Leu Leu
            180                 185                 190

Gly Val Trp Leu Tyr Ala Leu Ala Trp Ser Leu Pro Pro Phe Phe Gly
            195                 200                 205

Trp Ser Ala Tyr Val Pro Glu Gly Leu Leu Thr Ser Cys Ser Trp Asp
            210                 215                 220

Tyr Met Ser Phe Thr Pro Ala Val Arg Ala Tyr Thr Met Leu Leu Cys
225                 230                 235                 240

Cys Phe Val Phe Phe Leu Pro Leu Leu Ile Ile Ile Tyr Cys Tyr Ile
                245                 250                 255
```

```
Phe Ile Phe Arg Ala Ile Arg Glu Thr Gly Arg Ala Leu Gln Thr Phe
                260                 265                 270

Gly Ala Cys Lys Gly Asn Gly Glu Ser Leu Trp Gln Arg Gln Arg Leu
            275                 280                 285

Gln Ser Glu Cys Lys Met Ala Lys Ile Met Leu Leu Val Ile Leu Leu
        290                 295                 300

Phe Val Leu Ser Trp Ala Pro Tyr Ser Ala Val Ala Leu Val Ala Phe
305                 310                 315                 320

Ala Gly Tyr Ala His Val Leu Thr Pro Tyr Met Ser Ser Val Pro Ala
                325                 330                 335

Val Ile Ala Lys Ala Ser Ala Ile His Asn Pro Ile Ile Tyr Ala Ile
                340                 345                 350

Thr His Pro Lys Tyr Arg Val Ala Ile Ala Gln His Leu Pro Cys Leu
            355                 360                 365

Gly Val Leu Leu Gly Val Ser Arg Arg His Ser Arg Pro Tyr Pro Ser
        370                 375                 380

Tyr Arg Ser Thr His Arg Ser Thr Leu Thr Ser His Thr Ser Asn Leu
385                 390                 395                 400

Ser Trp Ile Ser Ile Arg Arg Gln Glu Ser Leu Gly Ser Glu Ser
                405                 410                 415

Glu Val Gly Trp Thr His Met Glu Ala Ala Val Trp Gly Ala Ala
                420                 425                 430

Gln Gln Ala Asn Gly Arg Ser Leu Tyr Gly Gln Gly Leu Glu Asp Leu
            435                 440                 445

Glu Ala Lys Ala Pro Pro Arg Pro Gln Gly His Glu Ala Glu Thr Pro
450                 455                 460

Gly Lys Thr Lys Gly Leu Ile Pro Ser Gln Asp Pro Arg Met
465                 470                 475

<210> SEQ ID NO 19
<211> LENGTH: 514
<212> TYPE: DNA
<213> ORGANISM: Homo sapiens

<400> SEQUENCE: 19
gtcgagagat ctacgggtgg catccctgtg acccctcccc agtgcctctc ctggccctgg      60
aagttgccac tccagtgccc accagccttg tcctaataaa attaagttgc atcattttgt     120
ctgactaggt gtccttctat aatattatgg ggtggagggg ggtggtatgg agcaaggggc     180
aagttgggaa gacaacctgt agggcctgcg gggtctattg gaaccaagc tggagtgcag      240 tggcacaatc ttggctcact gcaatctccg cctcctgggt tcaagcgatt ctcctgcctc     300
agcctcccga gttgttggga ttccaggcat gcatgaccag gctcagctaa ttttttgtttt    360 tttggtagag acggggtttc accatattgg ccaggctggt ctccaactcc taatctcagg    420
tgatctaccc accttggcct cccaaattgc tgggattaca ggcgtgaacc actgctccct    480
tccctgtcct tctgatttg taggtaacca cgtg                                 514

<210> SEQ ID NO 20
<211> LENGTH: 2161
<212> TYPE: DNA
<213> ORGANISM: Artificial Sequence
<220> FEATURE:
<223> OTHER INFORMATION: Mutated capsid protein

<400> SEQUENCE: 20
tcagagagag tgtcctcgag ccaatctgaa acaataccat cggcagccat acctgattta      60
```

```
aatcatttat tgttcaaaga tgcagtcatc caaatccaca ttgaccagat cgcaggcagt    120
gcaagcgtct ggcacctttc ccatgatatg atgaatgtag cacagtttct gatacgcctt    180
tttgacgaca gaaacgggtt gagattctga cacgggaaag cactctaaac agtctttctg    240
tccgtgagtg aagcagatat ttgaattctg attcattctc tcgcattgtc tgcagggaaa    300
cagcatcaga ttcatgccca cgtgacgaga acatttgttt tggtacctgt ctgcgtagtt    360
gatcgaagct tccgcgtctg acgtcgatgg ctgcgcaact gactcgcgca cccgtttggg    420
ctcacttata tctgcgtcac tgggggcggg tctttcttg gctccaccct ttttgacgta    480
gaattcatgc tccacctcaa ccacgtgatc ctttgcccac cggaaaaagt ctttgacttc    540
ctgcttggtg accttcccaa agtcatgatc cagacggcgg gtgagttcaa atttgaacat    600
ccggtcttgc aacggctgct ggtgttcgaa ggtcgttgag ttcccgtcaa tcacggcgca    660
catgttggtg ttggaggtga cgatcacggg agtcgggtct atctgggccg aggacttgca    720
tttctggtcc acgcgcacct tgcttcctcc gagaatggc ttggccgact ccacgacctt    780
ggcggtcatc ttcccctcct cccaccagat caccatcttg tcgacacagt cgttgaaggg    840
aaagttctca ttggtccagt ttacgcaccc gtagaagggc acagtgtggg ctatggcctc    900
cgcgatgttg gtcttcccgg tagttgcagg cccaaacagc cagatggtgt tcctcttgcc    960
gaactttttc gtggcccatc ccagaaagac ggaagccgca tattggggat cgtacccgtt   1020
tagttccaaa attttataaa tccgattgct ggaaatgtcc tccacgggct gctggcccac   1080
caggtagtcg ggggcggttt tagtcaggct cataatcttt cccgcattgt ccaaggcagc   1140
cttgatttgg accgcgagt tggaggccgc attgaaggag atgtatgagg cctggtcctc   1200
ctggatccac tgcttctccg aggtaatccc cttgtccacg agccacccga ccagctccat   1260
gtacctggct gaagttttg atctgatcac cggcgcatca gaattgggat tctgattctc   1320
tttgttctgc tcctgcgtct gcgacacgtg cgtcagatgc tgcgccacca accgtttacg   1380
ctccgtgaga ttcaaacagg cgctgaaaca ataggaaggg agtggatgtc agtgtgtgct   1440
gcccgggggc tctgactaca ggtctccccc ttcgcgcccg atggtgggac ggtatgaata   1500
atccggaata tttataggtt tttttattac aaaactgtta cgaaaacagt aaaatactta   1560
tttatttgcg agatggttat cattttaatt atctccatga tagatctcta tcactgatag   1620
ggagtactta ccttaaatac tgttccatat tagtccacgc ccactggagc tcaggctggg   1680
ttttggggag caagtaattg gggatgtagc actcatccac caccttgttc ccgcctccgg   1740
cgccatttct ggtctttgtg accgcgaacc agtttggcaa agtcggctcg atcccgcggt   1800
aaattctctg aatcagtttt tcgcgaatct gactcaggaa acgtcccaaa accatggatt   1860
tcaccccggt ggtttccacg agcacgtgca tgtggaagta gctctctccc ttctcaaatt   1920
gcacaaagaa aagggcctcc ggggccttac tcacacggcg ccattccgtc agaaagtcgc   1980
gctgcagctt ctcggccacg gtcaggggtg cctgctcaat cagattcaga tccatgtcag   2040
aatctggcgg caactcccat tccttctcgg ccacccagtt cacaaagctg tcagaaatgc   2100
cgggcagatg ctcgtcaagg tcgctgggga ccttaatcac aatctcgtaa aaccccggca   2160
t                                                                  2161
```

<210> SEQ ID NO 21
<211> LENGTH: 6057
<212> TYPE: DNA
<213> ORGANISM: Artificial Sequence
<220> FEATURE:

<223> OTHER INFORMATION: Vector V-032-pFB-AAV-CMV-SV40pA

<400> SEQUENCE: 21

```
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta atcggggc tcccctttagg gttccgattt      180
agtgctttac ggcacctcga ccccaaaaaa cttgattagg gtgatggttc acgtagtggg     240
ccatcgccct gatagacggt ttttcgccct ttgacgttgg agtccacgtt ctttaatagt     300
ggactcttgt tccaaactgg aacaacactc aaccctatct cggtctattc ttttgattta     360
taagggattt tgccgatttc ggcctattgg ttaaaaaatg agctgattta acaaaaattt     420
aacgcgaatt ttaacaaaat attaacgttt acaatttcag gtggcacttt tcggggaaat     480
gtgcgcggaa cccctatttg tttatttttc taaatacatt caaatatgta tccgctcatg     540
agacaataac cctgataaat gcttcaataa tattgaaaaa ggaagagtat gagtattcaa     600
catttccgtg tcgcccttat tcccttttttt gcggcatttt gccttcctgt ttttgctcac     660
ccagaaacgc tggtgaaagt aaaagatgct gaagatcagt tgggtgcacg agtgggttac     720
atcgaactgg atctcaacag cggtaagatc cttgagagtt ttcgccccga agaacgtttt     780
ccaatgatga gcacttttaa agttctgcta tgtggcgcgg tattatcccg tattgacgcc     840
gggcaagagc aactcggtcg ccgcatacac tattctcaga atgacttggt tgagtactca     900
ccagtcacag aaaagcatct tacggatggc atgacagtaa gagaattatg cagtgctgcc     960
ataaccatga gtgataacac tgcggccaac ttacttctga caacgatcgg aggaccgaag    1020
gagctaaccg cttttttgca acatggggga tcatgtaa ctcgccttga tcgttgggaa      1080
ccggagctga atgaagccat accaaacgac gagcgtgaca ccacgatgcc tgtagcaatg    1140
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
caggcaacta tggatgaacg aaatagacag atcgctgaga taggtgcctc actgattaag    1440
cattggtaac tgtcagacca agtttactca tatatacttt agattgattt aaaacttcat    1500
ttttaattta aaaggatcta ggtgaagatc ctttttgata atctcatgac caaaatccct    1560
taacgtgagt tttcgttcca ctgagcgtca gaccccgtag aaaagatcaa aggatcttct    1620
tgagatcctt ttttttctgcg cgtaatctgc tgcttgcaaa caaaaaaacc accgctacca    1680
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacatacctc gctctgctaa tcctgttacc agtggctgct    1860
gccagtggcg ataagtcgtg tcttaccggg ttggactcaa gacgatagtt accggataag    1920
gcgcagcggt cgggctgaac ggggggttcg tgcacacagc ccagcttgga gcgaacgacc    1980
tacaccgaac tgagatacct acagcgtgag cattgagaaa gcgccacgct tcccgaaggg    2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg gggcggagcc tatggaaaaa cgccagcaac    2220
gcggcctttt tacggttcct ggccttttgc tggccttttg ctcacatgtt ctttcctgcg    2280
```

```
ttatccctg attctgtgga taaccgtatt accgcctttg agtgagctga taccgctcgc    2340
cgcagccgaa cgaccgagcg cagcgagtca gtgagcgagg aagcggaaga gcgcctgatg    2400
cggtattttc tccttacgca tctgtgcggt atttcacacc gcagaccagc cgcgtaacct    2460
ggcaaaatcg gttacggttg agtaataaat ggatgccctg cgtaagcggg tgtgggcgga    2520
caataaagtc ttaaactgaa caaaatagat ctaaactatg caataaagt cttaaactag     2580
acagaatagt tgtaaactga atcagtcca gttatgctgt gaaaaagcat actgactttt     2640
tgttatggct aaagcaaact cttcattttc tgaagtgcaa attgcccgtc gtattaaaga    2700
ggggcgtggc caagggcatg gtaaagacta tattcgcggc gttgtgacaa tttaccgaac    2760
aactccgcgg ccgggaagcc gatctcggct tgaacgaatt gttaggtggc ggtacttggg    2820
tcgatatcaa agtgcatcac ttcttcccgt atgcccaact ttgtatagag agccactgcg    2880
ggatcgtcac cgtaatctgc ttgcacgtag atcacataag caccaagcgc gttggcctca    2940
tgcttgagga gattgatgag cgcggtggca atgcccgcc tccggtgctc gccggagact    3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg gcgtaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
cacggatctg ccctggcttc aggagatcgg aagacctcgg ccgtcgcggc gcttgccggt    3780
ggtgctgacc ccggatgaag tggttcgcat cctcggtttt ctggaaggcg agcatcgttt    3840
gttcgcccag gactctagct atagttctag tggttggcta cattattgaa gcatttatca    3900
gggttattgt ctcagagcat gcctgcaggc agctgcgcgc tcgctcgctc actgaggccg    3960
cccgggcgtc gggcgacctt tggtcgcccg gcctcagtga gcgagcgagc gcgcagagag    4020
ggagtggcca actccatcac taggggttcc tgcggccgca cgcgtgttac tagttattaa    4080
tagtaatcaa ttacggggtc attagttcat agcccatata tggagttccg cgttacataa    4140
cttacggtaa atggcccgcc tggctgaccg cccaacgacc cccgcccatt gacgtcaata    4200
atgacgtatg ttcccatagt aacgccaata gggactttcc attgacgtca atgggtggag    4260
tatttacggt aaactgccca cttggcagta catcaagtgt atcatatgcc aagtacgccc    4320
cctattgacg tcaatgacgg taaatggccc gcctggcatt atgcccagta catgacctta    4380
tgggactttc ctacttggca gtacatctac gtattagtca tcgctattac catggtgatg    4440
cggttttggc agtacatcaa tgggcgtgga tagcggtttg actcacgggg atttccaagt    4500
ctccacccca ttgacgtcaa tgggagtttg ttttggcacc aaaatcaacg ggactttcca    4560
aaatgtcgta acaactccgc cccattgacg caaatgggcg gtaggcgtgt acggtgggag    4620
```

```
gtctatataa gcagagctcg tttagtgaac cgtcagatcg cctggagacg ccatccacgc    4680
tgttttgacc tccatagaag acaccgggac cgatccagcc tccaaccggt tcgaacaggt    4740
aagcgcccct aaaatccctt tggcacaatg tgtcctgagg ggagaggcag cgacctgtag    4800
atgggacggg ggcactaacc ctcagggttt ggggttctga atgtgagtat cgccatgtaa    4860
gcccagtatt tggccaatct cagaaagctc ctggctccct ggaggatgga gagagaaaaa    4920
caaacagctc ctggagcagg gagagtgctg gcctcttgct ctccggctcc ctctgttgcc    4980
ctctggtttc tccccaggtt gaattcgata tcggatccat cgataccgtc gacctcgagg    5040
gggggcccgg tacccaattc gccctatagt gagtcgtatt acgcgcgcag cggccgacca    5100
tggcccaact tgtttattgc agcttataat ggttacaaat aaagcaatag catcacaaat    5160
ttcacaaata aagcattttt ttcactgcat tctagttgtg gtttgtccaa actcatcaat    5220
gtatcttatc atgtctggat ctccggacca cgtgcggacc gagcggccgc aggaacccct    5280
agtgatggag ttggccactc cctctctgcg cgctcgctcg ctcactgagg ccgggcgacc    5340
aaaggtcgcc cgacgcccgg gctttgcccg gcggcctca gtgagcgagc gagcgcgcag    5400
ctgcctgcag gaagctgtaa gcttgtcgag aagtactaga ggatcataat cagccatacc    5460
acatttgtag aggttttact tgctttaaaa aacctcccac acctccccct gaacctgaaa    5520
cataaaatga atgcaattgt tgttgttaac ttgtttattg cagcttataa tggttacaaa    5580
taaagcaata gcatcacaaa tttcacaaat aaagcatttt tttcactgca ttctagttgt    5640
ggtttgtcca aactcatcaa tgtatcttat catgtctgga tctgatcact gatatcgcct    5700
aggagatccg aaccagataa gtgaaatcta gttccaaact attttgtcat ttttaatttt    5760
cgtattagct tacgacgcta cacccagttc ccatctattt tgtcactctt ccctaaataa    5820
tccttaaaaa ctccatttcc acccctccca gttcccaact attttgtccg cccacagcgg    5880 ggcattttc ttcctgttat gtttttaatc aaacatcctg ccaactccat gtgacaaacc    5940
gtcatcttcg gctactttt ctctgtcaca gaatgaaaat ttttctgtca tctcttcgtt    6000
attaatgttt gtaattgact gaatatcaac gcttatttgc agcctgaatg gcgaatg      6057
```

<210> SEQ ID NO 22
<211> LENGTH: 10078
<212> TYPE: DNA
<213> ORGANISM: Artificial Sequence
<220> FEATURE:
<223> OTHER INFORMATION: Vector V117-pFB-inCap2-Y444F-inRepOpt-Kan

<400> SEQUENCE: 22

```
ttctctgtca cagaatgaaa attttttctgt catctcttcg ttattaatgt tgtaattga     60 ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcggggc tcccttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt ctttaatagt ggactcttgt tccaaactgg    420
aacaacactc aaccctatct cggtctattc ttttgattta agggattt tgccgatttc    480 ggcctattgg ttaaaaaatg agctgattta acaaaaattt aacgcgaatt ttaacaaaat    540
attaacgttt acaatttcct gatgcggtat tttctcctta cgcatctgtg cggtatttca    600
caccgcatat ggtgcactct cagtacaatc tgctctgatg ccgcatagtt aagccagccc    660
```

```
cgacacccgc caacacccgc tgacgcgccc tgacgggctt gtctgctccc ggcatccgct      720
tacagacaag ctgtgaccgt ctccgggagc tgcatgtgtc agaggttttc accgtcatca      780
ccgaaacgcg cgagacgaaa gggcctcgtg atacgcctat tttataggt taatgtcatg       840 ataataatgg tttcttagac gtcaggtggc acttttcggg gaaatgtgcg cggaacccct     900
atttgtttat ttttctaaat acattcaaat atgtatccgc tcatgagaca ataaccctga      960
taaatgcttc aataatattg aaaaaggaag agtatgattg aacaagatgg attgcacgca     1020
ggttctccgg ccgcttgggt ggagaggcta ttcggctatg actgggcaca acagacaatc     1080
ggctgctctg atgccgccgt gttccggctg tcagcgcagg ggcgcccggt tctttttgtc     1140
aagaccgacc tgtccggtgc cctgaatgaa ctgcaggacg aggcagcgcg gctatcgtgg     1200
ctggccacga cgggcgttcc ttgcgcagct gtgctcgacg ttgtcactga agcgggaagg     1260
gactggctgc tattgggcga agtgccgggg caggatctcc tgtcatctca ccttgctcct     1320
gccgagaaag tatccatcat ggctgatgca atgcggcggc tgcatacgct tgatccggct     1380
acctgcccat tcgaccacca agcgaaacat cgcatcgagc gagcacgtac tcggatggaa     1440
gccggtcttg tcgatcagga tgatctggac gaagagcatc aggggctcgc gccagccgaa     1500
ctgttcgcca ggctcaaggc gcgcatgccc gacggcgagg atctcgtcgt gacccatggc     1560
gatgcctgct tgccgaatat catggtggaa aatggccgct tttctggatt catcgactgt     1620
ggccggctgg gtgtggcgga ccgctatcag gacatagcgt tggctacccg tgatattgct     1680
gaagagcttg gcggcgaatg ggctgaccgc ttcctcgtgc tttacggtat cgccgctccc     1740
gattcgcagc gcatcgcctt ctatcgcctt cttgacgagt tcttctgagt aaccgtcaga     1800
ccaagtttac tcatatatac tttagattga tttaaaactt cattttaat ttaaaaggat      1860 ctaggtgaag atccttttg ataatctcat gaccaaaatc ccttaacgtg agttttcgtt      1920
ccactgagcg tcagaccacg tagaaaagat caaaggatct tcttgagatc cttttttct      1980 gcgcgtaatc tgctgcttgc aaacaaaaaa accaccgcta ccagcggtgg tttgtttgcc     2040
ggatcaagag ctaccaactc tttttccgaa ggtaactggc ttcagcagag cgcagatacc     2100
aaatactgtc cttctagtgt agccgtagtt aggccaccac ttcaagaact ctgtagcacc     2160
gcctacatac ctcgctctgc taatcctgtt accagtggct gctgccagtg gcgataagtc     2220
gtgtcttacc gggttggact caagacgata gttaccggat aaggcgcagc ggtcgggctg     2280
aacggggggt tcgtgcacac agcccagctt ggagcgaacg acctacaccg aactgagata     2340
cctacagcgt gagcattgag aaagcgccac gcttcccgaa gggagaaagg cggacaggta     2400
tccggtaagc ggcagggtcg gaacaggaga gcgcacgagg gagcttccag ggggaaacgc     2460
ctggtatctt tatagtcctg tcgggtttcg ccacctctga cttgagcgtc gatttttgtg     2520
atgctcgtca ggggggcgga gcctatggaa aaacgccagc aacgcggcct ttttacggtt     2580
cctggccttt tgctggcctt ttgctcacat gttctttcct gcgttatccc ctgattctgt     2640
ggataaccgt attaccgcct ttgagtgagc tgataccgct cgccgcagcc gaacgaccga     2700
gcgcagcgag tcagtgagcg aggaagcgga agagcgcctg atgcggtatt ttctccttac     2760
gcatctgtgc ggtatttcac accgcagacc agccgcgtaa cctggcaaaa tcggttacgg     2820
ttgagtaata aatggatgcc ctgcgtaagc gggtgtgggc ggacaataaa gtcttaaact     2880
gaacaaaata gatctaaact atgacaataa agtcttaaac tagacagaat agttgtaaac     2940
tgaaatcagt ccagttatgc tgtgaaaaag catactggac ttttgttatg gctaaagcaa     3000
```

```
actcttcatt ttctgaagtg caaattgccc gtcgtattaa agaggggcgt ggccaagggc    3060
atggtaaaga ctatattcgc ggcgttgtga caatttaccg aacaactccg cggccgggaa    3120
gccgatctcg gcttgaacga attgttaggt ggcggtactt gggtcgatat caaagtgcat    3180
cacttcttcc cgtatgccca actttgtata gagagccact gcgggatcgt caccgtaatc    3240
tgcttgcacg tagatcacat aagcaccaag cgcgttggcc tcatgcttga ggagattgat    3300
gagcgcggtg gcaatgccct gcctccggtg ctcgccggag actgcgagat catagatata    3360
gatctcacta cgcggctgct caaacctggg cagaacgtaa gccgcgagag cgccaacaac    3420
cgcttcttgg tcgaaggcag caagcgcgat gaatgtctta ctacgagcag agttcccgag    3480
gtaatcggag tccggctgat gttgggagta ggtggctacg tctccgaact cacgaccgaa    3540
aagatcaaga gcagcccgca tggatttgac ttggtcaggg ccgagcctac atgtgcgaat    3600
gatgcccata cttgagccac ctaactttgt tttagggcga ctgccctgct gcgtaacatc    3660
gttgctgctg cgtaacatcg ttgctgctcc ataacatcaa acatcgaccc acggcgtaac    3720
gcgcttgctg cttggatgcc cgaggcatag actgtacaaa aaaacagtca taacaagcca    3780
tgaaaaccgc cactgcgccg ttaccaccgc tgcgttcggt caaggttctg gaccagttgc    3840
gtgagcgcat acgctacttg cattacagtt tacgaaccga acaggcttat gtcaactggg    3900
ttcgtgcctt catccgtttc cacggtgtgc gtcacccggc aaccttgggc agcagcgaag    3960
tcgaggcatt tctgtcctgg ctggcgaacg agcgcaaggt tcggtctcc acgcatcgtc    4020
aggcattggc ggccttgctg ttcttctacg gcaaggtgct gtgcacggat ctgccctggc    4080
ttcaggagat cggtagacct cggccgtcgc ggcgcttgcc ggtggtgctg accccggatg    4140
aagtggttcg catcctcggt tttctggaag gcgagcatcg tttgttcgcc caggactcta    4200
gctatagttc tagtggttgg cctacgtacc cgtagtggct atggcagggc ttgccgcccc    4260
gacgttggct gcgagccctg gccttcacc cgaacttggg ggttggggtg gggaaaagga    4320
agaaacgcgg gcgtattggt cccaatgggg tctcggtggg gtatcgacag agtgccagcc    4380
ctgggaccga accccgcgtt tatgaacaaa cgacccaaca cccgtgcgtt ttattctgtc    4440
tttttattgc cgtcatagcg cggggttcctt ccggtattgt ctccttccgt gtttcagtta    4500
gcctccccca tctcccggta ccgcatgctc cttcagagag agtgtcctcg agccaatctg    4560
aaacaatacc atcggcagcc atacctgatt taaatcattt attgttcaaa gatgcagtca    4620
tccaaatcca cattgaccag atcgcaggca gtgcaagcgt ctggcacctt tcccatgata    4680
tgatgaatgt agcacagttt ctgatacgcc ttttttgacga cagaaacggg ttagagattct    4740
gacacgggaa agcactctaa acagtctttc tgtccgtgag tgaagcagat atttgaattc    4800
tgattcattc tctcgcattg tctgcaggga aacagcatca gattcatgcc cacgtgacga    4860
gaacatttgt tttggtacct gtctgcgtag ttgatcgaag cttccgcgtc tgacgtcgat    4920
ggctgcgcaa ctgactcgcg caccgtttg ggctcactta tatctgcgtc actggggcg    4980
ggtcttttct tggctccacc cttttgacg tagaattcat gctccacctc aaccacgtga    5040
tcctttgccc accggaaaaa gtctttgact tcctgcttgg tgaccttccc aaagtcatga    5100
tccagacggc gggtgagttc aaatttgaac atccggtctt gcaacggctg ctggtgttcg    5160
aaggtcgttg agttcccgtc aatcacggcg cacatgttgg tgttggaggt gacgatcacg    5220
ggagtcgggt ctatctgggc cgaggacttg catttctggt ccacgcgcac cttgcttcct    5280
ccgagaatgg ctttggccga ctccacgacc ttggcggtca tcttcccctc ctcccaccag    5340
atcaccatct tgtcgacaca gtcgttgaag ggaaagttct cattggtcca gtttacgcac    5400
```

```
ccgtagaagg gcacagtgtg ggctatggcc tccgcgatgt tggtcttccc ggtagttgca    5460 gcccaaaca gccagatggt gttcctcttg ccgaactttt tcgtggccca tcccagaaag     5520
acggaagccg catattgggg atcgtacccg tttagttcca aaattttata aatccgattg    5580
ctggaaatgt cctccacggg ctgctggccc accaggtagt cggggggcggt tttagtcagg   5640 ctcataatct ttcccgcatt gtccaaggca gccttgattt gggaccgcga gttggaggcc    5700
gcattgaagg agatgtatga ggcctggtcc tcctggatcc actgcttctc cgaggtaatc    5760
cccttgtcca cgagccaccc gaccagctcc atgtacctgg ctgaagtttt tgatctgatc    5820
accggcgcat cagaattggg attctgattc tctttgttct gctcctgcgt ctgcgacacg    5880
tgcgtcagat gctgcgccac caaccgttta cgctccgtga gattcaaaca ggcgctgaaa    5940
caataggaag ggagtggatg tcagtgtgtg ctgcccgggg gctctgacta caggtctccc    6000
ccttcgcgcc cgatggtggg acggtatgaa taatccggaa tatttatagg ttttttttatt  6060 acaaaactgt tacgaaaaca gtaaaatact tatttatttg cgagatggtt atcattttaa    6120
ttatctccat gatagatctc tatcactgat agggagtact taccttaaat actgttccat    6180
attagtccac gcccactgga gctcaggctg gttttgggg agcaagtaat tggggatgta     6240
gcactcatcc accaccttgt tcccgcctcc ggcgccattt ctggtctttg tgaccgcgaa    6300
ccagtttggc aaagtcggct cgatcccgcg gtaaattctc tgaatcagtt tttcgcgaat    6360
ctgactcagg aaacgtccca aaccatgga tttcaccccg gtggtttcca cgagcacgtg     6420
catgtggaag tagctctctc ccttctcaaa ttgcacaaag aaagggcct ccggggcctt     6480 actcacacgg cgccattccg tcagaaagtc gcgctgcagc ttctcggcca cggtcagggg    6540
tgcctgctca atcagattca gatccatgtc agaatctggc ggcaactccc attccttctc    6600
ggccacccag ttcacaaagc tgtcagaaat gccgggcaga tgctcgtcaa ggtcgctggg    6660
gaccttaatc acaatctcgt aaaccccgg catggcgggt agggtgatca agtcttcgtc     6720
gagtgattgt aaataaaatg taatttacag tatagtattt taattaatat acaaatgatt   6780
tgataataat tcttatttaa ctataatata ttgtgttggg ttgaattaaa ggtccgtagc    6840
tttcgaatct aggctcaagc agtgatcaga tccagacatg ataagataca ttgatgagtt    6900
tggacaaacc acaactagaa tgcagtgaaa aaaatgcttt atttgtgaaa tttgtgatgc    6960
tattgcttta tttgtaacca ttataagctg caataaacaa gttaacaaca acaattgcat    7020 tcatttttatg tttcaggttc aggggggaggt gtgggaggtt ttttaaagca agtaaaacct   7080
ctacaaatgt ggtatggctg attatgatcc tctagtactt ctcgacaagc tgtagccatg    7140
gaaactagat aagaaagaaa tacgcagaga ccaaagttca actgaaacga attaaacggt    7200
ttattgatta caagcaatt acagattacg agtcaggtat ctggtgccaa tggggcgagg    7260
ctctgaatac acgccattag tgtccacagt aaagtccaca ttaacagact tgttgtagtt    7320
ggaagtgtac tgaatttcgg gattccgcg tttgctgttt tccttctgca gctcccactc      7380
gatctccacg ctgacctgtc ccgtggagta ctgtgtgatg aaggaagcaa actttgccgc     7440
actgaaggtg gtcgaaggat tcgcaggtac cggggtgttc ttgatgagaa tctgtggagg    7500
agggtgttta agtccgaatc cacccatgag gggagagggg tgaaaatgtc cgtccgtgtg    7560 tggaatctttt gcccagatgg gcccctgaag gtacacatct ctgtcctgcc agaccatgcc   7620
tggaagaacg ccttgtgtgt tgacatctgc ggtagctgct tgtctgttgc ctctctggag   7680
gttggtagat acagaaccat actgctccgt agccacggga ttggttgtcc tgatttcctc   7740
```

```
ttcgtctgta atcatgacct tttcaatgtc cacatttgtt ttctctgagc cttgcttccc    7800
aaagatgaga accccgctct gaggaaaaaa cttttcttca tcgtccttgt ggcttgccat    7860
ggccgggccc ggattcacca gagagtctct gccattgagg tggtacttgg tagctccagt    7920
ccacgagtat tcactgttgt tgttatccgc agatgtcttt gatactcgct gctggcggta    7980
acagggtcca ggaagccagt tcctagactg gtcccgaatg tcactcgctc cggcctgaga    8040
aaactgaagc cttgactgcg tggtggttcc acttggagtg tttgttctgc ttaagaaata    8100
caggtactgg tcgatgagag gattcatgag acggtccaga ctctggctgt gagcgtagct    8160
gctgtggaaa ggaacgtcct caaaagtgta gctgaaggta agttgtttc cggtacgcag     8220
catctgagaa ggaaagtact ccaggcagta aaatgaagag cgtcctactg cctgactccc    8280
gttgttcagg gtgaggtatc catactgtgg caccatgaag acgtctgctg gaacggcgg     8340
gaggcatcct tgatgcgccg agccgaggac gtacgggagc tggtactccg agtcagtaaa    8400
cacctgaacc gtgctggtaa ggttattggc aatcgtcgtc gtaccgtcat tctgcgtgac    8460
ctctttgact tgaatgttaa agagcttgaa gttgagtctc ttgggtcgga atccccagtt    8520
gttgttgatg agtctttgcc agtcacgtgg tgaaaagtgg cagtggaatc tgttgaagtc    8580
aaaatacccc caagggtgc tgtagccaaa gtagtgattg tcgttcgagg ctcctgattg      8640
gctggaaatt tgtttgtaga ggtggttgtt gtaggtgggc agggcccagg ttcgggtgct    8700
ggtggtgatg actctgtcgc ccatccatgt ggaatcgcaa tgccaatttc ccgaggaatt    8760
acccactccg tcggcgccct cgttattgtc tgccattggt gcgccactgc ctgtagccat    8820
cgtattagtt cccagaccag agggggctgc tggtggctgt ccgagaggct gggggtcagg    8880
tactgagtct gcgtctccag tctgaccaaa attcaatctt tttcttgcag gctgctggcc    8940
cgcctttccg gttcccgagg aggagtctgg ctccacagga gagtgctcta ccggcctctt    9000
ttttcccgga gccgtcttaa caggttcctc aaccaggccc agaggttcaa gaaccctctt    9060
tttcgcctgg aagactgctc gtccgaggtt gcccccaaaa gacgtatctt ctttaaggcg    9120
ctcctgaaac tccgcgtcgg cgtggttgta cttgaggtac gggttgtctc cgctgtcgag    9180
ctgccggtcg taggctttgt cgtgctcgag ggccgcggcg tctgcctcgt tgaccggctc    9240
tcccttgtcg agtccgttga agggtccgag gtacttgtac ccaggaagca caagacccct    9300
gctgtcgtcc ttatgccgct ctgcgggctt tggtggtggt gggccaggtt tgagcttcca    9360
ccactgtctt attccttcag agagagtgtc ctcgagccaa tctgaaacaa taggaaggga    9420
gtggatgtca gtgtgtgctg cccgggggct ctgactacag gtctccccct tcgcgcccga    9480
tggtgggacg gtatgaataa tccggaatat ttataggttt ttttattaca aaactgttac    9540
gaaaacagta aaatacttat ttatttgcga gatggttatc attttaatta tctccatgat    9600
agatctctat cactgatagg gagtacttac ctggaagata accatcggca gccatcttaa    9660
caggatccgc gcccgatggt gggacggtat gaataatccg gaatatttat aggtttttt     9720
attacaaaac tgttacgaaa acagtaaaat acttatttat ttgcgagatg ttatcattt     9780
taattatctc catgatctat taatattccg gagtatacct aggagatccg aaccagataa    9840
gtgaaatcta gttccaaact attttgtcat ttttaatttt cgtattagct tacgacgcta    9900
cacccagttc ccatctattt tgtcactctt ccctaaataa tccttaaaaa ctccatttcc    9960
accccctccca gttcccaact attttgtccg cccacagcgg ggcattttc ttcctgttat    10020
gttttaatc aaacatcctg ccaactccat gtgacaaacc gtcatcttcg gctacttt       10078
```

<210> SEQ ID NO 23
<211> LENGTH: 728
<212> TYPE: PRT
<213> ORGANISM: Adeno-associated virus 1

<400> SEQUENCE: 23

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Gly Lys Lys Arg Pro Val
    130                 135                 140

Glu Gln Ser Pro Gln Glu Pro Asp Ser Ser Gly Ile Gly Lys Thr
145                 150                 155                 160

Gly Gln Gln Pro Ala Lys Lys Arg Leu Asn Phe Gly Gln Thr Gly Asp
                165                 170                 175

Ser Glu Ser Val Pro Asp Pro Gln Pro Leu Gly Glu Pro Pro Ala Thr
            180                 185                 190

Pro Ala Ala Val Gly Thr Thr Met Ala Ser Gly Gly Gly Ala Pro Met
        195                 200                 205

Ala Asp Asn Asn Glu Gly Ala Asp Gly Val Gly Asn Ala Ser Gly Asn
    210                 215                 220

Trp His Cys Asp Ser Thr Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Ala Ser Thr Gly Ala Ser Asn Asp Asn His Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Leu Ile Asn Asn Asn Trp Gly Phe Arg
    290                 295                 300

Pro Lys Arg Leu Asn Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
        355                 360                 365

Ile Pro Gln Tyr Gly Tyr Leu Thr Leu Asn Asn Gly Ser Gln Ala Val
    370                 375                 380

Gly Arg Ser Ser Phe Tyr Cys Glu Tyr Phe Pro Ser Gln Met Leu Arg
385                 390                 395                 400

Thr Gly Asn Asn Phe Thr Phe Ser Tyr Thr Phe Glu Glu Val Pro Phe
            405                 410                 415

His Ser Ser Tyr Ala His Ser Gln Ser Leu Asp Arg Leu Met Asn Pro
        420                 425                 430

Leu Ile Asp Gln Tyr Leu Tyr Tyr Leu Asn Arg Thr Gln Asn Gln Ser
    435                 440                 445

Gly Ser Ala Gln Asn Lys Asp Leu Leu Phe Ser Arg Gly Ser Pro Ala
450                 455                 460

Gly Met Ser Val Gln Pro Lys Asn Trp Leu Pro Gly Pro Cys Tyr Arg
465                 470                 475                 480

Gln Gln Arg Val Ser Lys Thr Lys Thr Asn Asn Asn Ser Asn Phe Thr
                485                 490                 495

Trp Thr Gly Ala Ser Lys Tyr Asn Leu Asn Gly Arg Glu Ser Ile Ile
            500                 505                 510

Asn Pro Gly Thr Ala Met Ala Ser His Lys Asp Asp Glu Asp Lys Phe
        515                 520                 525

Phe Pro Met Ser Gly Val Met Ile Phe Gly Lys Glu Ser Ala Gly Ala
    530                 535                 540

Ser Asn Thr Ala Leu Asp Asn Val Met Ile Thr Asp Glu Glu Glu Ile
545                 550                 555                 560

Lys Ala Thr Asn Pro Val Ala Thr Glu Arg Phe Gly Thr Val Ala Val
                565                 570                 575

Asn Phe Gln Ser Ser Thr Asp Pro Ala Thr Gly Asp Val His Ala Met
            580                 585                 590

Gly Ala Leu Pro Gly Met Val Trp Gln Asp Arg Asp Val Tyr Leu Gln
        595                 600                 605

Gly Pro Ile Trp Ala Lys Ile Pro His Thr Asp Gly His Phe His Pro
    610                 615                 620

Ser Pro Leu Met Gly Gly Phe Gly Leu Lys Asn Pro Pro Gln Ile
625                 630                 635                 640

Leu Ile Lys Asn Thr Pro Val Pro Ala Asn Pro Ala Glu Phe Ser
                645                 650                 655

Ala Thr Lys Phe Ala Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
        675                 680                 685

Pro Glu Val Gln Tyr Thr Ser Asn Tyr Ala Lys Ser Ala Asn Val Asp
    690                 695                 700

Phe Thr Val Asp Asn Asn Gly Leu Tyr Thr Glu Pro Arg Pro Ile Gly
705                 710                 715                 720

Thr Arg Tyr Leu Thr Arg Pro Leu
                725

<210> SEQ ID NO 24
<211> LENGTH: 727
<212> TYPE: PRT
<213> ORGANISM: Adeno-associated virus 2

<400> SEQUENCE: 24

Ala Ala Asp Gly Tyr Leu Pro Asp Trp Leu Glu Asp Thr Leu Ser Glu
1               5                   10                  15

Gly Ile Arg Gln Trp Trp Lys Leu Lys Pro Gly Pro Pro Pro Pro Lys
            20                  25                  30

-continued

```
Pro Ala Glu Arg His Lys Asp Asp Ser Arg Gly Leu Val Leu Pro Gly
            35                  40                  45

Tyr Lys Tyr Leu Gly Pro Phe Asn Gly Leu Asp Lys Gly Glu Pro Val
        50                  55                  60

Asn Glu Ala Asp Ala Ala Leu Glu His Asp Lys Ala Tyr Asp Arg
65                  70                  75                  80

Gln Leu Asp Ser Gly Asp Asn Pro Tyr Leu Lys Tyr Asn His Ala Asp
                85                  90                  95

Ala Glu Phe Glu Arg Leu Lys Glu Asp Thr Ser Phe Gly Gly Asn Leu
            100                 105                 110

Gly Arg Ala Val Phe Gln Ala Lys Lys Arg Val Leu Glu Pro Leu Gly
            115                 120                 125

Leu Val Glu Glu Pro Val Lys Thr Ala Pro Gly Lys Lys Arg Pro Val
130                 135                 140

Glu His Ser Pro Val Glu Pro Asp Ser Ser Gly Thr Gly Lys Ala
145                 150                 155                 160

Gly Gln Gln Pro Ala Arg Lys Arg Leu Asn Phe Gly Gln Thr Gly Asp
                165                 170                 175

Ala Asp Ser Val Pro Asp Pro Gln Pro Leu Gly Gln Pro Pro Ala Ala
            180                 185                 190

Pro Ser Gly Leu Gly Asn Thr Met Ala Thr Gly Ser Gly Ala Pro Met
            195                 200                 205

Ala Asp Asn Asn Glu Gly Ala Asp Gly Val Gly Asn Ser Ser Gly Asn
210                 215                 220

Trp His Cys Asp Ser Thr Trp Met Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Gln Ser Gly Ala Ser Asn Asp Asn His Tyr Phe Gly Tyr
            260                 265                 270

Ser Thr Pro Trp Gly Tyr Phe Asp Phe Asn Arg Phe His Cys His Phe
            275                 280                 285

Ser Pro Arg Asp Trp Gln Leu Ile Asn Asn Asn Trp Gly Phe Arg Pro
            290                 295                 300

Lys Arg Leu Asn Phe Lys Leu Phe Asn Ile Gln Val Lys Glu Val Thr
305                 310                 315                 320

Gln Asn Asp Gly Thr Thr Ile Ala Asn Asn Leu Thr Ser Thr Val
                325                 330                 335

Gln Val Phe Thr Asp Ser Glu Tyr Gln Leu Pro Tyr Val Leu Gly Ser
            340                 345                 350

Ala His Gln Gly Cys Leu Pro Pro Phe Pro Ala Asp Val Phe Met Val
            355                 360                 365

Pro Gln Tyr Gly Tyr Leu Thr Leu Asn Asn Gly Ser Gln Ala Val Gly
            370                 375                 380

Arg Ser Ser Phe Tyr Cys Glu Tyr Phe Pro Ser Gln Met Leu Arg Thr
385                 390                 395                 400

Gly Asn Asn Phe Thr Phe Ser Tyr Thr Phe Glu Asp Val Pro Phe His
                405                 410                 415

Ser Ser Tyr Ala His Ser Gln Ser Leu Asp Arg Leu Met Asn Pro Leu
            420                 425                 430

Ile Asp Gln Tyr Leu Tyr Tyr Leu Ser Arg Thr Asn Thr Pro Ser Gly
            435                 440                 445
```

Thr Thr Thr Gln Ser Arg Leu Gln Phe Ser Gln Ala Gly Ala Ser Asp
450                 455                 460

Ile Arg Asp Gln Ser Arg Asn Trp Leu Pro Gly Pro Cys Tyr Arg Gln
465                 470                 475                 480

Gln Arg Val Ser Lys Thr Ser Ala Asn Asn Ser Glu Tyr Ser Trp
                485                 490                 495

Thr Gly Ala Thr Lys Tyr His Leu Asn Gly Arg Asp Ser Leu Val Asn
                500                 505                 510

Pro Gly Pro Ala Met Ala Ser His Lys Asp Asp Glu Lys Phe Phe
                515                 520                 525

Pro Gln Ser Gly Val Leu Ile Phe Gly Lys Gln Gly Ser Glu Lys Thr
530                 535                 540

Asn Val Asp Ile Glu Lys Val Met Ile Thr Asp Glu Glu Glu Ile Arg
545                 550                 555                 560

Thr Thr Asn Pro Val Ala Thr Glu Gln Tyr Gly Ser Val Ser Thr Asn
                565                 570                 575

Leu Gln Arg Asn Arg Gln Ala Ala Thr Ala Asp Val Asn Thr Gln Gly
                580                 585                 590

Val Leu Pro Gly Met Val Trp Gln Asp Arg Asp Val Tyr Leu Gln Gly
                595                 600                 605

Pro Ile Trp Ala Lys Ile Pro His Thr Asp Gly His Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Ser Thr Thr Phe Ser Ala
                645                 650                 655

Ala Lys Phe Ala Ser Phe Ile Thr Gln Tyr Ser Thr Gly Gln Val Ser
                660                 665                 670

Val Glu Ile Glu Trp Glu Gln Lys Glu Asn Ser Lys Arg Trp Asn Pro
675                 680                 685

Glu Ile Gln Tyr Thr Ser Asn Tyr Asn Lys Ser Val Asn Val Asp Phe
                690                 695                 700

Thr Val Asp Thr Asn Gly Val Tyr Ser Glu Pro Arg Pro Ile Gly Thr
705                 710                 715                 720

Arg Tyr Leu Thr Arg Asn Leu
                725

<210> SEQ ID NO 25
<211> LENGTH: 728
<212> TYPE: PRT
<213> ORGANISM: Adeno-associated virus 3

<400> SEQUENCE: 25

Ala Ala Asp Gly Tyr Leu Pro Asp Trp Leu Glu Asp Asn Leu Ser Glu
1               5                   10                  15

Gly Ile Arg Glu Trp Trp Ala Leu Lys Pro Gly Val Pro Gln Pro Lys
                20                  25                  30

Ala Asn Gln Gln His Gln Asp Asn Arg Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Glu Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

```
Ala Glu Phe Glu Arg Leu Gln Glu Asp Thr Ser Phe Gly Gly Asn Leu
            100                 105                 110

Gly Arg Ala Val Phe Gln Ala Lys Lys Arg Ile Leu Glu Pro Leu Gly
        115                 120                 125

Leu Val Glu Glu Ala Ala Lys Thr Ala Pro Gly Lys Lys Gly Ala Val
130                 135                 140

Asp Gln Ser Pro Gln Glu Pro Asp Ser Ser Ser Gly Val Gly Lys Ser
145                 150                 155                 160

Gly Lys Gln Pro Ala Arg Lys Arg Leu Asn Phe Gly Gln Thr Gly Asp
                165                 170                 175

Ser Glu Ser Val Pro Asp Pro Gln Pro Leu Gly Glu Pro Pro Ala Ala
            180                 185                 190

Pro Thr Ser Leu Gly Asn Thr Met Ala Ser Gly Gly Gly Ala Pro Met
        195                 200                 205

Ala Asp Asn Asn Glu Gly Ala Asp Gly Val Gly Asn Ser Ser Gly Asn
    210                 215                 220

Trp His Cys Asp Ser Gln Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Gln Ser Gly Ala Ser Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Leu Ile Asn Asn Asn Trp Gly Phe Arg Pro
    290                 295                 300

Lys Lys Leu Ser Phe Lys Leu Phe Asn Ile Gln Val Arg Gly Val Thr
305                 310                 315                 320

Gln Asn Asp Gly Thr Thr Thr Ile Ala Asn Asn Leu Thr Ser Thr Val
                325                 330                 335

Gln Val Phe Thr Asp Ser Glu Tyr Gln Leu Pro Tyr Val Leu Gly Ser
            340                 345                 350

Ala His Gln Gly Cys Leu Pro Pro Phe Pro Ala Asp Val Phe Met Val
        355                 360                 365

Pro Gln Tyr Gly Tyr Leu Thr Leu Asn Asn Gly Ser Gln Ala Val Gly
    370                 375                 380

Arg Ser Ser Phe Tyr Cys Glu Tyr Phe Pro Ser Gln Met Leu Arg Thr
385                 390                 395                 400

Gly Asn Asn Phe Gln Phe Ser Tyr Thr Phe Glu Asp Val Pro Phe His
                405                 410                 415

Ser Ser Tyr Ala His Ser Gln Ser Leu Asp Arg Leu Met Asn Pro Leu
            420                 425                 430

Ile Asp Gln Tyr Leu Tyr Tyr Leu Asn Arg Thr Gln Gly Thr Thr Ser
        435                 440                 445

Gly Thr Thr Asn Gln Ser Arg Leu Leu Phe Ser Gln Ala Gly Pro Gln
    450                 455                 460

Ser Met Ser Leu Gln Ala Arg Asn Trp Leu Pro Gly Pro Cys Tyr Arg
465                 470                 475                 480

Gln Gln Arg Leu Ser Lys Thr Ala Asn Asn Asn Ser Asn Phe Pro
                485                 490                 495

Trp Thr Ala Ala Ser Lys Tyr His Leu Asn Gly Arg Asp Ser Leu Val
            500                 505                 510
```

-continued

```
Asn Pro Gly Pro Ala Met Ala Ser His Lys Asp Asp Glu Glu Lys Phe
            515                 520                 525

Phe Pro Met His Gly Asn Leu Ile Phe Gly Lys Glu Gly Thr Thr Ala
        530                 535                 540

Ser Asn Ala Glu Leu Asp Asn Val Met Ile Thr Asp Glu Glu Glu Ile
545                 550                 555                 560

Arg Thr Thr Asn Pro Val Ala Thr Glu Gln Tyr Gly Thr Val Ala Asn
                565                 570                 575

Asn Leu Gln Ser Asn Thr Ala Pro Thr Thr Gly Thr Val Asn His Gln
            580                 585                 590

Gly Ala Leu Pro Gly Met Val Trp Gln Asp Arg Asp Val Tyr Leu Gln
        595                 600                 605

Gly Pro Ile Trp Ala Lys Ile Pro His Thr Asp Gly His Phe His Pro
    610                 615                 620

Ser Pro Leu Met Gly Gly Phe Gly Leu Lys His Pro Pro Pro Gln Ile
625                 630                 635                 640

Met Ile Lys Asn Thr Pro Val Pro Ala Asn Pro Pro Thr Thr Phe Ser
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp Asn
        675                 680                 685

Pro Glu Ile Gln Tyr Thr Ser Asn Tyr Asn Lys Ser Val Asn Val Asp
    690                 695                 700

Phe Thr Val Asp Thr Asn Gly Val Tyr Ser Glu Pro Arg Pro Ile Gly
705                 710                 715                 720

Thr Arg Tyr Leu Thr Arg Asn Leu
                725

<210> SEQ ID NO 26
<211> LENGTH: 727
<212> TYPE: PRT
<213> ORGANISM: Adeno-associated virus 4

<400> SEQUENCE: 26

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Arg Leu Gln Gly Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Gln Ala Gly Glu Thr Ala Pro Gly Lys Lys Arg Pro Leu
    130                 135                 140

Ile Glu Ser Pro Gln Gln Pro Asp Ser Ser Thr Gly Ile Gly Lys Lys
145                 150                 155                 160
```

```
Gly Lys Gln Pro Ala Lys Lys Leu Val Phe Asp Glu Thr Gly
                165                 170                 175

Ala Gly Asp Gly Pro Pro Glu Gly Ser Thr Ser Gly Ala Met Ser Asp
            180                 185                 190

Asp Ser Met Arg Ala Ala Ala Gly Gly Ala Ala Val Glu Gly Gly Gln
        195                 200                 205

Gly Ala Asp Gly Val Gly Asn Ala Ser Gly Asp Trp His Cys Asp Ser
    210                 215                 220

Thr Trp Ser Glu Gly His Val Thr Thr Thr Ser Thr Arg Thr Trp Val
225                 230                 235                 240

Leu Pro Thr Tyr Asn Asn His Leu Tyr Lys Arg Leu Gly Glu Ser Leu
                245                 250                 255

Gln Ser Asn Thr Tyr Asn Gly Phe Ser Thr Pro Trp Gly Tyr Phe Asp
            260                 265                 270

Phe Asn Arg Phe His Cys His Phe Ser Pro Arg Asp Trp Gln Leu Ile
        275                 280                 285

Asn Asn Asn Trp Gly Met Arg Pro Lys Ala Met Arg Val Lys Ile Phe
    290                 295                 300

Asn Ile Gln Val Lys Glu Val Thr Thr Ser Asn Gly Glu Thr Thr Val
305                 310                 315                 320

Ala Asn Asn Leu Thr Ser Thr Val Gln Ile Phe Ala Asp Ser Ser Tyr
                325                 330                 335

Glu Leu Pro Tyr Val Met Asp Ala Gly Gln Glu Gly Ser Leu Pro Pro
            340                 345                 350

Phe Pro Asn Asp Val Phe Met Val Pro Gln Tyr Gly Tyr Cys Gly Leu
        355                 360                 365

Val Thr Gly Asn Thr Ser Gln Gln Gln Thr Asp Arg Asn Ala Phe Tyr
    370                 375                 380

Cys Glu Tyr Phe Pro Ser Gln Met Leu Arg Thr Gly Asn Asn Phe Glu
385                 390                 395                 400

Ile Thr Tyr Ser Phe Glu Lys Val Pro Phe His Ser Met Tyr Ala His
                405                 410                 415

Ser Gln Ser Leu Asp Arg Leu Met Asn Pro Leu Ile Asp Gln Tyr Leu
            420                 425                 430

Trp Gly Leu Gln Ser Thr Thr Thr Gly Thr Thr Leu Asn Ala Gly Thr
        435                 440                 445

Ala Thr Thr Asn Phe Thr Lys Leu Arg Pro Thr Asn Phe Ser Asn Phe
    450                 455                 460

Lys Lys Asn Trp Leu Pro Gly Pro Ser Ile Lys Gln Gln Gly Phe Ser
465                 470                 475                 480

Lys Thr Ala Asn Asn Tyr Lys Ile Pro Ala Thr Gly Ser Asp Ser Leu
                485                 490                 495

Ile Lys Tyr Glu Thr His Ser Thr Leu Asp Gly Arg Trp Ser Ala Leu
            500                 505                 510

Thr Pro Gly Pro Pro Met Ala Thr Ala Gly Pro Ala Asp Ser Lys Phe
        515                 520                 525

Ser Asn Ser Gln Leu Ile Phe Ala Gly Pro Lys Gln Asn Gly Asn Thr
    530                 535                 540

Ala Thr Val Pro Gly Thr Leu Ile Phe Thr Ser Glu Glu Glu Leu Ala
545                 550                 555                 560

Ala Thr Asn Ala Thr Asp Thr Asp Met Trp Gly Asn Leu Pro Gly Gly
                565                 570                 575
```

```
Asp Gln Ser Ser Asn Leu Pro Thr Val Asp Arg Leu Thr Ala Leu Gly
                580                 585                 590

Ala Val Pro Gly Met Val Trp Gln Asn Arg Asp Ile Tyr Tyr Gln Gly
            595                 600                 605

Pro Ile Trp Ala Lys Ile Pro His Thr Asp Gly His Phe His Pro Ser
        610                 615                 620

Pro Leu Ile Gly Gly Phe Gly Leu Lys His Pro Pro Gln Ile Phe
625                 630                 635                 640

Ile Lys Asn Thr Pro Val Pro Ala Asn Pro Ala Thr Thr Phe Ser Ser
                645                 650                 655

Thr Pro Val Asn Ser Phe Ile Thr Gln Tyr Ser Thr Gly Gln Val Ser
            660                 665                 670

Val Gln Ile Asp Trp Glu Gln Lys Glu Arg Ser Lys Arg Trp Asn Pro
        675                 680                 685

Glu Val Gln Phe Thr Ser Asn Tyr Gly Gln Gln Asn Ser Leu Leu Trp
    690                 695                 700

Ala Pro Asp Ala Ala Gly Lys Tyr Thr Glu Pro Arg Ala Ile Gly Thr
705                 710                 715                 720

Arg Tyr Leu Thr His His Leu
                725

<210> SEQ ID NO 27
<211> LENGTH: 716
<212> TYPE: PRT
<213> ORGANISM: Adeno-associated virus 5

<400> SEQUENCE: 27

Ser Phe Val Asp His Pro Pro Asp Trp Leu Glu Glu Val Gly Glu Gly
1               5                   10                  15

Leu Arg Glu Phe Leu Gly Leu Glu Ala Gly Pro Pro Lys Pro Lys Pro
            20                  25                  30

Asn Gln Gln His Gln Asp Gln Ala Arg Gly Leu Val Leu Pro Gly Tyr
        35                  40                  45

Asn Tyr Leu Gly Pro Gly Asn Gly Leu Asp Arg Gly Glu Pro Val Asn
    50                  55                  60

Arg Ala Asp Glu Val Ala Arg Glu His Asp Ile Ser Tyr Asn Glu Gln
65                  70                  75                  80

Leu Glu Ala Gly Asp Asn Pro Tyr Leu Lys Tyr Asn His Ala Asp Ala
                85                  90                  95

Glu Phe Glu Lys Leu Ala Asp Asp Thr Ser Phe Gly Gly Asn Leu Gly
            100                 105                 110

Lys Ala Val Phe Gln Ala Lys Lys Arg Val Leu Glu Pro Phe Gly Leu
        115                 120                 125

Val Glu Glu Gly Ala Lys Thr Ala Pro Thr Gly Lys Arg Ile Asp Asp
    130                 135                 140

His Phe Pro Lys Arg Lys Lys Ala Arg Thr Glu Glu Asp Ser Lys Pro
145                 150                 155                 160

Ser Thr Ser Ser Asp Ala Glu Ala Gly Pro Ser Gly Ser Gln Gln Leu
                165                 170                 175

Gln Ile Pro Ala Gln Pro Ala Ser Ser Leu Gly Asp Thr Met Ser Ala
            180                 185                 190

Gly Gly Gly Gly Pro Leu Gly Asp Asn Asn Gln Gly Ala Asp Gly Val
        195                 200                 205

Gly Asn Ala Ser Gly Asp Trp His Cys Asp Ser Thr Trp Met Gly Asp
    210                 215                 220
```

```
Arg Val Val Thr Lys Ser Thr Arg Thr Trp Val Leu Pro Ser Tyr Asn
225                 230                 235                 240

Asn His Gln Tyr Arg Glu Ile Lys Ser Gly Ser Val Asp Gly Ser Asn
                245                 250                 255

Ala Asn Ala Tyr Phe Gly Tyr Ser Thr Pro Trp Gly Tyr Phe Asp Phe
            260                 265                 270

Asn Arg Phe His Ser His Trp Ser Pro Arg Asp Trp Gln Leu Ile Asn
        275                 280                 285

Asn Tyr Trp Gly Phe Arg Pro Arg Ser Leu Arg Val Lys Ile Phe Asn
    290                 295                 300

Ile Gln Val Lys Glu Val Thr Val Gln Asp Ser Thr Thr Thr Ile Ala
305                 310                 315                 320

Asn Asn Leu Thr Ser Thr Val Gln Val Phe Thr Asp Asp Asp Tyr Gln
                325                 330                 335

Leu Pro Tyr Val Val Gly Asn Gly Thr Glu Gly Cys Leu Pro Ala Phe
            340                 345                 350

Pro Pro Gln Val Phe Thr Leu Pro Gln Tyr Gly Tyr Ala Thr Leu Asn
        355                 360                 365

Arg Asp Asn Thr Glu Asn Pro Thr Glu Arg Ser Ser Phe Phe Cys Glu
    370                 375                 380

Tyr Phe Pro Ser Lys Met Leu Arg Thr Gly Asn Asn Phe Glu Phe Thr
385                 390                 395                 400

Tyr Asn Phe Glu Glu Val Pro Phe His Ser Ser Phe Ala Pro Ser Gln
                405                 410                 415

Asn Leu Phe Lys Leu Ala Asn Pro Leu Val Asp Gln Tyr Leu Tyr Arg
            420                 425                 430

Phe Val Ser Thr Asn Asn Thr Gly Gly Val Gln Phe Asn Lys Asn Leu
        435                 440                 445

Ala Gly Arg Tyr Ala Asn Thr Tyr Lys Asn Trp Phe Pro Gly Pro Met
    450                 455                 460

Gly Arg Thr Gln Gly Trp Asn Leu Gly Ser Gly Asn Arg Ala Ser Val
465                 470                 475                 480

Ser Ala Phe Ala Thr Thr Asn Arg Met Glu Leu Glu Gly Ala Ser Tyr
                485                 490                 495

Gln Val Pro Pro Gln Pro Asn Gly Met Thr Asn Asn Leu Gln Gly Ser
            500                 505                 510

Asn Thr Tyr Ala Leu Glu Asn Thr Met Ile Phe Asn Ser Gln Pro Ala
        515                 520                 525

Asn Pro Gly Thr Thr Ala Thr Tyr Leu Glu Gly Asn Met Leu Ile Thr
    530                 535                 540

Ser Glu Ser Glu Thr Gln Pro Val Asn Arg Val Ala Tyr Asn Val Gly
545                 550                 555                 560

Gly Gln Met Ala Thr Asn Asn Gln Ser Thr Thr Ala Pro Ala Thr Gly
                565                 570                 575

Thr Tyr Asn Leu Gln Glu Ile Val Pro Gly Ser Val Trp Met Glu Arg
            580                 585                 590

Asp Val Tyr Leu Gln Gly Pro Ile Trp Ala Lys Ile Pro Glu Thr Gly
        595                 600                 605

Ala His Phe His Pro Ser Pro Ala Met Gly Gly Phe Gly Leu Lys His
    610                 615                 620

Pro Pro Pro Met Met Leu Ile Lys Asn Thr Pro Val Pro Gly Asn Ile
625                 630                 635                 640
```

```
Thr Ser Phe Ser Asp Val Pro Val Ser Ser Phe Ile Thr Gln Tyr Ser
            645                 650                 655

Thr Gly Gln Val Thr Val Glu Met Glu Trp Glu Lys Lys Glu Asn Ser
        660                 665                 670

Lys Arg Trp Asn Pro Glu Ile Gln Tyr Thr Asn Asn Tyr Asn Asp Pro
        675                 680                 685

Gln Phe Val Asp Phe Ala Pro Asp Ser Thr Gly Glu Tyr Arg Thr Thr
        690                 695                 700

Arg Pro Ile Gly Thr Arg Tyr Leu Thr Arg Pro Leu
705                 710                 715

<210> SEQ ID NO 28
<211> LENGTH: 728
<212> TYPE: PRT
<213> ORGANISM: Adeno-associated virus 6

<400> SEQUENCE: 28

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asp Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Phe Gly
        115                 120                 125

Leu Val Glu Glu Gly Ala Lys Thr Ala Pro Gly Lys Lys Arg Pro Val
    130                 135                 140

Glu Gln Ser Pro Gln Glu Pro Asp Ser Ser Ser Gly Ile Gly Lys Thr
145                 150                 155                 160

Gly Gln Gln Pro Ala Lys Lys Arg Leu Asn Phe Gly Gln Thr Gly Asp
                165                 170                 175

Ser Glu Ser Val Pro Asp Pro Gln Pro Leu Gly Glu Pro Pro Ala Thr
            180                 185                 190

Pro Ala Ala Val Gly Thr Thr Met Ala Ser Gly Gly Gly Ala Pro Met
        195                 200                 205

Ala Asp Asn Asn Glu Gly Ala Asp Gly Val Gly Asn Ala Ser Gly Asn
    210                 215                 220

Trp His Cys Asp Ser Thr Trp Leu Gly Asp Arg Val Ile Thr Thr Ser
225                 230                 235                 240

Thr Arg Thr Trp Ala Leu Pro Thr Tyr Asn Asn His Leu Tyr Lys Gln
                245                 250                 255

Ile Ser Ser Ala Ser Thr Gly Ala Ser Asn Asp Asn His Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Leu Ile Asn Asn Asn Trp Gly Phe Arg
    290                 295                 300
```

-continued

```
Pro Lys Arg Leu Asn Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
            325                 330                 335

Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
            355                 360                 365

Ile Pro Gln Tyr Gly Tyr Leu Thr Leu Asn Asn Gly Ser Gln Ala Val
370                 375                 380

Gly Arg Ser Ser Phe Tyr Cys Glu Tyr Phe Pro Ser Gln Met Leu Arg
385                 390                 395                 400

Thr Gly Asn Asn Phe Thr Phe Ser Tyr Thr Phe Glu Asp Val Pro Phe
            405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Asn Arg Thr Gln Asn Gln Ser
            435                 440                 445

Gly Ser Ala Gln Asn Lys Asp Leu Leu Phe Ser Arg Gly Ser Pro Ala
450                 455                 460

Gly Met Ser Val Gln Pro Lys Asn Trp Leu Pro Gly Pro Cys Tyr Arg
465                 470                 475                 480

Gln Gln Arg Val Ser Lys Thr Lys Thr Asn Asn Asn Ser Asn Phe Thr
            485                 490                 495

Trp Thr Gly Ala Ser Lys Tyr Asn Leu Asn Gly Arg Glu Ser Ile Ile
            500                 505                 510

Asn Pro Gly Thr Ala Met Ala Ser His Lys Asp Asp Lys Asp Lys Phe
            515                 520                 525

Phe Pro Met Ser Gly Val Met Ile Phe Gly Lys Glu Ser Ala Gly Ala
530                 535                 540

Ser Asn Thr Ala Leu Asp Asn Val Met Ile Thr Asp Glu Glu Glu Ile
545                 550                 555                 560

Lys Ala Thr Asn Pro Val Ala Thr Glu Arg Phe Gly Thr Val Ala Val
            565                 570                 575

Asn Leu Gln Ser Ser Thr Asp Pro Ala Thr Gly Asp Val His Val Met
            580                 585                 590

Gly Ala Leu Pro Gly Met Val Trp Gln Asp Arg Asp Val Tyr Leu Gln
            595                 600                 605

Gly Pro Ile Trp Ala Lys Ile Pro His Thr Asp Gly His Phe His Pro
            610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Ala Glu Phe Ser
            645                 650                 655

Ala Thr Lys Phe Ala Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
            675                 680                 685

Pro Glu Val Gln Tyr Thr Ser Asn Tyr Ala Lys Ser Ala Asn Val Asp
            690                 695                 700

Phe Thr Val Asp Asn Asn Gly Leu Tyr Thr Glu Pro Arg Pro Ile Gly
705                 710                 715                 720
```

-continued

```
Thr Arg Tyr Leu Thr Arg Pro Leu
            725

<210> SEQ ID NO 29
<211> LENGTH: 729
<212> TYPE: PRT
<213> ORGANISM: Adeno-associated virus 7

<400> SEQUENCE: 29

Ala Ala Asp Gly Tyr Leu Pro Asp Trp Leu Glu Asp Asn Leu Ser Glu
1               5                   10                  15

Gly Ile Arg Glu Trp Trp Asp Leu Lys Pro Gly Ala Pro Lys Pro Lys
            20                  25                  30

Ala Asn Gln Gln Lys Gln Asp Asn Gly Arg Gly Leu Val Leu Pro Gly
        35                  40                  45

Tyr Lys Tyr Leu Gly Pro Phe Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Ala Lys Lys Arg Pro Val
    130                 135                 140

Glu Pro Ser Pro Gln Arg Ser Pro Asp Ser Ser Thr Gly Ile Gly Lys
145                 150                 155                 160

Lys Gly Gln Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro Ala
            180                 185                 190

Ala Pro Ser Ser Val Gly Gly Thr Val Ala Ala Gly Gly Gly Ala Pro
        195                 200                 205

Met Ala Asp Asn Asn Glu Gly Ala Asp Gly Val Gly Asn Ala Ser Gly
    210                 215                 220

Asn Trp His Cys Asp Ser Thr Trp Leu Gly Asp Arg Val Ile Thr Thr
225                 230                 235                 240

Ser Thr Arg Thr Trp Ala Leu Pro Thr Tyr Asn Asn His Leu Tyr Lys
                245                 250                 255

Gln Ile Ser Ser Glu Thr Ala Gly Ser Thr Asn Asp Asn Thr Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Leu Ile Asn Asn Asn Trp Gly Phe
    290                 295                 300

Arg Pro Lys Lys Leu Arg Phe Lys Leu Phe Asn Ile Gln Val Lys Glu
305                 310                 315                 320

Val Thr Thr Asn Asp Gly Val Thr Thr Ile Ala Asn Asn Leu Thr Ser
                325                 330                 335

Thr Ile Gln Val Phe Ser Asp Ser Glu Tyr Gln Leu Pro Tyr Val Leu
            340                 345                 350

Gly Ser Ala His Gln Gly Cys Leu Pro Pro Phe Pro Ala Asp Val Phe
        355                 360                 365
```

Met Ile Pro Gln Tyr Gly Tyr Leu Thr Leu Asn Asn Gly Ser Gln Ser
            370                 375                 380

Val Gly Arg Ser Ser Phe Tyr Cys Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Asn
            435                 440                 445

Pro Gly Gly Thr Ala Gly Asn Arg Glu Leu Gln Phe Tyr Gln Gly Gly
450                 455                 460

Pro Ser Thr Met Ala Glu Gln Ala Lys Asn Trp Leu Pro Gly Pro Cys
465                 470                 475                 480

Phe Arg Gln Gln Arg Val Ser Lys Thr Leu Asp Asn Asn Asn Ser Asn
                485                 490                 495

Phe Ala Trp Thr Gly Ala Thr Lys Tyr His Leu Asn Gly Arg Asn Ser
            500                 505                 510

Leu Val Asn Pro Gly Val Ala Met Ala Thr His Lys Asp Asp Glu Asp
            515                 520                 525

Arg Phe Phe Pro Ser Ser Gly Val Leu Ile Phe Gly Lys Thr Gly Ala
530                 535                 540

Thr Asn Lys Thr Thr Leu Glu Asn Val Leu Met Thr Asn Glu Glu Glu
545                 550                 555                 560

Ile Arg Pro Thr Asn Pro Val Ala Thr Glu Glu Tyr Gly Ile Val Ser
                565                 570                 575

Ser Asn Leu Gln Ala Asn Thr Ala Ala Gln Thr Gln Val Val Asn Asn
            580                 585                 590

Gln Gly Ala Leu Pro Gly Met Val Trp Gln Asn Arg Asp Val Tyr Leu
            595                 600                 605

Gln Gly Pro Ile Trp Ala Lys Ile Pro His Thr Asp Gly Asn Phe His
610                 615                 620

Pro Ser Pro Leu Met Gly Gly Phe Gly Leu Lys His Pro Pro Pro Gln
625                 630                 635                 640

Ile Leu Ile Lys Asn Thr Pro Val Pro Ala Asn Pro Pro Glu Val Phe
                645                 650                 655

Thr Pro Ala Lys Phe Ala Ser Phe Ile Thr Gln Tyr Ser Thr Gly Gln
            660                 665                 670

Val Ser Val Glu Ile Glu Trp Glu Gln Lys Glu Asn Ser Lys Arg Trp
            675                 680                 685

Asn Pro Glu Ile Gln Tyr Thr Ser Asn Phe Glu Lys Gln Thr Gly Val
            690                 695                 700

Asp Phe Ala Val Asp Ser Gln Gly Val Tyr Ser Glu Pro Arg Pro Ile
705                 710                 715                 720

Gly Thr Arg Tyr Leu Thr Arg Asn Leu
                725

<210> SEQ ID NO 30
<211> LENGTH: 730
<212> TYPE: PRT
<213> ORGANISM: Adeno-associated virus 8

<400> SEQUENCE: 30

Ala Ala Asp Gly Tyr Leu Pro Asp Trp Leu Glu Asp Asn Leu Ser Glu

```
            1               5                   10                  15
        Gly Ile Arg Glu Trp Trp Ala Leu Lys Pro Gly Ala Pro Lys Pro Lys
                        20                  25                  30
        Ala Asn Gln Gln Lys Gln Asp Asp Gly Arg Gly Leu Val Leu Pro Gly
                        35                  40                  45
        Tyr Lys Tyr Leu Gly Pro Phe Asn Gly Leu Asp Lys Gly Glu Pro Val
                        50                  55                  60
        Asn Ala Ala Asp Ala Ala Ala Leu Glu His Asp Lys Ala Tyr Asp Gln
        65                      70                  75                  80
        Gln Leu Gln Ala Gly Asp Asn Pro Tyr Leu Arg Tyr Asn His Ala Asp
                            85                  90                  95
        Ala Glu Phe Glu Arg Leu Gln Glu Asp Thr Ser Phe Gly Gly Asn Leu
                        100                 105                 110
        Gly Arg Ala Val Phe Gln Ala Lys Lys Arg Val Leu Glu Pro Leu Gly
                        115                 120                 125
        Leu Val Glu Glu Gly Ala Lys Thr Ala Pro Gly Lys Lys Arg Pro Val
                        130                 135                 140
        Glu Pro Ser Pro Gln Arg Ser Pro Asp Ser Ser Thr Gly Ile Gly Lys
        145                     150                 155                 160
        Lys Gly Gln Gln Pro Ala Arg Lys Arg Leu Asn Phe Gly Gln Thr Gly
                            165                 170                 175
        Asp Ser Glu Ser Val Pro Asp Pro Gln Pro Leu Gly Glu Pro Pro Ala
                        180                 185                 190
        Ala Pro Ser Gly Val Gly Asn Thr Met Ala Ala Gly Gly Gly Ala Pro
                        195                 200                 205
        Met Ala Asp Asn Asn Glu Gly Ala Asp Gly Val Gly Ser Ser Ser Gly
                210                     215                 220
        Asn Trp His Cys Asp Ser Thr Trp Leu Gly Asp Arg Val Ile Thr Thr
        225                     230                 235                 240
        Ser Thr Arg Thr Trp Ala Leu Pro Thr Tyr Asn Asn His Leu Tyr Lys
                            245                 250                 255
        Gln Ile Ser Asn Gly Thr Ser Gly Gly Ala Thr Asn Asp Asn Thr Tyr
                        260                 265                 270
        Phe Gly Tyr Ser Thr Pro Trp Gly Tyr Phe Asp Phe Asn Arg Phe His
                        275                 280                 285
        Cys His Phe Ser Pro Arg Asp Trp Gln Leu Ile Asn Asn Asn Trp Gly
                        290                 295                 300
        Phe Arg Pro Lys Arg Leu Ser Phe Lys Leu Phe Asn Ile Gln Val Lys
        305                     310                 315                 320
        Glu Val Thr Gln Asn Glu Gly Thr Lys Thr Ile Ala Asn Asn Leu Thr
                            325                 330                 335
        Ser Thr Ile Gln Val Phe Thr Asp Ser Glu Tyr Gln Leu Pro Tyr Val
                        340                 345                 350
        Leu Gly Ser Ala His Gln Gly Cys Leu Pro Pro Phe Pro Ala Asp Val
                        355                 360                 365
        Phe Met Ile Pro Gln Tyr Gly Tyr Leu Thr Leu Asn Asn Gly Ser Gln
                        370                 375                 380
        Ala Val Gly Arg Ser Ser Phe Tyr Cys Glu Tyr Phe Pro Ser Gln Met
        385                     390                 395                 400
        Leu Arg Thr Gly Asn Asn Phe Gln Phe Thr Tyr Thr Phe Glu Asp Val
                            405                 410                 415
        Pro Phe His Ser Ser Tyr Ala His Ser Gln Ser Leu Asp Arg Leu Met
                        420                 425                 430
```

Asn Pro Leu Ile Asp Gln Tyr Leu Tyr Tyr Leu Ser Arg Thr Gln Thr
            435                 440                 445
Thr Gly Gly Thr Ala Asn Thr Gln Thr Leu Gly Phe Ser Gln Gly Gly
    450                 455                 460
Pro Asn Thr Met Ala Asn Gln Ala Lys Asn Trp Leu Pro Gly Pro Cys
465                 470                 475                 480
Tyr Arg Gln Gln Arg Val Ser Thr Thr Thr Gly Asn Asn Asn Ser Asn
                485                 490                 495
Phe Ala Trp Thr Ala Gly Thr Lys Tyr His Leu Asn Gly Arg Asn Ser
            500                 505                 510
Leu Ala Asn Pro Gly Ile Ala Met Ala Thr His Lys Asp Asp Glu Glu
            515                 520                 525
Arg Phe Phe Pro Ser Asn Gly Ile Leu Ile Phe Gly Lys Gln Asn Ala
        530                 535                 540
Ala Arg Asp Asn Ala Asp Tyr Ser Asp Val Met Leu Thr Ser Glu Glu
545                 550                 555                 560
Glu Ile Lys Thr Thr Asn Pro Val Ala Thr Glu Tyr Gly Ile Val
                565                 570                 575
Ala Asp Asn Leu Gln Gln Asn Thr Ala Pro Gln Ile Gly Thr Val Asn
            580                 585                 590
Ser Gln Gly Ala Leu Pro Gly Met Val Trp Gln Asn Arg Asp Val Tyr
        595                 600                 605
Leu Gln Gly Pro Ile Trp Ala Lys Ile Pro His Thr Asp Gly Asn Phe
    610                 615                 620
His Pro Ser Pro Leu Met Gly Gly Phe Gly Leu Lys His Pro Pro Pro
625                 630                 635                 640
Gln Ile Leu Ile Lys Asn Thr Pro Val Pro Ala Asp Pro Pro Thr Thr
                645                 650                 655
Phe Asn Gln Ser Lys Leu Asn Ser Phe Ile Thr Gln Tyr Ser Thr Gly
            660                 665                 670
Gln Val Ser Val Glu Ile Glu Trp Glu Gln Lys Glu Asn Ser Lys Arg
        675                 680                 685
Trp Asn Pro Glu Ile Gln Tyr Thr Ser Asn Tyr Tyr Lys Ser Thr Ser
    690                 695                 700
Val Asp Phe Ala Val Asn Thr Glu Gly Val Tyr Ser Glu Pro Arg Pro
705                 710                 715                 720
Ile Gly Thr Arg Tyr Leu Thr Arg Asn Leu
                725                 730

<210> SEQ ID NO 31
<211> LENGTH: 728
<212> TYPE: PRT
<213> ORGANISM: Adeno-associated virus 9

<400> SEQUENCE: 31

Ala Ala Asp Gly Tyr Leu Pro Asp Trp Leu Glu Asp Asn Leu Ser Glu
1               5                   10                  15
Gly Ile Arg Glu Trp Trp Ala Leu Lys Pro Gly Ala Pro Gln Pro Lys
            20                  25                  30
Ala Asn Gln Gln His Gln Asp Asn Ala Arg Gly Leu Val Leu Pro Gly
        35                  40                  45
Tyr Lys Tyr Leu Gly Pro Gly Asn Gly Leu Asp Lys Gly Glu Pro Val
    50                  55                  60
Asn Ala Ala Asp Ala Ala Ala Leu Glu His Asp Lys Ala Tyr Asp Gln

-continued

```
                65                  70                  75                  80
        Gln Leu Lys Ala Gly Asp Asn Pro Tyr Leu Lys Tyr Asn His Ala Asp
                        85                  90                  95
        Ala Glu Phe Glu Arg Leu Lys Glu Asp Thr Ser Phe Gly Gly Asn Leu
                       100                 105                 110
        Gly Arg Ala Val Phe Gln Ala Lys Lys Arg Leu Leu Glu Pro Leu Gly
                       115                 120                 125
        Leu Val Glu Glu Ala Ala Lys Thr Ala Pro Gly Lys Lys Arg Pro Val
               130                 135                 140
        Glu Gln Ser Pro Gln Glu Pro Asp Ser Ser Ala Gly Ile Gly Lys Ser
        145                 150                 155                 160
        Gly Ala Gln Pro Ala Lys Lys Arg Leu Asn Phe Gly Gln Thr Gly Asp
                           165                 170                 175
        Thr Glu Ser Val Pro Asp Pro Gln Pro Ile Gly Glu Pro Ala Ala
                       180                 185                 190
        Pro Ser Gly Val Gly Leu Thr Met Ala Ser Gly Gly Ala Pro Val
                   195                 200                 205
        Ala Asp Asn Asn Glu Gly Ala Asp Gly Val Gly Ser Ser Gly Asn
               210                 215                 220
        Trp His Cys Asp Ser Gln Trp Leu Gly Asp Arg Val Ile Thr Thr Ser
        225                 230                 235                 240
        Thr Arg Thr Trp Ala Leu Pro Thr Tyr Asn Asn His Leu Tyr Lys Gln
                           245                 250                 255
        Ile Ser Asn Ser Thr Ser Gly Gly Ser Ser Asn Asp Asn Ala Tyr Phe
                       260                 265                 270
        Gly Tyr Ser Thr Pro Trp Gly Tyr Phe Asp Phe Asn Arg Phe His Cys
                   275                 280                 285
        His Phe Ser Pro Arg Asp Trp Gln Leu Ile Asn Asn Trp Gly Phe
               290                 295                 300
        Arg Pro Lys Arg Leu Asn Phe Lys Leu Phe Asn Ile Gln Val Lys Glu
        305                 310                 315                 320
        Val Thr Asp Asn Asn Gly Val Lys Thr Ile Ala Asn Asn Leu Thr Ser
                           325                 330                 335
        Thr Val Gln Val Phe Thr Asp Ser Asp Tyr Gln Leu Pro Tyr Val Leu
                       340                 345                 350
        Gly Ser Ala His Glu Gly Cys Leu Pro Pro Phe Pro Ala Asp Val Phe
                   355                 360                 365
        Met Ile Pro Gln Tyr Gly Tyr Leu Thr Leu Asn Asp Gly Ser Gln Ala
               370                 375                 380
        Val Gly Arg Ser Ser Phe Tyr Cys Glu Tyr Phe Pro Ser Gln Met Leu
        385                 390                 395                 400
        Arg Thr Gly Asn Asn Phe Gln Phe Ser Tyr Glu Phe Glu Asn Val Pro
                           405                 410                 415
        Phe His Ser Ser Tyr Ala His Ser Gln Ser Leu Asp Arg Leu Met Asn
                       420                 425                 430
        Pro Leu Ile Asp Gln Tyr Leu Tyr Tyr Leu Ser Lys Thr Ile Asn Gly
                   435                 440                 445
        Ser Gly Gln Asn Gln Gln Thr Leu Lys Phe Ser Val Ala Gly Pro Ser
               450                 455                 460
        Asn Met Ala Val Gln Gly Arg Asn Tyr Ile Pro Gly Pro Ser Tyr Arg
        465                 470                 475                 480
        Gln Gln Arg Val Ser Thr Thr Val Thr Asn Asn Asn Ser Glu Phe Ala
                           485                 490                 495
```

```
Trp Pro Gly Ala Ser Ser Trp Ala Leu Asn Gly Arg Asn Ser Leu Met
            500                 505                 510

Asn Pro Gly Pro Ala Met Ala Ser His Lys Glu Gly Glu Asp Arg Phe
            515                 520                 525

Phe Pro Leu Ser Gly Ser Leu Ile Phe Gly Lys Gln Gly Thr Gly Arg
            530                 535                 540

Asp Asn Val Asp Ala Asp Lys Val Met Ile Thr Asn Glu Glu Glu Ile
545                 550                 555                 560

Lys Thr Thr Asn Pro Val Ala Thr Glu Ser Tyr Gly Gln Val Ala Thr
                565                 570                 575

Asn His Gln Ser Gln Ala Gln Ala Gln Thr Gly Trp Val Gln Asn Gln
            580                 585                 590

Gly Ile Leu Pro Gly Met Val Trp Gln Asp Arg Asp Val Tyr Leu Gln
            595                 600                 605

Gly Pro Ile Trp Ala Lys Ile Pro His Thr Asp Gly Asn Phe His Pro
            610                 615                 620

Ser Pro Leu Met Gly Gly Phe Gly Met Lys His Pro Pro Gln Ile
625                 630                 635                 640

Leu Ile Lys Asn Thr Pro Val Pro Ala Asp Pro Pro Thr Ala Phe Asn
                645                 650                 655

Lys Asp Lys Leu Asn Ser Phe Ile Thr Gln Tyr Ser Thr Gly Gln Val
            660                 665                 670

Ser Val Glu Ile Glu Trp Glu Gln Lys Glu Asn Ser Lys Arg Trp Asn
            675                 680                 685

Pro Glu Ile Gln Tyr Thr Ser Asn Tyr Tyr Lys Ser Asn Asn Val Glu
            690                 695                 700

Phe Ala Val Asn Thr Glu Gly Val Tyr Ser Glu Pro Arg Pro Ile Gly
705                 710                 715                 720

Thr Arg Tyr Leu Thr Arg Asn Leu
                725

<210> SEQ ID NO 32
<211> LENGTH: 738
<212> TYPE: PRT
<213> ORGANISM: Adeno-associated virus 10

<400> SEQUENCE: 32

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
```

-continued

```
            130                 135                 140
Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
                195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560
```

```
Met Leu Thr Ser Glu Glu Ile Lys Thr Thr Asn Pro Val Ala Thr
                565                 570                 575
Glu Gln Tyr Gly Val Val Ala Asp Asn Leu Gln Gln Asn Ala Ala
            580                 585                 590
Pro Ile Val Gly Ala Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Ser Gln Ala Lys Leu Ala Ser Phe
            660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
    690                 695                 700
Ser Asn Tyr Tyr Lys Ser Thr Asn Val Asp Phe Ala Val Asn Thr Asp
705                 710                 715                 720
Gly Thr Tyr Ser Glu Pro Arg Pro Ile Gly Thr Arg Tyr Leu Thr Arg
                725                 730                 735
Asn Leu

<210> SEQ ID NO 33
<211> LENGTH: 733
<212> TYPE: PRT
<213> ORGANISM: Adeno-associated virus 11

<400> SEQUENCE: 33

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Leu Glu Ser Pro Gln Glu Pro Asp Ser Ser Gly Ile Gly Lys
145                 150                 155                 160
Lys Gly Lys Gln Pro Ala Arg Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
```

```
Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605
```

```
Ile Tyr Tyr Gln Gly Pro Ile Trp Ala Lys Ile Pro His Ala Asp Gly
610                 615                 620

His Phe His Pro Ser Pro Leu Ile Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
                675                 680                 685

Ser Lys Arg Trp Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 34
<211> LENGTH: 741
<212> TYPE: PRT
<213> ORGANISM: Adeno-associated virus 12

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255
```

-continued

```
Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
            355                 360                 365

Val Phe Met Val Pro Gln Tyr Gly Tyr Cys Gly Val Val Thr Gly Lys
            370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
                420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
            450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
            530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
            610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
            660                 665                 670
```

-continued

```
Ile Asn Ser Phe Leu Thr Gln Tyr Ser Thr Gly Gln Val Ala Val Gln
        675                 680                 685

Ile Asp Trp Glu Ile Gln Lys Glu His Ser Lys Arg Trp Asn Pro Glu
        690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His
                740
```

MODIFIED MGLUR6 PROMOTER AND METHODS OF USE

CROSS-REFERENCE TO RELATED APPLICATIONS

This application is a U.S. National Stage Application, filed under 35 U.S.C. § 371, of International Application No. PCT/US2015/019985, filed Mar. 11, 2015 which claims the benefit of U.S. Provisional Application No. 61/951,360, filed Mar. 11, 2014, the contents which are herein incorporated by reference in their entirety.

GOVERNMENT SUPPORT

This invention was made with U.S. Government support under the National Institutes of Health/National Eye Institute grant NIH EY 17130. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 9, 2016, is named RTRO-705N01US_ST25.txt and is 151,625 bytes in size.

FIELD OF THE INVENTION

This invention relates generally to the field of molecular biology. The invention features modified metabotropic glutamate receptor 6 (mGluR6) promoters for increased expression in the retina. The modified mGluR6 promoters described herein are useful in ocular gene therapy for the improvement and/or restoration of vision.

BACKGROUND OF THE INVENTION

Gene therapy is a promising approach for improving and restoring vision. Particularly, delivery of genes, such as photosensitive proteins, to diseased or damaged retinas in mice have been recently shown to improve and restore photosensitivity and visual signals. However, challenges still remain for the efficient targeting and expression of such genes in specific inner retinal neurons for ocular gene therapy. Accordingly, there is a pressing need for improved regulatory elements and expression vectors for the delivery and expressing of transgenes for ocular gene therapy.

SUMMARY OF THE INVENTION

The invention provides a solution for the long-felt need for improved promoters and nucleic acid expression vectors for the delivery and expression of transgenes to the eye. Specifically, the promoters and vectors described herein comprise or consist essentially of a modified metabotropic glutamate receptor 6 (mGluR6) promoter that contains sequences from regulatory elements that direct the expression of the mGluR6 protein to ON bipolar cells, or retinal rod bipolar cells.

The present invention features an isolated nucleic acid molecule or a nucleic acid expression vector comprising an mGluR6 enhancer or a variant thereof and an mGluR6 promoter or a variant thereof. Optionally, the nucleic acid molecule further comprises intron 3 of the mGluR6 gene or a variant thereof. Optionally, the nucleic acid molecule further comprises intron 4 of the mGluR6 gene or a variant thereof.

The present invention features an isolated nucleic acid molecule or a nucleic acid expression vector comprising an mGluR6 enhancer or a variant thereof, an mGluR6 promoter or a variant thereof, an intron 3 of the mGluR6 gene or a variant thereof, and an intron 4 of the mGluR6 gene or a variant thereof.

A nucleic acid expression vector of the present invention may be a viral vector, preferably an adeno-associated virus vector or a recombinant adeno-associated virus (rAAV) vector. In other embodiments, the AAV vectors used with the present invention, e.g., a packaging vector, comprise a capsid protein.

The present invention also provides a pharmaceutical composition comprising one or more of the nucleic acid expression vectors described herein and a pharmaceutically acceptable excipient. In some embodiments, AAV vectors of more than one serotype may be combined into a single composition for administration, or may be administered sequentially over suitable time periods.

The present invention further provides a method for expressing a transgene in the eye comprising introducing into the eye the nucleic acid expression vector described herein. The nucleic acid expression vector may be introduced to the eye by subretinal, intraocular, or intravitreal injection. The methods described herein may be useful for increasing light sensitivity, increasing light detection, increasing photosensitivity, increasing visual evoked potential, or improving or restoring vision in a retina of a subject. For example, the subject suffers from an ocular disorder or disease associated with photoreceptor degeneration.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable non-limiting exemplary methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and are encompassed by the following detailed description and claims.

DETAILED DESCRIPTION

The metabotropic glutamate receptor (mGluR6, also known as Grm6) mediates the synaptic transmission in the nervous system and mediates the ON-response in the ON-pathway of the vertebrate retina. Expression of mGluR6 is found on ON-type retinal bipolar cells, which has made the promoter region of mGluR6 a good candidate for cell-specific promoter-driven expression in bipolar cells (Ueda et al., Journal Neurosci., 1997; hereby incorporated by reference in its entirety).

Modified mGluR6 Promoters

Previous studies have utilized a basal SV40 promoter with a mGluR6 enhancer sequence (e.g., 200 bp) for AAV-mediated targeting and expression in the eye (Doroudchi et al., Mol. Ther., 2011, 19:1220-1229). However, the transgene expression by these constructs was weak, and not fully selective. The invention described herein is based upon the surprising discovery that use of a fragment of the mGluR6 promoter region (e.g., about 1 kb or 500 bp) results in increased expression compared to SV40-based constructs, and, importantly, more selective expression in specific cell populations.

Figure 3:
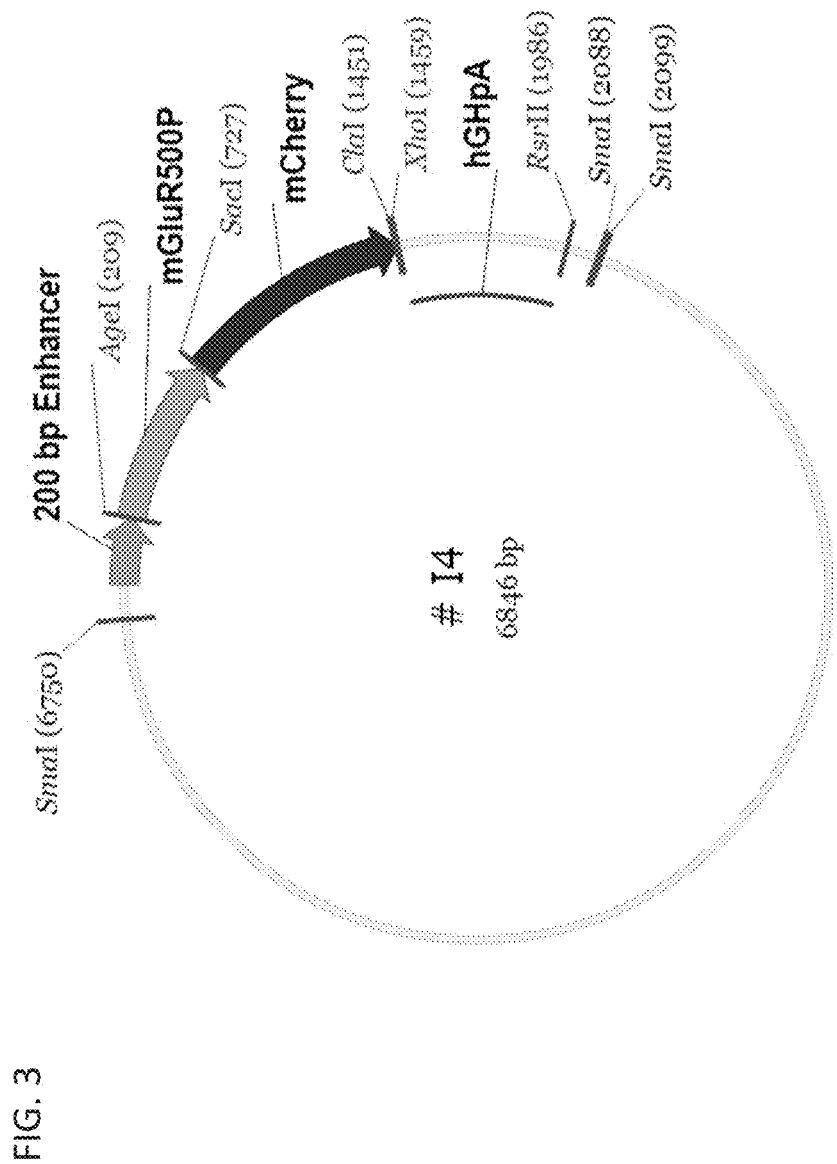
FIG. 3 shows a schematic diagram of an optimized promoter construct I4 comprising a 200 bp mGluR6 enhancer and a 500 bp fragment of the mGluR6 promoter upstream of a transgene (mCherry).
Figure 4:
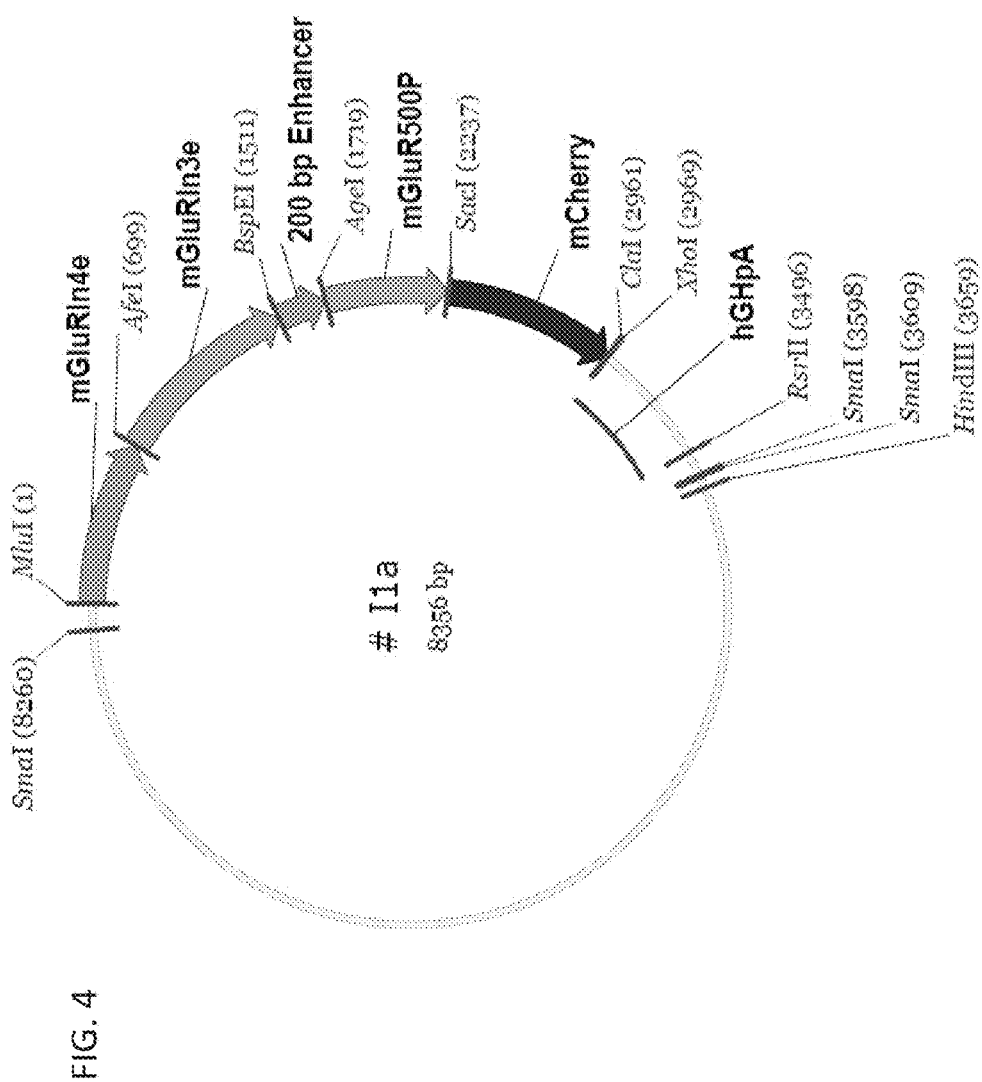
FIG. 4 shows a schematic diagram of an optimized promoter construct I1a comprising an intron 4 from mGluR6, intron 3 from mGluR6, a 200 bp mGluR6 enhancer and a 500 bp fragment of the mGluR6 promoter upstream of a transgene (mCherry).

The instant invention features modified mGluR6 promoters with increased efficiency and targeting transgene expression to bipolar cells. The promoters described herein were discovered by constructing various constructs with different combinations of regulatory elements present in the mGluR6 gene or predicted to be present. A modified mGluR6 promoter useful to achieve AAV-mediated selective and highly efficient expression in retinal bipolar cells was identified. As used herein, the term "modified mGluR6 promoter" refers to the combination of regulatory elements described herein that includes at least a 200 bp mGluR6 enhancer sequence and at least a fragment of the promoter region from mGluR6 gene (e.g., about a 1 kb or a 500 bp fragment). Optionally, the modified mGluR6 promoter also includes the intron sequences of the mGluR6 gene, e.g., intron 3 and intron 4. Exemplary modified mGluR6 constructs are shown in FIGS. 3 and 4.

The present invention provides a modified mGluR6 promoter that comprises at least a 200 bp mGluR6 enhancer. A preferred nucleic acid sequence for the murine 200 bp mGluR6 enhancer is provided below:

```
                                         (SEQ ID NO: 1)
gatctccagatggctaaacttttaaatcatgaatgaagtagatattacca aattgcttttt cagcatccatttagataatcatgtttttt gcctttaatc tgttaatgtagtgaattacagaaatacatttcctaaatcattacatcccc caaatcgttaatctgctaaagtacatctctggctcaaacaagactggttg tg
```

A preferred nucleic acid sequence for the human 198 bp mGluR6 enhancer (corresponding to the mouse 200 bp enhancer) is provided below in SEQ ID NO: 2:

```
gatccttagattatgaaacatttacaattatgaatgaatattagatgtta tcaaatgctttttctgcatccatttagataatcatgttttt ccttt aatc tgttaatgcggtgaattacattaatagatttcctaagtcattaatctgct aaagtgcatttctgggacaaaccagacttggttatgacattgtatgta
```

The modified mGluR6 promoter further comprises at least a fragment of the mGluR6 promoter region. A preferred example of this promoter region sequence consists of 11023 nucleotides (GenBank Accession No. BC041684). The original Ueda et al., study employed a 10 kb promoter, but the actual length of the promoter and the sequence that comprises control elements of mGluR6 can be adjusted by increasing or decreasing the fragment length. For example, a fragment of the promoter about 1 kb in length can be used as a mGluR6 promoter sequence. Promoter analysis can be used to identify promoter functional fragments and derivatives (McGowen at al. Mol. Vision 1998, 4:2; Bookstein et al. PNAS 1990, 87 (19) 7762-66).

The sequences provided herein are meant to be exemplary and in no way limit the scope of the invention. A person of ordinary skill in the art, in view of the instant disclosure, would be enabled to identify further suitable enhancer, promoter, transgene, and vector sequences.

For example, the mGluR6 promoter sequence used herein is a 1095 bp fragment of the mGluR6 promoter region. A nucleic acid sequence of the 1095 bp (about 1 kb) fragment of the murine mGluR6 promoter region is provided below in SEQ ID NO: 3:

```
taaccatgcacgctcgcacacgatagataatacatacaccaatatctgaa aagagaaaaggttctagtggtcaggacagagaatgaaaacggcaggaagg caagaaagtttgagaacgtaggggg tggg tagggagacactacgagtgg aataagccacgtttggagaacgtctaggcagatacagaaatgcagaacac agagagaccgagaccagagcagcgtcagaccggctgcaaggctcttgtta ggggctttagaaacacctgtgtgctctcccggaagcctggtgcagtcaga gaggaagcttgcttcccagacagagatgacacagtttcacaacctgtcag accaccttgcaggagagactgaacccagcaaccagaaccacttggctat gcatgtccttttctgtttaaacctaagtctctgaagaccgaccaggggag tccctggacttctttgttcctcttctcggggtggcgggactgattgtgta aatctcttatctccaactttcactcttatctgtctcttt aatcggcatat tgaggatgagtggccaagcttattggtgttgctgggtcagacaatttaaa ggcagtctaggggagaagcagacccagggagtcagagaggcagagagaga agagagcccttcctccactctcaagctctggagggggtctctgccctcac cctcatccctcccagaatccttaaatcctctagactgtagctctgattt
```

-continued

```
tacagctgtcacagactcgtcctactagccagaggttggctcaggtaagc accactggggaggtagcctagggtgcgctggggtgggtccagaggaagag ctgcccagaactgtggggaaggagcgggaccgaccatcaacaggggac ttttcagggagaatgagagcaatcctctggaggcctgggagaggctgctg agttgctggtgcgcgagtcaccaacttttcctgcgctctcggtgtccggc cagaatcccgaagtggcagctgagcacggggtggcagcttcgtccgccgg ctctcaaggcgtcccggtaacttcctttcccgcagtccaggagca
```

A preferred nucleic acid sequence of the human 1784 promoter (corresponding to the mouse mGluR 1095 bp promoter) fragment of the human mGluR6 promoter region provided below in SEQ ID NO: 4:

```
caagcaggaggctgctgtgtgctgggagctgtcaggctcgtcctgaacag ggaagggcccatccacctcccaaacccagtttatgcagtccttcgcaatg tcaggctcagggcctggcaccagccaagctccccacccttcccactgtta aaatggataggagcagggctaggcccagcctgttgactctgggcttccac caggagaagtggttctggcagtagaaactatcggggcctgggagaggcgg gggaagagagaaaggtggcatgtttcttgcttgctccctctaccagcctt gtccaaatccccgcagccaccctaatccagcctgtctaatggagcccaag ccggctcaggccctcggacgaggagcctgctaatccctgtggctaggagc tcaccacctgtctccaggacgccctttgctctcttggcatcagagagcca aatcctgggcctcggatggggggatgataaaagcatcttttggccaagcc ccctcaccttggcctccacgatgagatggggagttaggtgcagagagcgt tggcacagtgagcaccgcagctcgagtggctgcctcagacccagagcccg aggagactttatacggagccagaacgaccccgcggggttccatcctccca agcaataggcgggagtggggagctgcgaggaaagccggcccctcccctccc tccatccaaggcagtgtgggctgtttgtttcatgccattctgggtgtgaa tcctgatgcccacacatgccagctgcatgcacttgggcaactcaactcac tcctcgagggctgtttctcgactgcagggtgttgtaagttcgctaatact aaaggcttctccctcctggccccttcctgccccctcgctcttcctcctctt ccttaggccctcccagctcaggcagcccctgcccctgcagggttctgca aggagaaagctggggaatacttaggcaactgcagtcaggagcactggtg gccaggacagagacagagagacagaaaaggggtcagggacagagagagat aaccgcagggagagacaggaagggacagagacagaaaagatttccaagaa gaggacagaggcagaaagccagggacagagactgagaaacagagacctag aggcagaagaagactgagatagagatggacagagattgtgtcagacacag ccccagagacagccagacagtctgagtcagacgcaaaccaaagacaagaa aacaggaaaacagacccagagattgggagagggaggggaaggagatgcgg ggagagccagcaccgccaccccccacactcaggagggtctccaccctcg gagcggtctctcatccctccctagaatccttaaatcctctctcgctcagg gcctcggccgcatctgtcacagacttgtcctgaaccgacagcggctggcg caggtgactggcttggggcgggagcctgggtgtgcgctggggatggaccc
```

```
cgaggaagaggggccaagctgtcgggaagcggcagggctggagggtgga ggcagtggtcgggcgggacccgggcgacagggttcggcgcttgtaagag cgagacggaggcccgggcaggccggctgagctaactccccagagccgaag tggaaggcgcgccccgagcgccttctccccaggaccccggtgtccctccc cgcgccccgagcccgcgctctccttccccgccctcagagcgctccccgc ccctctgtctccccgcagcccgctagacgagccg
```

Preferably, the mGluR6 promoter sequence used herein is a 500 bp fragment of the mGluR6 promoter region. The 500 bp fragment described in SEQ ID NO: 5 is encompassed by the 1095 bp fragment described above (SEQ ID NO: 3). The 500 bp fragment is preferred because it results in higher expression than the 1095 bp fragment. A nucleic acid sequence of the 500 bp murine mGluR6 promoter is provided below in SEQ ID NO: 5:

```
ttaaaggcagtctaggggagaagcagacccagggagtcagagaggcagag agagaagagagcccttcctccactctcaagctctggaggggtctctgcc ctcaccctcatccctccccagaatccttaaatcctctagactgtagctct gattttacagctgtcacagactcgtcctactagccagaggttggctcagg taagcaccactggggaggtagcctagggtgcgctggggtgggtccagagg aagagctgcccagaactgtggggaaggagcgggaccgaccatcaacagg gggacttttcagggagaatgagagcaatcctctggaggcctgggagaggc tgctgagttgctggtgcgcgagtcaccaacttttcctgcgctctcggtgt ccggccagaatcccgaagtggcagctgagcacggggtggcagcttcgtcc gccggctctcaaggcgtcccggtaacttcctttcccgcagtccaggagca
```

A preferred nucleic acid sequence of the 547 bp human mGluR6 promoter, is encompassed by the 1784 bp fragment described above (SEQ ID NO: 4), and is provided below in SEQ ID NO: 6:

```
ccaaagacaagaaaacaggaaaacagacccagagattgggagagggaggg gaaggagatgcggggagagccagcaccgccaccccccacactcaggaggg gtctccaccctcggagcggtctctcatccctccctagaatccttaaatcc tctctcgctcagggcctcggccgcatctgtcacagacttgtcctgaaccg acagcggctggcgcaggtgactggcttggggcgggagcctgggtgtgcgc tggggatggacccgaggaagaggggccaagctgtcgggaagcggcaggg ctggaggggtggaggcagtggtcgggcgggacccgggcgacagggttcg gcgcttgtaagagcgagacggaggcccgggcaggccggctgagctaactc cccagagccgaagtggaaggcgcgccccgagcgccttctccccaggaccc cggtgtccctccccgcgccccgagcccgcgctctccttccccgccctca gagcgctccccgccctctgtctccccgcagcccgctagacgagccg
```

The modified mGluR6 promoters described herein may also include intron sequences from the mGluR6 gene. Preferably, introns 3 and 4 are included. The nucleic acid sequence of intron 4 of the murine mGluR6 gene is provided below in SEQ ID NO: 7:

```
ggtgagtccccacccactcatcctccctgatgcttcctgtgtgggatg
ctcatttccacatttgtctcggagtcccacatgctgagtaactctgagat
ttgctttaaaatgccatgcaggtaatttaaatgggaaggtctgatccaag
tgatgaagtgcagccttgatagcatgcttcctccgccctcccacaggctt
ccatcttttgtggggtgcccacctccacaccttttcttttagctagagtg
gtcaagtggacaagctggtcattagcaatcaaggcgtttcagatctggaa
gtgggtggtgccattatggatcagtgagccctgtattttttgtgcctctg
cacaaggtgggtagtgaagccctgtccattacataaccatggcatcccct
agccatgacataaagggcagtgaaaaattctttaaggatgccagagctgc
tttttccatttgtgtgtatgcgtgcaggtgtgtgttgtacatgacacaag
tgtatgtgtgtgcatgtggaggcctgaggttgatttcaggaatcatcctc
aattcttttctaccttattcactgaggcagggtctgtggagagatcacc
gatatggctactgtgggattcccctgtctctgccttcagagccactcctg
gatacacagtacacctggctcagatggtcaccaccctcct
```

The nucleic acid sequence of intron 4 of the human mGluR6 gene (corresponding to the mouse intron 4) is provided below in SEQ ID NO: 8:

```
tcccccaccccacacgtctcccagcaccccctcttggggatgctcattt
tctgcatctgtgtaattggtgccataatccagatcccttctcagatccc
agatcctatgagtccgatcatctgtggacgcgtccctccaagcagcgctt
gactgggatggcgtgcgaggaaagcacgctgacggggaggaattgttggg
tttttggttttgtttcttaatttagtgcctgtatttctagaaaccaagga
tacggaatataccatcctggtgatcagagtgatgaggcaggaacagatgg
ctcactttacaataggattgctcattttccccaagttgatgacatccttc
agggctattttatgaaacacattaggggatatataccatcacgcctggt
gcaggtggcagcctggactgagagtagttttagcgataaaggcatctcat
cacaagacaggaggtctgagagttggtgactttaggcatggggcagtgag
tgtgtggttgccttgggtcttcctgcatagtcacaagatggctgctgagg
ctccacccattacatcttcacagcagcatcctaacaggaaagagaggctc
tgagtttgcatcagcatgtaagtgccaccaatcagaacttggtcacctg
gccacgcctagctcacctggctcacctggccacgcctaactcacctggcc
actcctagctcacctggccatgcctagttcacctggccactcctagctca
cctggccactcctagctgaaagtgagcaagtggcagaaacacaccctccc
ccttctt
```

The nucleic acid sequence of intron 3 of the mGluR6 gene is provided below in SEQ ID NO: 9:

```
actccaggccatgagcaactcctcacatctccctaagcccttcctgtcgc
cctctggagtcttttgttctgggaatgagacaggcttgactggctgaagg
ttctccgggcctggcctgggaaacacaggaaaacacgactattttttattg
ttcattgtgggagagagaactggtaggcaaacccaagagcagaaaatgta
ccgtgagggacactgccccagtaaaccctgaaacctacattatcctaagc
cagccaaggttcttttccagcctgggaagttgagcgtgacattggtggct
gaatttgtagacagaatggcttctgagtgccctgacattccccaaaagg
aggctctctgcattaatccatttgtctttattataataaaaatatccaagt
cagggcgttttttaaggaaaagacttatttttaacatcaactcttggagg
tgaaagttcaggcagcgtgacaccagctctgctgaggacctagcttgcat
cacattttgacaaatgttatggaaagagggagtagagaaggaaagagtgc
atggagagaaggaacatcagaaagaagagggacagggttcactctttgat
agctattcaccttcacagaattacctcacccttccagaggtcaagagcaa
catcccagtgacccaataaccttgcactaagccacacctctttttttatt
ttttatgagacagggcctcactctgtatccctgaacttgctatgtggacc
aagctgtcctcttgagtgctgggattaaaggcattcagtatcagggctgg
tttataa
```

The nucleic acid sequence of intron 3 of the human mGluR6 gene (corresponding to the mouse intron 3) is provided below in SEQ ID NO: 10:

```
gggacagtggcacaatcaccgggcccctggggctctccctgagggtccca
cccctcctcttgcacatcgccaccttacacactctccctgcctccttttc
ccctgctcccgcaccccccaccttccctgctgctgcctctgagtctggt
gcccaggctcagaagcagcctggtctggggagatgccacaagcccagact
gaatagcgcacagaacatgtgtctgtgtttacagctcctgggggtgcggg
gagggacctgtgggcagaacctagtgcagaaaatgagctgtgagggaagg
agcccagggtccatacagaggctgcggacccccagcccgagacccaccggc
ccgagttcatctccagcctaggaggctgggtgtgacgctggtggaggcat
gtggggagggctggcttcgaactggattttcccccaaggagtccctctg
aaccccctgaacagtgggttacagtgggcagagcaagtgggcaggcctag
ggtcagaggaaagcccagggaaggtgccctaaatgccccggccccgttt
ttcctgagaaacaaggatctggtgagtgattatagagcaggggagatgga
tagagtgggaagggatgggggccgagctggaggaggctcccaggccctcc
ctcaccccagccctgctcctacc
```

Variants of the regulatory elements encompassed by the mGluR6 promoters described herein are also encompassed by the present invention. For example, a variant may have 50%, 55%, 60%, 65%, 70%, 75%, 80%, 85%, 90%, 95%, 96%, 97%, 98%, or 99% sequence identity to the nucleic acid sequences described herein. The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using search algorithms such as BLAST and PSI-BLAST (Altschul et al., 1990, J. Mol. Biol. 215:3, 403-410; Altschul et al., 1997, Nucleic Acids Res. 25:17, 3389-402).

For example, the mGluR6 enhancer is at least 60%, 65%, 70%, 75%, 80%, 85%, 90%, or 95% identical to SEQ ID NO: 1 or SEQ ID NO: 2. The mGluR6 promoter variant is at least 60%, 65%, 70%, 75%, 80%, 85%, 90%, or 95% identical to SEQ ID NO: 3, SEQ ID NO: 4, SEQ ID NO: 5, or SEQ ID NO: 6. The intron 4 of the mGluR6 gene variant is at least 60%, 65%, 70%, 75%, 80%, 85%, 90%, or 95% identical to SEQ ID NO: 7 or SEQ ID NO: 8. The intron 3 of the mGluR6 gene variant is at least 60%, 65%, 70%, 75%, 80%, 85%, 90%, or 95% identical to SEQ ID NO: 9 or SEQ ID NO: 10.

In one embodiment, the mGluR6 enhancer comprises the nucleic acid sequence of SEQ ID NO: 1 or SEQ ID NO: 2. The mGluR6 promoter comprises the nucleic acid sequence of SEQ ID NO: 3, SEQ ID NO: 4, SEQ ID NO: 5, or SEQ ID NO: 6. The intron 4 of the mGluR6 gene comprises the nucleic acid sequence of SEQ ID NO: 7 or SEQ ID NO: 8. The intron 3 of the mGluR6 gene comprises the nucleic acid sequence of SEQ ID NO: 9 or SEQ ID NO: 10.

In other embodiments, the intron 4 of the mGluR6 gene is located upstream of the intron 3 of the mGluR6 gene in the present invention. The intron 3 of the mGluR6 gene is located upstream of the mGluR6 enhancer in the present invention. The mGluR6 enhancer is located upstream of the mGluR6 promoter in the present invention.

For example, the mGluR6 enhancer is at least 60%, 65%, 70%, 75%, 80%, 85%, 90%, or 95% identical to SEQ ID NO: 1 or SEQ ID NO: 2. The mGluR6 promoter variant is at least 60%, 65%, 70%, 75%, 80%, 85%, 90%, or 95% identical to SEQ ID NO: 3, SEQ ID NO: 4, SEQ ID NO: 5, or SEQ ID NO: 6. The intron 4 of the mGluR6 gene variant is at least 60%, 65%, 70%, 75%, 80%, 85%, 90%, or 95% identical to SEQ ID NO: 7 or SEQ ID NO: 8. The intron 3 of the mGluR6 gene variant is at least 60%, 65%, 70%, 75%, 80%, 85%, 90%, or 95% identical to SEQ ID NO: 9 or SEQ ID NO: 10.

In one embodiment, the mGluR6 enhancer comprises the nucleic acid sequence of SEQ ID NO: 1 or SEQ ID NO: 2. The mGluR6 promoter comprises the nucleic acid sequence of SEQ ID NO: 3, SEQ ID NO: 4, SEQ ID NO: 5, or SEQ ID NO: 6. The intron 4 of the mGluR6 gene comprises the nucleic acid sequence of SEQ ID NO: 7 or SEQ ID NO: 8. The intron 3 of the mGluR6 gene comprises the nucleic acid sequence of SEQ ID NO: 9 or SEQ ID NO: 10.

In other embodiments, the intron 4 of the mGluR6 gene is located upstream of the intron 3 of the mGluR6 gene in the present invention. The intron 3 of the mGluR6 gene is located upstream of the mGluR6 enhancer in the present invention. The mGluR6 enhancer is located upstream of the mGluR6 promoter in the present invention.

In a preferred embodiment, the 200 bp mGluR6 enhancer is located upstream of the sequence from the mGluR6 promoter region. In another preferred embodiment, the intron 4 of the mGluR6 gene is upstream of the intron 3 of the mGluR6 gene, the intron 3 of the mGluR6 gene is upstream of the mGluR6 enhancer, and the mGluR6 enhancer is upstream of the mGluR6 promoter. The entire modified mGluR6 promoter (e.g., including the mGluR6 enhancer, mGluR6 promoter, and mGluR6 intron sequences) is located upstream of a particular transgene of interest to drive its expression. Alternatively, other orders or combinations of the regulatory elements may be advantageous for improving expression or targeting of the transgene.

The present invention further provides expression cassettes comprising the modified mGluR6 promoters described herein.

Transgenes

The expression of transgenes in the damaged or diseased retinas may be useful for improving or restoring vision. Transgenes of particular interest for restoration of photosensitivity or vision include photosensitive proteins, such as opsin genes or rhodopsin genes. As used herein, "transgene" refers to a polynucleotide encoding a polypeptide of interest, wherein the polynucleotide is encapsidated in a viral vector (e.g., rAAV).

The opsin family of genes includes vertebrate (animal) and invertebrate opsins. Animal opsins are G-protein coupled receptors (GPCRs) with 7-transmembrane helices which regulate the activity of ion channels. Invertebrate rhodopsins are usually not GPCRs but are light-sensitive or light-activated ion pumps or ion channels.

As referred to herein, an opsin gene or light-sensitive protein includes channel rhodopsins (e.g., ChR1, ChR2, vChR1 from Volvox carteri, vChR2, and other variants identified from any vertebrate, invertebrate, or microbe), halorhodopsins (NpHR), melanopsins, pineal opsins, bacteriorhodopsin, and functional variants, active binding fragments, or chimeras thereof. A light-sensitive protein of this invention can occur naturally in plant, animal, archaebacterial, algal, or bacterial cells, or can alternatively be created through laboratory techniques. Examples of opsin genes are discussed in further detail below.

Examples of channelrhodopsins as transgenes in the present invention include channelrhodopsins Chop1 (also known as ChR1) (GenBank accession number AB058890/AF385748) and Chop2 (also known as ChR2) (GenBank accession number AB058891/AF461397), as well as mutant ChR2 C128A, ChR2 C128S, ChR2 C128T, ChR1-ChR2 hybrids/chimeras, and variants thereof.

Chop1 and Chop2 are two rhodopsins from the green alga *Chlamydomonas reinhardtii* (Nagel, 2002; Nagel, 2003). Both are light-sensitive channels that, when expressed and activated in neural tissue, allow for a cell to be depolarized when stimulated with light (Boyden, 2005). The full length amino acid sequence of Chop1 is provided below in SEQ ID NO: 11:

MSRRPWLLALALAVALAAGSAGASTGSDATVPVATQDGPDYVFHRAHERM

LFQTSYTLENNGSVICIPNNGQCFCLAWLKSNGTNAEKLAANILQWITFA

LSALCLMFYGYQTWKSTCGWEEIYVATIEMIKFIIEYFHEFDEPAVIYSS

NGNKTVWLRYAEWLLTCPVILIHLSNLTGLANDYNKRTMGLLVSDIGTIV

WGTTAALSKGYVRVIFFLMGLCYGIYTFFNAAKVYIEAYHTVPKGICRDL

VRYLAWLYFCSWAMFPVLFLLGPEGFGHINQFNSAIAHAILDLASKNAWS

MMGHFLRVKIHEHILLYGDIRKKQKVNVAGQEMEVETMVHEEDDETQKVP

TAKYANRDSFIFMRDRLKEKGFETRASLDGDPNGDAEANAAAGGKPGMEM

GKMTGMGMGMGAGMGMATIDSGRVILAVPDISMVDFFREQFARLPVPYEL

-continued
VPALGAENTLQLVQQAQSLGGCDFVLMHPEFLRDRSPTGLLPRLKMGGQR

AAAFGWAAIGPMRDLIEGSGVDGWLEGPSFGAGINQQALVALINRMQQAK

KMGMMGGMGMGMGGGMGMGMGMGMAPSMNAGMTGGMGGASMGGAVMGM

GMGMQPMQQAMPAMSPMMTQQPSMMSQPSAMSAGGAMQAMGGVMPSPAPG

GRVGTNPLFGSAPSPLSSQPGISPGMATPPAATAAPAAGGSEAEMLQQLM

SEINRLKNELGE

The full length amino acid sequence of Chop2 is provided below in SEQ ID NO: 12:

MDYGGALSAVGRELLFVTNPVVVNGSVLVPEDQCYCAGWIESRGTNGAQT

ASNVLQWLAAGFSILLLMFYAYQTWKSTCGWEEIYVCAIEMVKVILEFFF

EFKNPSMLYLATGHRVQWLRYAEWLLTCPVILIHLSNLTGLSNDYSRRTM

GLLVSDIGTIVWGATSAMATGYVKVIFFCLGLCYGANTFFHAAKAYIEGY

HTVPKGRCRQVVTGMAWLFFVSWGMFPILFILGPEGFGVLSVYGSTVGHT

IIDLMSKNCWGLLGHYLRVLIHEHILIHGDIRKTTKLNIGGTEIEVETLV

EDEAEAGAVNKGTGKYASRESFLVMRDKMKEKGIDVRASLDNSKEVEQEQ

AARAAMMMMNGNGMGMGMGMNGMNGMGGMNGMAGGAKPGLELTPQLQPGR

VILAVPDISMVDFFREQFAQLSVTYELVPALGADNTLALVTQAQNLGGVD

FVLIHPEFLRDRSSTSILSRLRGAGQRVAAFGWAQLGPMRDLIESANLDG

WLEGPSFGQGILPAHIVALVAKMQQMRKMQQMQQIGMMTGGMNGMGGGMG

GGMNGMGGGNGMNNMGNGMGGGMGNGMGGNGMNGMGGGNGMNNMGGNGMA

GNGMGGGMGGNGMGGSMNGMSSGVVANVTPSAAGGMGGMMNGGMAAPQSP

GMNGGRLGTNPLFNAAPSPLSSQLGAEAGMGSMGGMGGMSGMGGMGGMGG

MGGAGAATTQAAGGNAEAEMLQNLMNEINRLKRELGE

A Chop2 fragment (315 amino acids) has been shown to efficiently increase photosensitivity and vision in murine models of photoreceptor degeneration (Bi et al., Neuron, 2006, and U.S. Pat. No. 8,470,790; both of which are hereby incorporated by reference). The amino acid sequence of this fragment is provided in below in SEQ ID NO: 13:

MDYGGALSAVGRELLFVTNPVVVNGSVLVPEDQCYCAGWIESRGTNGAQT

ASNVLQWLAAGFSILLLMFYAYQTWKSTCGWEEIYVCAIEMVKVILEFFF

EFKNPSMLYLATGHRVQWLRYAEWLLTCPVILIHLSNLTGLSNDYSRRTM

GLLVSDIGTIVWGATSAMATGYVKVIFFCLGLCYGANTFFHAAKAYIEGY

HTVPKGRCRQVVTGMAWLFFVSWGMFPILFILGPEGFGVLSVYGSTVGHT

IIDLMSKNCWGLLGHYLRVLIHEHILIHGDIRKTTKLNIGGTEIEVETLV

EDEAEAGAVNKGTGK

Chop2 mutants and variants as described in PCT Publication WO 2013/134295 (hereby incorporated by reference) may also be expressed using the promoters described herein. Any ChRs, or microbial opsins, or other genetically encoded light sensors or switches, presently known or as yet undiscovered, are useful in generating the compositions and practicing the methods of the invention.

Other suitable transgenes include Volvox carteri channelrhodopsins (e.g., vChR1 and vChR2). The amino acid sequence of vChR1, GenBank Accession No. EU285658.1, is provided in below in SEQ ID NO: 14:

MDYPVARSLIVRYPTDLGNGTVCMPRGQCYCEGWLRSRGTSIEKTIAITL

QWVVFALSVACLGWYAYQAWRATCGWEEVYVALIEMMKSIIEAFHEFDSP

ATLWLSSGNGVVWMRYGEWLLTCPVLLIHLSNLTGLKDDYSKRTMGLLVS

DVGCIVWGATSAMCTGWTKILFFLISLSYGMYTYFHAAKVYIEAFHTVPK

GICRELVRVMAWTFFVAWGMFPVLFLLGTEGFGHISPYGSAIGHSILDLI

AKNMWGVLGNYLRVKIHEHILLYGDIRKKQKITIAGQEMEVETLVAEEED

DTVKQSTAKYASRDSFITMRNRMREKGLEVRASLDAGGGDSGMEAGGGGA

AHAQPHMAKPGTELGKTMSASFTNGAATSLEPGRVILAVPDISMVDFFRE

QFAQLPVPYEVVPALGAENTVQLVQQAAMLGGCDFVLMHPEFLRDRGPTG

LLPQVKMMGQRTAAFGWSQMGPMRDLIESSGVGAWLEGPSFGSGISQAAL

QQLVVKMQQAKRMAAMGSMMGGGMGNGMGMGMGMGMGMGNGMGNGMGM

GNGMGNGMGMGNGMGNGMGMGNGMGMGNGMGMGNGMGMGNGMGNGMGNGM

GMGNGMGNGMGNGMGNGMGNGMGNGMGMGMGNGMGNGMGNGMGNGMGNGM

GNGMGMMTPGAMGMGMGGMGNLAAAAGNAMYGGGGGGGGSTMGSGNAAMM

TGLVMGGGNGVGAGPGGVVANLGSSALQPQSQMMGGGNVVGMSSPQLQLQ

QSSSMPLGGLAPNRIGNNPLFGAAPSPLHSQPGASPTGLSSPQLGMGAML

PAGTSVGAGGGSVGPTETDMLQQLMTEINRLKDELGE

The amino acid sequence of vChR2 is provided below in SEQ ID NO: 15:

MDHPVARSLIGSSYTNLNNGSIVIPSDACFCMKWLKSKGSPVALKMANAL

QWAAFALSVIILIYYAYATWRTTCGWEEVYVCCVELTKVVIEFFHEFDEP

GMLYLANGNRVLWLRYGEWLLTCPVILIHLSNLTGLKDDYNKRTMRLLVS

DVGTIVWGATAAMSTGYIKVIFFLLGCMYGANTFFHAAKVYIESYHTVPK

GLCRQLVRAMAWLFFVSWGMFPVLFLLGPEGFGHLSVYGSTIGHTIIDLL

SKNCWGLLGHFLRLKIHEHILLYGDIRKVQKIRVAGEELEVETLMTEEAP

DTVKKSTAQYANRESFLTMRDKLKEKGFEVRASLDNSGIDAVINHNNNYN

NALANAAAAVGKPGMELSKLDHVAANAAGMGGIADHVATTSGAISPGRVI

LAVPDISMVDYFREQFAQLPVQYEVVPALGADNAVQLVVQAAGLGGCDFV

LLHPEFLRDKSSTSLPARLRSIGQRVAAFGWSPVGPVRDLIESAGLDGWL

EGPSFGLGISLPNLASLVLRMQHARKMAAMLGGMGGMLGSNLMSGSGGVG

LMGAGSPGGGGGAMGVGMTGMGMVGTNAMGRGAVGNSVANASMGGGSAGM

GMGMMGMVGAGVGGQQQMGANGMGPTSFQLGSNPLYNTAPSPLSSQPGGD

ASAAAAAAAAAATGAASNSMNAMQAGGSVRNSGILAGGLGSMMGPPGAP

AAPTAAATAAPAVTMGAPGGGGAAASEAEMLQQLMAEINRLKSELGE

NpHR (Halorhodopsin) (GenBank accession number EF474018) is from the haloalkaliphilic archaeon Natronomonas pharaonis. The amino acid sequence of NpHR is provided below in SEQ ID NO: 16:

MTETLPPVTESAVALQAEVTQRELFEFVLNDPLLASSLYINIALAGLSIL

LFVFMTRGLDDPRAKLIAVSTILVPVVSIASYTGLASGLTISVLEMPAGH

```
FAEGSSVMLGGEEVDGVVTMWGRYLTWALSTPMILLALGLLAGSNATKLF

TAITFDIAMCVTGLAAALTTSSHLMRWFWYAISCACFLVVLYILLVEWAQ

DAKAAGTADMFNTLKLLTVVMWLGYPIVWALGVEGIAVLPVGVTSWGYSF

LDIVAKYIFAFLLLNYLTSNESVVSGSILDVPSASGTPADD
```

In certain embodiments variants of NpHR can be created. In specific embodiments single or multiple point mutations to the NpHR protein can result in NpHR variants. In specific embodiments a mammalian codon optimized version of NpHR can be utilized. In one embodiment NpHR variants are utilized. In one specific embodiment eNpHR (enhanced NpHR) is utilized. Addition of the amino acids FCYENEV (SEQ ID NO: 38) to the NpHR C-terminus along with the signal peptide from a β subunit of the nicotinic acetylcholine receptor to the NpHR N-terminus results in the construction of eNpHR.

Melanopsin (GenBank accession number 6693702) is a photopigment found in specialized photosensitive ganglion cells of the retina that are involved in the regulation of circadian rhythms, pupillary light reflex, and other non-visual responses to light. In structure, melanopsin is an opsin, a retinylidene protein variety of G-protein-coupled receptor. Melanopsin resembles invertebrate opsins in many respects, including its amino acid sequence and downstream signaling cascade. Like invertebrate opsins, melanopsin appears to be a bistable photopigment, with intrinsic photoisomerase activity. In certain embodiments variants of melanopsin can be created and used in the invention. In specific embodiments single or multiple point mutations to the melanopsin protein can result in melanopsin variants. The amino acid sequence of *Mus musculus* melanopsin (GenBank accession number 6693702) is provided below in SEQ ID NO: 17:

```
MDSPSGPRVLSSLTQDPSFTTSPALQGIWNGTQNVSVRAQLLSVSPTTSA

HQAAAWVPFPTVDVPDHAHYTLGTVILLVGLTGMLGNLTVIYTFCRNRGL

RTPANMFIINLAVSDFLMSVTQAPVFFASSLYKKWLFGETGCEFYAFCGA

VFGITSMITLTAIAMDRYLVITRPLATIGRGSKRRTALVLLGVWLYALAW

SLPPFFGWSAYVPEGLLTSCSWDYMTFTPQVRAYTMLLFCFVFFLPLLII

IFCYIFIFRAIRETGRACEGCGESPLRQRRQWQRLQSEWKMAKVALIVIL

LFVLSWAPYSTVALVAFAGYSHILTPYMSSVPAVIAKASAIHNPIIYAIT

HPKYRVAIAQHLPCLGVLLGVSGQRSHPSLSYRSTHRSTLSSQSSDLSWI

SGRKRQESLGSESEVGWTDTETTAAWGAAQQASGQSFCSQNLEDGELKAS

SSPQVQRSKTPKVPGPSTCRPMKGQGARPSSLRGDQKGRLAVCTGLSECP

HPHTSQFPLAFLEDDVTLRHL
```

The amino acid sequence of *Homo sapiens* melanopsin (GenBank accession number BC113558.1) is provided below in SEQ ID NO: 18:

```
MNPPSGPRVLPSPTQEPSCMATPAPPSWWDSSQSSISSLGRLPSISPTAP

GTWAAAWVPLPTVDVPDHAHYTLGTVILLVGLTGMLGNLTVIYTFCRSRS

LRTPANMFIINLAVSDFLMSFTQAPVFFTSSLYKQWLFGETGCEFYAFCG

ALFGISSMITLTAIALDRYLVITRPLATFGVASKRRAAFVLLGVWLYALA

WSLPPFFGWSAYVPEGLLTSCSWDYMSFTPAVRAYTMLLCCFVFFLPLLI

IIYCYIFIFRAIRETGRALQTFGACKGNGESLWQRQRLQSECKMAKIMLL

VILLFVLSWAPYSAVALVAFAGYAHVLTPYMSSVPAVIAKASAIHNPIIY

AITHPKYRVAIAQHLPCLGVLLGVSRRHSRPYPSYRSTHRSTLTSHTSNL

SWISIRRRQESLGSESEVGWTHMEAAAVWGAAQQANGRSLYGQGLEDLEA

KAPPRPQGHEAETPGKTKGLIPSQDPRM
```

Other suitable channel proteins of the invention include ChD, ChEF, ChF, ChIEF, and variants thereof.

Light-sensitive proteins may also include proteins that are at least about 10%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 95%, or at least about 99% identical to any of the light-sensitive proteins described herein (e.g., ChR1, ChR2, vChR1, vChR2, NpHR and melanopsin). The light-sensitive proteins of the present invention may also include proteins that have at least one mutation. The mutation may be a point mutation.

In some embodiments, light-sensitive proteins can modulate signaling within neural circuits and bidirectionally control behavior of ionic conductance at the level of a single neuron. In some embodiments the neuron is a retinal neuron, a retinal bipolar cell (e.g. ON or OFF retinal bipolar cells; rod and cone bipolar cells), a retinal ganglion cell, a photoreceptor cell, or a retinal amacrine cell.

In some embodiments, a polyA tail can be inserted downstream of the transgene in an expression cassette or nucleic acid expression vector of the present invention. Suitable polyA tails are known in the art, and include, for example, human growth hormone poly A tail (hGHpA), bovine growth hormone polyA tail (bGHpA), bovine polyA, 5V40 polyA, and AV40pA. The nucleic acid sequence of hGHpA is provided below in SEQ ID NO: 19:

```
gtcgagagatctacgggtggcatccctgtgacccctccccagtgcctctc ctggccctggaagttgccactccagtgcccaccagccttgtcctaataaa attaagttgcatcattttgtctgactaggtgtccttctataatattatgg ggtggaggggggtggtatggagcaaggggcaagttgggaagacaacctgt agggcctgcggggtctattgggaaccaagctggagtgcagtggcacaatc ttggctcactgcaatctccgcctcctgggttcaagcgattctcctgcctc agcctcccgagttgttgggattccaggcatgcatgaccaggctcagctaa ttttttgttttttggtagagacggggtttcaccatattggccaggctggt ctccaactcctaatctcaggtgatctacccaccttggcctcccaaattgc tgggattacaggcgtgaaccactgctcccttccctgtccttctgattttg taggtaaccacgtg
```

Vectors

The modified mGluR6 promoter sequences may be inserted into various different nucleic acid expression vectors. Vectors for use in the present invention can include various viral vectors, such as plasmids and recombinant viruses, e.g., recombinant adeno-associated virus (rAAV), recombinant adenoviruses, recombinant retroviruses, recombinant lentiviruses, and other viruses known in the art.

Adeno-associated viruses are small, single-stranded DNA viruses which require helper virus to facilitate efficient replication. The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and rescue and integration of the AAV into a host cell's chromosomes. The Cap reading frame encodes three structural proteins of molecular weight 85 kD (VP 1), 72 kD (VP2) and 61 kD (VP3) (Berns, cited above) which form the virion capsid. More than 80% of total proteins in AAV virion comprise VP3.

The genome of rAAV generally comprises: (1) a 5' adeno-associated virus ITR, (2) a coding sequence (e.g., transgene) for the desired gene product (e.g., a light-sensitive protein) operatively linked to a sequence which regulates its expression in a cell (e.g., a modified mGluR6 promoter sequence), and (3) a 3' adeno-associated virus inverted terminal repeat. In addition, the rAAV vector may preferably contain a polyadenylation sequence.

Generally, rAAV vectors have one copy of the AAV ITR at each end of the transgene or gene of interest, in order to allow replication, packaging, and efficient integration into cell chromosomes. The ITR consists of nucleotides 1 to 145 at the 5' end of the AAV DNA genome, and nucleotides 4681 to 4536 (e.g., the same sequence) at the 3' end of the AAV DNA genome. The rAAV vector may also include at least 10 nucleotides following the end of the ITR (e.g., a portion of the "D region").

The transgene sequence (e.g., the polynucleotide encoding a light-sensitive protein) can be of about 2 to 5 kb in length (or alternatively, the transgene may additionally contain a "stuffer" or "filler" sequence to bring the total size of the nucleic acid sequence between the two ITRs to between 2 and 5 kb). Alternatively, the transgene may be composed of repeated copies of the same or similar heterologous sequence several times (e.g., two nucleic acid molecules which encode one or more light-sensitive proteins separated by a ribosome readthrough, or alternatively, by an Internal Ribosome Entry Site or "IRES"), or several different heterologous sequences.

In one embodiment the vector comprises a recombinant AAV of a particular serotype, either naturally occurring or engineered. Adeno-associated viruses have been found in many animal species, including primates, canines, fowl and human. Presently, there are 12 different known serotypes, e.g., AAV1, AAV2, AAV3, AAV4, AAV5, AAV6, AAV7, AAV8, AAV9, AAV10, AAV11, and AAV12, all of which are appropriate for use in the present invention. Recombinant AAV vectors of the present invention may be generated from a variety of adeno-associated viruses, including for example, any of serotypes 1 through 12, as described herein. For example, ITRs from any AAV serotype are expected to have similar structures and functions with regard to replication, integration, excision, and transcriptional mechanisms.

For example, the nucleic acid expression vector of the present invention is an adeno-associated virus vector or a recombinant adeno-associated virus (rAAV) vector. In preferred embodiments, the vector is a recombinant AAV1, AAV2, AAV3, AAV4, AAV5, AAV6, AAV7, AAV8, AAV9, AAV10, AAV11, or AAV12 vector. In certain embodiments the AAV vector is of a wild-type serotype or variant of any of AAV1-AAV12, or a mutant, hybrid, or fragment thereof.

In other embodiments, the AAV vector is of a natural serotype or variant/mutant thereof that has yet to be discovered.

Viral and virus-like particles contemplated by the invention may be prepared by methods known to those of skill in the art, as well as those developed in the future. Virus producing cell lines and virus-like particle producing cell lines having the ability to produce sufficiently large quantities of virus are transfected with the vectors of the invention. Preferred production methods include, but are not limited to, the baculovirus expression vector system/insect cells and HEK 293 host cells. Other methods and host cell are suitable, such as those described in the art. See, e.g., Vicente, T. "Virus production for clinical gene therapy," Methods Mol. Biol., vol. 542:447-70 (2009).

The rAAV vector may also contain additional sequences, for example from an adenovirus, which assist in effecting a desired function for the vector. Such sequences include, for example, those which assist in packaging the rAAV vector into virus particles. Packaging cell lines suitable for producing adeno-associated viral vectors may be accomplished given available techniques (U.S. Pat. No. 5,872,005). Methods for constructing and packaging rAA7I vectors are described in, for example, WO 00/54813.

In other embodiments, the AAV vectors used with the present invention, e.g., a packaging vector, comprise a capsid protein. Suitable capsid proteins include, but are not limited to:

an AAV1 capsid protein comprising
the amino acid sequence of SEQ ID NO: 23:

AADGYLPDWLEDNLSEGIREWWDLKPGAPKPKANQQKQDDGRGLVLPGYK

YLGPFNGLDKGEPVNAADAAALEHDKAYDQQLKAGDNPYLRYNHADAEFE

RLQEDTSFGGNLGRAVFQAKKRVLEPLGLVEEGAKTAPGKKRPVEQSPQE

PDSSSGIGKTGQQPAKKRLNFGQTGDSESVPDPQPLGEPPATPAAVGTTM

ASGGGAPMADNNEGADGVGNASGNWHCDSTWLGDRVITTSTRTWALPTYN

NHLYKQISSASTGASNDNHYFGYSTPWGYFDFNRFHCHFSPRDWQLINNN

WGFRPKRLNFKLFNIQVKEVTTNDGVTTIANNLTSTVQVFSDSEYQLPYV

LGSAHQGCLPPFPADVFMIPQYGYLTLNNGSQAVGRSSFYCEYFPSQMLR

TGNNFTFSYTFEEVPFHSSYAHSQSLDRLMNPLIDQYLYYLNRTQNQSGS

AQNKDLLFSRGSPAGMSVQPKNWLPGPCYRQQRVSKTKTNNNSNFTWTGA

SKYNLNGRESIINPGTAMASHKDDEDKFFPMSGVMIFGKESAGASNTALD

NVMITDEEEIKATNPVATERFGTVAVNFQSSTDPATGDVHAMGALPGMVW

QDRDVYLQGPIWAKIPHTDGHFHPSPLMGGFGLKNPPPQILIKNTPVPAN

PPAEFSATKFASFITQYSTGQVSVEIEWEQKENSKRWNPEVQYTSNYAKS

ANVDFTVDNNGLYTEPRPIGTRYLTRPL an AAV2 capsid protein comprising the
amino acid sequence of SEQ ID NO: 24:

AADGYLPDWLEDTLSEGIRQWWKLKPGPPPPKPAERHKDDSRGLVLPGYK

YLGPFNGLDKGEPVNEADAAALEHDKAYDRQLDSGDNPYLKYNHADAEFE

RLKEDTSFGGNLGRAVFQAKKRVLEPLGLVEEPVKTAPGKKRPVEHSPVE

PDSSSGTGKAGQQPARKRLNFGQTGDADSVPDPQPLGQPPAAPSGLGNTM

ATGSGAPMADNNEGADGVGNSSGNWHCDSTWMGDRVITTSTRTWALPTYN

NHLYKQISSQSGASNDNHYFGYSTPWGYFDFNRFHCHFSPRDWQLINNNW

GFRPKRLNFKLFNIQVKEVTQNDGTTTIANNLTSTVQVFTDSEYQLPYVL

GSAHQGCLPPFPADVFMVPQYGYLTLNNGSQAVGRSSFYCEYFPSQMLRT

GNNNFTFSYTFEDVPFHSSYAHSQSLDRLMNPLIDQYLYYLSRTNTPSGTT

TQSRLQFSQAGASDIRDQSRNWLPGPCYRQQRVSKTSANNNSEYSWTGAT

KYHLNGRDSLVNPGPAMASHKDDEEKFFPQSGVLIFGKQGSEKTNVDIEK

VMITDEEEIRTTNPVATEQYGSVSTNLQRNRQAATADVNTQGVLPGMVWQ

DRDVYLQGPIWAKIPHTDGHFHPSPLMGGFGLKHPPPQILIKNTPVPANP

STTFSAAKFASFITQYSTGQVSVEIEWEQKENSKRWNPEIQYTSNYNKSV

NVDFTVDTNGVYSEPRPIGTRYLTRNL an AAV3 capsid protein comprising the
amino acid sequence of SEQ ID NO: 25:

AADGYLPDWLEDNLSEGIREWWALKPGVPQPKANQQHQDNRRGLVLPGYK

YLGPGNGLDKGEPVNEADAAALEHDKAYDQQLKAGDNPYLKYNHADAEFE

RLQEDTSFGGNLGRAVFQAKKRILEPLGLVEEAAKTAPGKKGAVDQSPQE

PDSSSGVGKSGKQPARKRLNFGQTGDSESVPDPQPLGEPPAAPTSLGNTM

ASGGGAPMADNNEGADGVGNSSGNWHCDSQWLGDRVITTSTRTWALPTYN

NHLYKQISSQSGASNDNHYFGYSTPWGYFDFNRFHCHFSPRDWQLINNNW

GFRPKKLSFKLFNIQVRGVTQNDGTTTIANNLTSTVQVFTDSEYQLPYVL

GSAHQGCLPPFPADVFMVPQYGYLTLNNGSQAVGRSSFYCEYFPSQMLRT

GNNNFQFSYTFEDVPFHSSYAHSQSLDRLMNPLIDQYLYYLNRTQGTTSGT

TNQSRLLFSQAGPQSMSLQARNWLPGPCYRQQRLSKTANNNNSNFPWTAA

SKYHLNGRDSLVNPGPAMASHKDDEEKFFPMHGNLIFGKEGTTASNAELD

NVMITDEEEIRTTNPVATEQYGTVANNLQSNTAPTTGTVNHQGALPGMVW

QDRDVYLQGPIWAKIPHTDGHFHPSPLMGGFGLKHPPPQIMIKNTPVPAN

PPTTFSPAKFASFITQYSTGQVSVEIEWEQKENSKRWNPEIQYTSNYNKS

VNVDFTVDTNGVYSEPRPIGTRYLTRNL an AAV4 capsid protein comprising the
amino acid sequence of SEQ ID NO: 26:

MTDGYLPDWLEDNLSEGVREWWALQPGAPKPKANQQHQDNARGLVLPGYK

YLGPGNGLDKGEPVNAADAAALEHDKAYDQQLKAGDNPYLKYNHADAEFQ

RLQGDTSFGGNLGRAVFQAKKRVLEPLGLVEQAGETAPGKKRPLIESPQQ

PDSSTGIGKKGKQPAKKKLVFEDETGAGDGPPEGSTSGAMSDDSMRAAAG

GAAVEGGQGADGVGNASGDWHCDSTWSEGHVTTTSTRTWVLPTYNNHLYK

RLGESLQSNTYNGFSTPWGYFDFNRFHCHFSPRDWQLINNNWGMRPKAMR

VKIFNIQVKEVTTSNGETTVANNLTSTVQIFADSSYELPYVMDAGQEGSL

PPFPNDVFMVPQYGYCGLVTGNTSQQQTDRNAFYCEYFPSQMLRTGNNFE

ITYSFEKVPFHSMYAHSQSLDRLMNPLIDQYLWGLQSTTTGTTLNAGTAT

TNFTKLRPTNFSNFKKNWLPGPSIKQQGFSKTANNYKIPATGSDSLIKYE

THSTLDGRWSALTPGPPMATAGPADSKFSNSQLIFAGPKQNGNTATVPGT

LIFTSEEELAATNATDTDMWGNLPGGDQSSNLPTVDRLTALGAVPGMVWQ

NRDIYYQGPIWAKIPHTDGHFHPSPLIGGFGLKHPPPQIFIKNTPVPANP

ATTFSSTPVNSFITQYSTGQVSVQIDWEQKERSKRWNPEVQFTSNYGQQN

SLLWAPDAAGKYTEPRAIGTRYLTHHL an AAV5 capsid protein comprising the
amino acid sequence of SEQ ID NO: 27:

SFVDHPPDWLEEVGEGLREFLGLEAGPPKPKPNQQHQDQARGLVLPGYNY

LGPGNGLDRGEPVNRADEVAREHDISYNEQLEAGDNPYLKYNHADAEFEK

LADDTSFGGNLGKAVFQAKKRVLEPFGLVEEGAKTAPTGKRIDDHFPKRK

KARTEEDSKPSTSSDAEAGPSGSQQLQIPAQPASSLGDTMSAGGGGPLGD

NNQGADGVGNASGDWHCDSTWMGDRVVTKSTRTWVLPSYNNHQYREIKSG

SVDGSNANAYFGYSTPWGYFDFNRFHSHWSPRDWQLINNYWGFRPRSLRV

KIFNIQVKEVTVQDSTTTIANNLTSTVQVFTDDDYQLPYVVGNGTEGCLP

AFPPQVFTLPQYGYATLNRDNTENPTERSSFFCEYFPSKMLRTGNNFEFT

YNFEEVPFHSSFAPSQNLFKLANPLVDQYLYRFVSTNNTGGVQFNKNLAG

RYANTYKNWFPGPMGRTQGWNLGSGNRASVSAFATTNRMELEGASYQVPP

QPNGMTNNLQGSNTYALENTMIFNSQPANPGTTATYLEGNMLITSESETQ

PVNRVAYNVGGQMATNNQSTTAPATGTYNLQEIVPGSVWMERDVYLQGPI

WAKIPETGAHFHPSPAMGGFGLKHPPPMMLIKNTPVPGNITSFSDVPVSS

FITQYSTGQVTVEMEWEKKENSKRWNPEIQYTNNYNDPQFVDFAPDSTGE

YRTTRPIGTRYLTRPL an AAV6 capsid protein comprising the
amino acid sequence of SEQ ID NO: 28:

AADGYLPDWLEDNLSEGIREWWDLKPGAPKPKANQQKQDDGRGLVLPGYK

YLGPFNGLDKGEPVNAADAAALEHDKAYDQQLKAGDNPYLRYNHADAEFE

RLQEDTSFGGNLGRAVFQAKKRVLEPFGLVEEGAKTAPGKKRPVEQSPQE

PDSSSGIGKTGQQPAKKRLNFGQTGDSESVPDPQPLGEPPATPAAVGTTM

ASGGGAPMADNNEGADGVGNASGNWHCDSTWLGDRVITTSTRTWALPTYN

NHLYKQISSASTGASNDNHYFGYSTPWGYFDFNRFHCHFSPRDWQLINNN

WGFRPKRLNFKLFNIQVKEVTTNDGVTTIANNLTSTVQVFSDSEYQLPYV

LGSAHQGCLPPFPADVFMIPQYGYLTLNNGSQAVGRSSFYCEYFPSQMLR

TGNNFTFSYTFEDVPFHSSYAHSQSLDRLMNPLIDQYLYYLNRTQNQSGS

AQNKDLLFSRGSPAGMSVQPKNWLPGPCYRQQRVSKTKTNNNSNFTWTGA

SKYNLNGRESIINPGTAMASHKDDKDKFFPMSGVMIFGKESAGASNTALD

NVMITDEEEIKATNPVATERFGTVAVNLQSSTDPATGDVHVMGALPGMVW

QDRDVYLQGPIWAKIPHTDGHFHPSPLMGGFGLKHPPPQILIKNTPVPAN

PPAEFSATKFASFITQYSTGQVSVEIEWEQKENSKRWNPEVQYTSNYAKS

ANVDFTVDNNGLYTEPRPIGTRYLTRPL an AAV7 capsid protein comprising the
amino acid sequence of SEQ ID NO: 29:

AADGYLPDWLEDNLSEGIREWWDLKPGAPKPKANQQKQDNGRGLVLPGYK

YLGPFNGLDKGEPVNAADAAALEHDKAYDQQLKAGDNPYLRYNHADAEFE

RLQEDTSFGGNLGRAVFQAKKRVLEPLGLVEEGAKTAPAKKRPVEPSPQR

SPDSSTGIGKKGQQPARKRLNFGQTGDSESVPDPQPLGEPPAAPSSVGGT
VAAGGGAPMADNNEGADGVGNASGNWHCDSTWLGDRVITTSTRTWALPTY
NNHLYKQISSETAGSTNDNTYFGYSTPWGYFDFNRFHCHFSPRDWQLINN
NWGFRPKKLRFKLFNIQVKEVTTNDGVTTIANNLTSTIQVFSDSEYQLPY
VLGSAHQGCLPPFPADVFMIPQYGYLTLNNGSQSVGRSSFYCEYFPSQML
RTGNNFEFSYSFEDVPFHSSYAHSQSLDRLMNPLIDQYLYYLARTQSNPG
GTAGNRELQFYQGGPSTMAEQAKNWLPGPCFRQQRVSKTLDNNNSNFAWT
GATKYHLNGRNSLVNPGVAMATHKDDEDRFFPSSGVLIFGKTGATNKTTL
ENVLMTNEEEIRPTNPVATEEYGIVSSNLQANTAAQTQVVNNQGALPGMV
WQNRDVYLQGPIWAKIPHTDGNFHPSPLMGGFGLKHPPPQILIKNTPVPA
NPPEVFTPAKFASFITQYSTGQVSVEIEWEQKENSKRWNPEIQYTSNFEK
QTGVDFAVDSQGVYSEPRPIGTRYLTRNL an AAV8 capsid protein comprising the
amino acid sequence of SEQ ID NO: 30:
AADGYLPDWLEDNLSEGIREWWALKPGAPKPKANQQKQDDGRGLVLPGYK
YLGPFNGLDKGEPVNAADAAALEHDKAYDQQLQAGDNPYLRYNHADAEFE
RLQEDTSFGGNLGRAVFQAKKRVLEPLGLVEEGAKTAPGKKRPVEPSPQR
SPDSSTGIGKKGQQPARKRLNFGQTGDSESVPDPQPLGEPPAAPSGVGNT
MAAGGGAPMADNNEGADGVGSSSGNWHCDSTWLGDRVITTSTRTWALPTY
NNHLYKQISNGTSGGATNDNTYFGYSTPWGYFDFNRFHCHFSPRDWQLIN
NNWGFRPKRLSFKLFNIQVKEVTQNEGTKTIANNLTSTIQVFTDSEYQLP
YVLGSAHQGCLPPFPADVFMIPQYGYLTLNNGSQAVGRSSFYCEYFPSQM
LRTGNNFQFTYTFEDVPFHSSYAHSQSLDRLMNPLIDQYLYYLSRTQTTG
GTANTQTLGFSQGGPNTMANQAKNWLPGPCYRQQRVSTTTGNNNSNFAWT
AGTKYHLNGRNSLANPGIAMATHKDDEERFFPSNGILIFGKQNAARDNAD
YSDVMLTSEEEIKTTNPVATEEYGIVADNLQQNTAPQIGTVNSQGALPGM
VWQNRDVYLQGPIWAKIPHTDGNFHPSPLMGGFGLKHPPPQILIKNTPVP
ADPPTTFNQSKLNSFITQYSTGQVSVEIEWEQKENSKRWNPEIQYTSNYY
KSTSVDFAVNTEGVYSEPRPIGTRYLTRNL an AAV9 capsid protein comprising the
amino acid sequence of SEQ ID NO: 31:
AADGYLPDWLEDNLSEGIREWWALKPGAPQPKANQQHQDNARGLVLPGYK
YLGPGNGLDKGEPVNAADAAALEHDKAYDQQLKAGDNPYLKYNHADAEFE
RLKEDTSFGGNLGRAVFQAKKRLLEPLGLVEEAAKTAPGKKRPVEQSPQE
PDSSAGIGKSGAQPAKKRLNFGQTGDTESVPDPQPIGEPPAAPSGVGLTM
ASGGGAPVADNNEGADGVGSSSGNWHCDSQWLGDRVITTSTRTWALPTYN
NHLYKQISNSTSGGSSNDNAYFGYSTPWGYFDFNRFHCHFSPRDWQLINN
NWGFRPKRLNFKLFNIQVKEVTDNNGVKTIANNLTSTVQVFTDSDYQLPY
VLGSAHEGCLPPFPADVFMIPQYGYLTLNDGSQAVGRSSFYCEYFPSQML
RTGNNFQFSYEFENVPFHSSYAHSQSLDRLMNPLIDQYLYYLSKTINGSG
QNQQTLKFSVAGPSNMAVQGRNYIPGPSYRQQRVSTTVTNNNSEFAWPGA
SSWALNGRNSLMNPGPAMASHKEGEDRFFPLSGSLIFGKQGTGRDNVDAD
KVMITNEEEIKTTNPVATESYGQVATNHQSQAQAQTGWVQNQGILPGMVW
QDRDVYLQGPIWAKIPHTDGNFHPSPLMGGFGMKHPPPQILIKNTPVPAD
PPTAFNKDKLNSFITQYSTGQVSVEIEWEQKENSKRWNPEIQYTSNYYKS
NNVEFAVNTEGVYSEPRPIGTRYLTRNL an AAV10 capsid protein comprising the
amino acid sequence of SEQ ID NO: 32:
MAADGYLPDWLEDNLSEGIREWWDLKPGAPKPKANQQKQDDGRGLVLPGY
KYLGPFNGLDKGEPVNAADAAALEHDKAYDQQLKAGDNPYLRYNHADAEF
QERLQEDTSFGGNLGRAVFQAKKRVLEPLGLVEEGAKTAPGKKRPVEPSP
QRSPDSSTGIGKKGQQPAKKRLNFGQTGDSESVPDPQPIGEPPAGPSGLG
SGTMAAGGGAPMADNNEGADGVGSSSGNWHCDSTWLGDRVITTSTRTWAL
PTYNNHLYKQISNGTSGGSTNDNTYFGYSTPWGYFDFNRFHCHFSPRDWQ
RLINNNWGFRPKRLNFKLFNIQVKEVTQNEGTKTIANNLTSTIQVFTDSE
YQLPYVLGSAHQGCLPPFPADVFMIPQYGYLTLNNGSQAVGRSSFYCLEY
FPSQMLRTGNNFEFSYQFEDVPFHSSYAHSQSLDRLMNPLIDQYLYYLSR
TQSTGGTAGTQQLLFSQAGPNNMSAQAKNWLPGPCYRQQRVSTTLSQNNN
SNFAWTGATKYHLNGRDSLVNPGVAMATHKDDEERFFPSSGVLMFGKQGA
GKDNVDYSSVMLTSEEEIKTTNPVATEQYGVVADNLQQQNAAPIVGAVNS
QGALPGMVWQNRDVYLQGPIWAKIPHTDGNFHPSPLMGGFGLKHPPPQIL
IKNTPVPADPPTTFSQAKLASFITQYSTGQVSVEIEWELQKENSKRWNPE
IQYTSNYYKSTNVDFAVNTDGTYSEPRPIGTRYLTRNL an AAV11 capsid protein comprising the
amino acid sequence of SEQ ID NO: 33:
MAADGYLPDWLEDNLSEGIREWWDLKPGAPKPKANQQKQDDGRGLVLPGY
KYLGPFNGLDKGEPVNAADAAALEHDKAYDQQLKAGDNPYLRYNHADAEF
QERLQEDTSFGGNLGRAVFQAKKRVLEPLGLVEEGAKTAPGKKRPLESPQ
EPDSSSGIGKKGKQPARKRLNFEEDTGAGDGPPEGSDTSAMSSDIEMRAA
PGGNAVDAGQGSDGVGNASGDWHCDSTWSEGKVTTTSTRTWVLPTYNNHL
YLRLGTTSSSNTYNGFSTPWGYFDFNRFHCHFSPRDWQRLINNNWGLRPK
AMRVKIFNIQVKEVTTSNGETTVANNLTSTVQIFADSSYELPYVMDAGQE
GSLPPFPNDVFMVPQYGYCGIVTGENQNQTDRNAFYCLEYFPSQMLRTGN
NFEMAYNFEKVPFHSMYAHSQSLDRLMNPLLDQYLWHLQSTTSGETLNQG
NAATTFGKIRSGDFAFYRKNWLPGPCVKQQRFSKTASQNYKIPASGGNAL
LKYDTHYTLNNRWSNIAPGPPMATAGPSDGDFSNAQLIFPGPSVTGNTTT
SANNLLFTSEEEIAATNPRDTDMFGQIADNNQNATTAPITGNVTAMGVLP
GMVWQNRDIYYQGPIWAKIPHADGHFHPSPLIGGFGLKHPPPQIFIKNTP
VPANPATTFTAARVDSFITQYSTGQVAVQIEWEIEKERSKRWNPEVQFTS
NYGNQSSMLWAPDTTGKYTEPRVIGSRYLTNHL an AAV12 capsid protein comprising the
amino acid sequence of SEQ ID NO: 34:
MAADGYLPDWLEDNLSEGIREWWALKPGAPQPKANQQHQDNGRGLVLPGY
KYLGPFNGLDKGEPVNEADAAALEHDKAYDKQLEQGDNPYLKYNHADAEF -continued

QQRLATDTSFGGNLGRAVFQAKKRILEPLGLVEEGVKTAPGKKRPLEKTP

NRPTNPDSGKAPAKKKQKDGEPADSARRTLDFEDSGAGDGPPEGSSSGEM

SHDAEMRAAPGGNAVEAGQGADGVGNASGDWHCDSTWSEGRVTTTSTRTW

VLPTYNNHLYLRIGTTANSNTYNGFSTPWGYFDFNRFHCHFSPRDWQRLI

NNNWGLRPKSMRVKIFNIQVKEVTTSNGETTVANNLTSTVQIFADSTYEL

PYVMDAGQEGSFPPFPNDVFMVPQYGYCGVVTGKNQNQTDRNAFYCLEYF

PSQMLRTGNNFEVSYQFEKVPFHSMYAHSQSLDRMMNPLLDQYLWHLQST

TTGNSLNQGTATTTYGKITTGDFAYYRKNWLPGACIKQQKFSKNANQNYK

IPASGGDALLKYDTHTTLNGRWSNMAPGPPMATAGAGDSDFSNSQLIFAG

PNPSGNTTTSSNNLLFTSEEEIATTNPRDTDMFGQIADNNQNATTAPHIA

NLDAMGIVPGMVWQNRDIYYQGPIWAKVPHTDGHFHPSPLMGGFGLKHPP

PQIFIKNTPVPANPNTTFSAARINSFLTQYSTGQVAVQIDWEIQKEHSKR

WNPEVQFTSNYGTQNSMLWAPDNAGNYHELRAIGSRFLTHHL

The capsid protein may have at least one mutation, for example, an amino acid substitution. In some cases, a recombinant adeno-associated viral (rAAV) vector comprises a capsid protein with a mutated tyrosine residue which enables to the vector to have improved transduction efficiency of a target cell, e.g., a retinal bipolar cell (e.g. ON or OFF retinal bipolar cells; rod and cone bipolar cells). In some cases, the rAAV further comprises a promoter (e.g., mGluR6, or fragment thereof) capable of driving the expression of a protein of interest in the target cell.

In one embodiment, a mutation may be made in any one or more of tyrosine residues of the capsid protein of AAV 1-12 or hybrid AAVs. In specific embodiments these are surface exposed tyrosine residues. In a related embodiment the tyrosine residues are part of the VP1, VP2, or VP3 capsid protein. In exemplary embodiments, the mutation may be made at one or more of the following amino acid residues of an AAV-VP3 capsid protein: Tyr252, Tyr272, Tyr444, Tyr500, Tyr700, Tyr704, Tyr730; Tyr275, Tyr281, Tyr508, Tyr576, Tyr612, Tyr673 or Tyr720. Exemplary mutations are tyrosine-to-phenylalanine mutations including, but not limited to, Y252F, Y272F, Y444F, Y500F, Y700F, Y704F, Y730F, Y275F, Y281F, Y508F, Y576F, Y612G, Y673F and Y720F. In a specific embodiment these mutations are made in the AAV2 serotype. In some cases, an AAV2 serotype comprises a Y444F mutation and/or an AAV8 serotype comprises a Y733F mutation, wherein 444 and 733 indicate the location of a point tyrosine mutation of the viral capsid. In further embodiments, such mutated AAV2 and AAV8 serotypes encode a light-sensitive protein and also comprise a modified mGluR6 promoter to drive expression of such light-sensitive protein. Such AAV vectors are described in, for example, Petrs-Silva et al., Mol. Ther., 2011 19:293-301).

In preferred embodiments, the amino acid mutation is of one or more of the surface tyrosine residues (e.g., Y252, Y272, Y444, Y500, Y700, Y704, and Y730 of an AAV2 capsid protein), surface threonine residues (e.g., T251, T329, T330, T454, T455, T503, T550, T592, T581, T597, T491, T671, T659, T660, T701, T713, and T716 of an AAV2 capsid protein), surface serine residues (e.g., S261, S264, S267, S276, S384, S458, S468, S492, S498, S578, S658, S662, S668, S707, S721 of an AAV2 capsid protein), and/or surface lysine residues (e.g., 258, K321, K459, K490, K507, K527, K572, K532, K544, K549, K556, K649, K655, K665, K706 of an AAV2 capsid protein). These residues are highly conserved between AAV1-AAV12 capsids, thus embodiments utilizing AAV1-AAV12 are encompassed herein and could be readily developed by those of ordinary skill viewing the instant disclosure. Preferred capsid mutants of the invention increase transduction efficiency compared with wild-type capsid proteins.

In one aspect, the mutation is a tyrosine (Y) to phenylalanine (F) at one or more of Y252, Y272, Y444, Y500, Y700, Y704, and Y730 of an AAV2 capsid protein or an equivalent conserved residue of AAV1 or AAV3-12. In a preferred embodiment, the Y to F mutation is at amino acid position 444 and/or position 730 of an AAV2 capsid protein or an equivalent conserved residue of AAV1 or AAV3-12. In another preferred embodiment, the mutant is a quadruple mutant with Y to F mutations at Y272, Y444, Y500, and Y730. Petrs-Silva, H. et al., "Novel Properties of Tyrosine-mutant AAV2 Vectors in the Mouse Retina," Mol. Ther., vol. 19(2): 293-301 (2011).

In another aspect, the mutation is a threonine (T) to valine (V) at one or more of T251, T329, T330, T454, T455, T503, T550, T592, T581, T597, T491, T671, T659, T660, T701, T713, and T716 of an AAV2 capsid protein or an equivalent conserved residue of AAV1 or AAV3-12. In a preferred embodiment, the T to V mutation is at amino acid position 491 of an AAV2 capsid protein or an equivalent conserved residue of AAV1 or AAV3-12. In yet another embodiment, the mutant capsid comprises Y to F mutations at Y272, Y444, Y500, and Y730, as well as a T to V mutation is at amino acid position 491 of an AAV2 capsid protein or an equivalent conserved residue of AAV1 or AAV3-12. Kay, C. N. et al., "Targeting Photoreceptors via Intravitreal Delivery Using Novel, Capsid-Mutated AAV Vectors," PLoS One, vol. 8(4): e62097 (2013).

In another embodiment, the capsid protein is engineered to include the insert of peptide 7m8 at AAV2$^{588}$, SEQ ID NO: 35: LGETTRP. Dalkara, D. et al., "In Vivo-Directed Evolution of a New Adeno-Associated Virus for Therapeutic Outer Retinal Gene Delivery from the Vitreous," Sci. Transl. Med. 5(189):ra76 (2013).

In another embodiment, the capsid protein is engineered to include a 9-amino acid stretch of a conformationally variable region of the AAV8 capsid protein between positions 585 and 593. In some embodiments, the capsid protein comprises SEQ ID NO: 36, PERTAMSLP. In preferred embodiments, SEQ ID NO: 36 is inserted between positions 585 and 593 of an AAV2 capsid protein or the equivalent conserved residues of AAV1 or AAV3-12. The capsid proteins comprising this sequence effectively transduce ocular cells, preferably bipolar and ganglion cells. In some embodiments, the capsid protein comprises SEQ ID NO: 37, SFSRAVLCD. In preferred embodiments, SEQ ID NO: 37 is inserted between positions 585 and 593 of an AAV2 capsid protein or the equivalent conserved residues of AAV1 or AAV3-12. The capsid proteins comprising this sequence effectively transduce ocular cells, preferably ON bipolar cells. Cronin, T. et al., "Efficient transduction and optogenetic stimulation of retinal bipolar cells by a synthetic adeno-associated virus capsid and promoter," EMBO Mol. Med., vol. 6(9): 1175-1190 (2014).

In any of the isolated nucleic acid molecules or nucleic acid expression vectors described herein, the modified mGluR6 promoter is upstream of a transgene to be expressed in the eye. Preferably, the transgene encodes a gene product that increases light sensitivity, increases light detection, increases photosensitivity, increases visual evoked potential, or restores vision in a retina. More preferably, the transgene is an opsin gene. Examples of opsin genes include, but are not limited to, channelrhodopsins (e.g., channelrhodopsin-1, channelrhodopsin-2, and Volvox carteri channelrhodopsins 1 or 2), melanopsin, pineal opsin, photopsins, halorhodopsin, bacteriorhodopsin, proteorhodopsin, or any functional variants or fragments thereof. Suitable opsin variants may be 60%, 65%, 70%, 75%, 80%, 85%, 90%, 95%, 96%, 97% 98% or 99% identical to the opsin. Preferably, the opsin variant has at least 60%, 65%, 70%, 75%, 80%, 85%, 90%, 95%, 96%, 97%, 98%, or 99% of the functional activity of the opsin. Functional activity can be measured by any means known in the art, for example, by electroretinography.

Preferably, the mutation in the capsid protein is a tyrosine to phenylalanine at amino acid position 444. The ordinarily skilled artisan could readily design nucleic acid sequences that encode said mutated capsid protein. A nucleic acid sequence for such an exemplary capsid protein is provided below in SEQ ID NO: 20:

```
tcagagagagtgtcctcgagccaatctgaaacaataccatcggcagccat
acctgatttaaatcatttattgttcaaagatgcagtcatccaaatccaca
ttgaccagatcgcaggcagtgcaagcgtctggcacctttcccatgatatg
atgaatgtagcacagtttctgatacgccttttgacgacagaaacgggtt
gagattctgacacgggaaagcactctaaacagtctttctgtccgtgagtg
aagcagatatttgaattctgattcattctctcgcattgtctgcagggaaa
cagcatcagattcatgcccacgtgacgagaacatttgtttggtacctgt
ctgcgtagttgatcgaagcttccgcgtctgacgtcgatggctgcgcaact
gactcgcgcacccgtttgggctcacttatatctgcgtcactggggcggg
tcttttcttggctccacccttttttgacgtagaattcatgctccacctcaa
ccacgtgatcctttgcccaccggaaaaagtctttgacttcctgcttggtg
accttcccaaagtcatgatccagacggcgggtgagttcaaatttgaacat
ccggtcttgcaacggctgctggtgttcgaaggtcgttgagttcccgtcaa
tcacggcgcacatgttggtgttggaggtgacgatcacgggagtcgggtct
atctgggccgaggacttgcatttctggtccacgcgcaccttgcttcctcc
gagaatggctttggccgactccacgaccttggcggtcatcttcccctcct
cccaccagatcaccatcttgtcgacacagtcgttgaagggaaagttctca
ttggtccagtttacgcacccgtagaagggcacagtgtgggctatggcctc
cgcgatgttggtcttcccggtagttgcaggcccaaacagccagatggtgt
tcctcttgccgaacttttcgtggcccatcccagaaagacggaagccgca
tattgggatcgtaccgtttagttccaaaatttataaatccgattgct
ggaaatgtcctccacgggctgctggcccaccaggtagtcggggcggttt
tagtcaggctcataatctttcccgcattgtccaaggcagccttgatttgg
gaccgcgagttggaggccgcattgaaggagatgtatgaggcctggtcctc
ctggatccactgcttctccgaggtaatcccttgtccacgagccacccga
ccagctccatgtacctggctgaagttttttgatctgatcaccggcgcatca
gaattgggattctgattctctttgttctgctcctgcgtctgcgacacgtg
cgtcagatgctgcgccaccaaccgtttacgctccgtgagattcaaacagg
cgctgaaacaataggaagggagtggatgtcagtgtgtgctgcccgggggc
tctgactacaggtctcccccttcgcgcccgatggtgggacggtatgaata
atccggaatatttataggtttttttattacaaaactgttacgaaaacagt
aaaatacttatttatttgcgagatggttatcattttaattatctccatga
tagatctctatcactgatagggagtacttacctttaaatactgttccatat
tagtccacgcccactggagctcaggctgggtttgggagcaagtaattg
gggatgtagcactcatccaccaccttgttcccgcctccggcgccatttct
ggtctttgtgaccgcgaaccagtttggcaaagtcggctcgatcccgcgt
aaattctctgaatcagttttttcgcgaatctgactcaggaaacgtcccaaa
accatggatttcaccccggtggtttccacgagcacgtgcatgtggaagta
gctctctcccttctcaaattgcacaaagaaaagggcctccggggccttac
tcacacggcgccattccgtcagaaagtcgcgctgcagcttctcggccacg
gtcagggtgcctgctcaatcagattcagatccatgtcagaatctggcgg
caactcccattccttctcggccacccagttcacaaagctgtcagaaatgc
cgggcagatgctcgtcaaggtcgctggggaccttaatcacaatctcgtaa
aaccccggcat
```

In some embodiments, self-complementary AAV vectors may be used in the present invention. These vectors feature an inverted repeat genome that can fold into double-stranded DNA (dsDNA) without the requirement for DNA synthesis or base-pairing between multiple vector genomes. Self-complementary vectors are particularly efficient for transduction, as the vectors hybridize for the priming of transcription, thereby effectively bypassing the step of converting single-stranded DNA (ssDNA to dsDNA). Self-complementary vectors and methods of their use are described in McCarty et al., Mol. Ther., 2008, 16:1648-1656.

Figure 1:
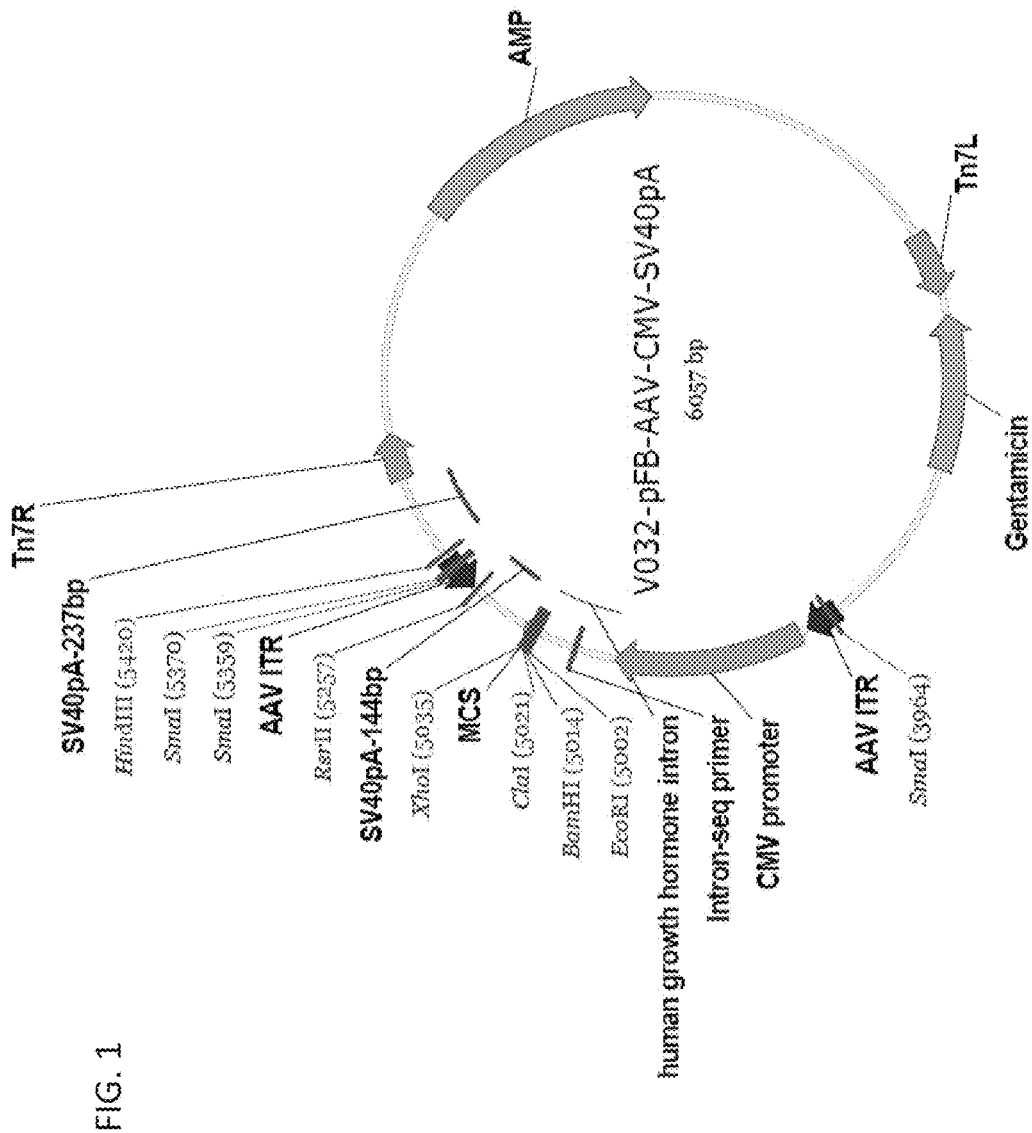
FIG. 1 shows a schematic diagram of an rAAV2 genome vector.
Figure 2:
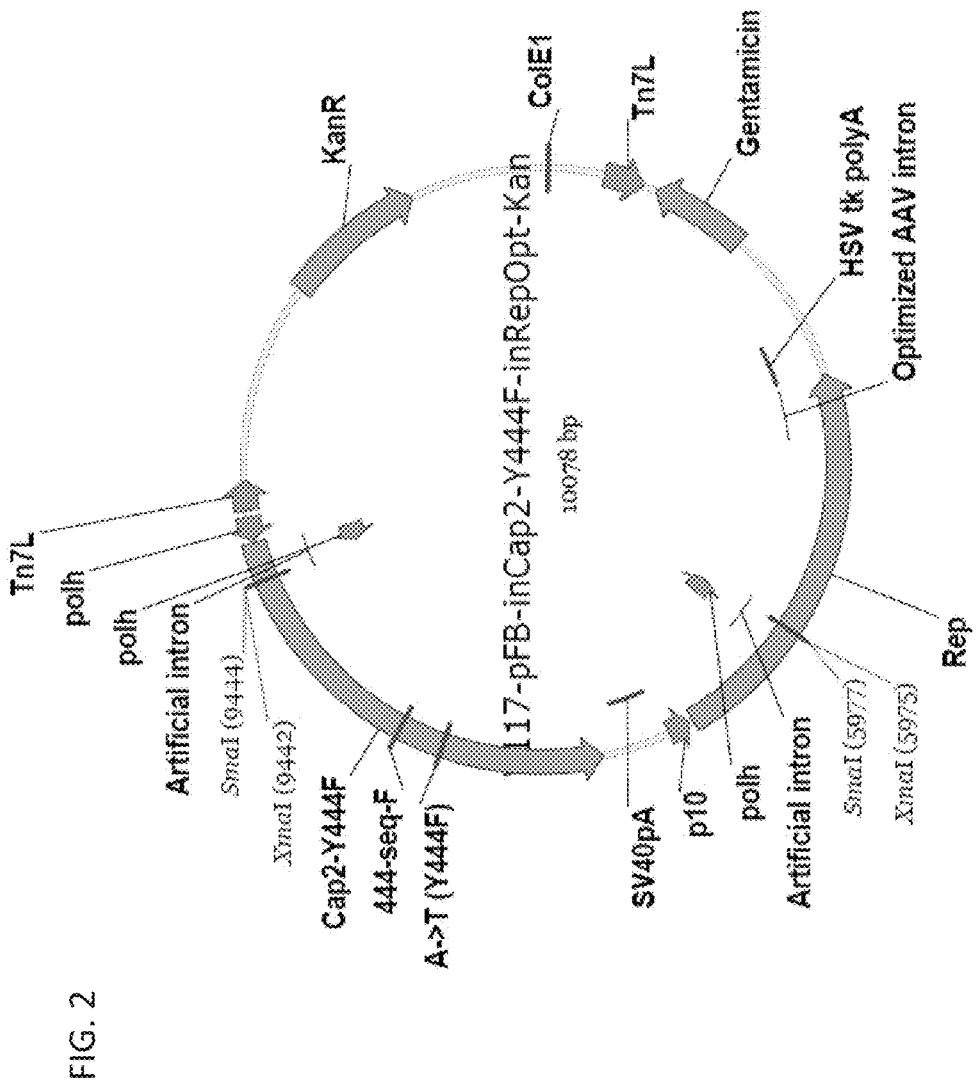
FIG. 2 shows a schematic diagram of an rAAV2 packaging vector, with a mutation in the viral capsid gene (Y444F).

Vectors of particular use for the present invention are shown in FIGS. 1 and 2. Modifications can be readily made by the skilled person in the art using standard DNA recombinant techniques.

The nucleic acid sequence of vector V-032-pFB-AAV-CMV-SV40pA (depicted in FIG. 1) is provided below in SEQ ID NO: 21:

```
gacgcgccctgtagcggcgcattaagcgcggcgggtgtggtggttacgcg
cagcgtgaccgctacacttgccagcgccctagcgcccgctcctttcgctt
tcttcccttcctttctcgccacgttcgccggctttccccgtcaagctcta
aatcggggctccctttagggttccgatttagtgctttacggcacctcga
ccccaaaaaacttgattagggtgatggttcacgtagtgggccatcgccct
gatagacggttttttcgcccttgacgttggagtccacgttctttaatagt
ggactcttgttccaaactggaacaacactcaaccctatctcggtctattc
ttttgatttataagggattttgccgatttcggcctattggttaaaaaatg
agctgatttaacaaaaatttaacgcgaattttaacaaaatattaacgttt
acaatttcaggtggcacttttcggggaaatgtgcgcggaacccctatttg
tttattttctaaatacattcaaatatgtatccgctcatgagacaataac
```

-continued cctgataaatgcttcaataatattgaaaaaggaagagtatgagtattcaa
catttccgtgtcgcccttattccctttttttgcgggcattttgccttcctgt
ttttgctcacccagaaacgctggtgaaagtaaaagatgctgaagatcagt
tgggtgcacgagtgggttacatcgaactggatctcaacagcggtaagatc
cttgagagttttcgccccgaagaacgttttccaatgatgagcacttttaa
agttctgctatgtggcgcggtattatcccgtattgacgccgggcaagagc
aactcggtcgccgcatacactattctcagaatgacttggttgagtactca
ccagtcacagaaaagcatcttacggatggcatgacagtaagagaattatg
cagtgctgccataaccatgagtgataacactgcggccaacttacttctga
caacgatcggaggaccgaaggagctaaccgctttttttgcacaacatgggg
gatcatgtaactcgccttgatcgttgggaaccggagctgaatgaagccat
accaaacgacgagcgtgacaccacgatgcctgtagcaatggcaacaacgt
tgcgcaaactattaactggcgaactacttactctagcttcccggcaacaa
ttaatagactggatggaggcggataaagttgcaggaccacttctgcgctc
ggcccttccggctggctggtttattgctgataaatctggagccggtgagc
gtgggtctcgcggtatcattgcagcactggggccagatggtaagccctcc
cgtatcgtagttatctacacgacggggagtcaggcaactatggatgaacg
aaatagacagatcgctgagataggtgcctcactgattaagcattggtaac
tgtcagaccaagtttactcatatatactttagattgatttaaaacttcat
ttttaatttaaaaggatctaggtgaagatcctttttgataatctcatgac
caaaatcccttaacgtgagttttcgttccactgagcgtcagaccccgtag
aaaagatcaaaggatcttcttgagatcctttttttctgcgcgtaatctgc
tgcttgcaaacaaaaaaaccaccgctaccagcggtggtttgtttgccgga
tcaagagctaccaactcttttccgaaggtaactggcttcagcagagcgc
agataccaaatactgtccttctagtgtagccgtagttaggccaccacttc
aagaactctgtagcaccgcctacatacctcgctctgctaatcctgttacc
agtggctgctgccagtggcgataagtcgtgtcttaccgggttggactcaa
gacgatagttaccggataaggcgcagcggtcgggctgaacggggggttcg
tgcacacagcccagcttggagcgaacgacctacaccgaactgagatacct
acagcgtgagcattgagaaagcgccacgcttcccgaagggagaaaggcgg
acaggtatccggtaagcggcagggtcggaacaggagagcgcacgagggag
cttccaggggaaacgcctggtatctttatagtcctgtcgggtttcgcca
cctctgacttgagcgtcgatttttgtgatgctcgtcaggggggcggagcc
tatggaaaaacgccagcaacgcggcctttttacggttcctggccttttgc
tggccttttgctcacatgttcttttcctgcgttatcccctgattctgtgga
taaccgtattaccgcctttgagtgagctgataccgctcgccgcagccgaa
cgaccgagcgcagcgagtcagtgagcgaggaagcggaagagcgcctgatg
cggtattttctccttacgcatctgtgcggtatttcacaccgcagaccagc
cgcgtaacctggcaaaatcggttacggttgagtaataaatggatgccctg
cgtaagcgggtgtgggcggacaataaagtcttaaactgaacaaaatagat
ctaaactatgacaataaagtcttaaactagacagaatagttgtaaactga -continued aatcagtccagttatgctgtgaaaaagcatactggacttttgttatggct
aaagcaaactcttcattttctgaagtgcaaattgcccgtcgtattaaaga
ggggcgtggccaagggcatggtaaagactatattcgcggcgttgtgacaa
tttaccgaacaactccgcggccgggaagccgatctcggcttgaacgaatt
gttaggtggcggtacttgggtcgatatcaaagtgcatcacttcttcccgt
atgcccaactttgtatagagagccactgcgggatcgtcaccgtaatctgc
ttgcacgtagatcacataagcaccaagcgcgttggcctcatgcttgagga
gattgatgagcgcggtggcaatgccctgcctccggtgctcgccggagact
gcgagatcatagatatagatctcactacgcggctgctcaaacctgggcag
aacgtaagccgcgagagcgccaacaaccgcttcttggtcgaaggcagcaa
gcgcgatgaatgtcttactacggagcaagttcccgaggtaatcggagtcc
ggctgatgttgggagtaggtggctacgtctccgaactcacgaccgaaaag
atcaagagcagcccgcatggatttgacttggtcagggccgagcctacatg
tgcgaatgatgcccatacttgagccacctaactttgttttagggcgactg
ccctgctgcgtaacatcgttgctgctgcgtaacatcgttgctgctccata
acatcaaacatcgacccacggcgtaacgcgcttgctgcttggatgcccga
ggcatagactgtacaaaaaaacagtcataacaagccatgaaaaccgccac
tgcgccgttaccaccgctgcgttcggtcaaggttctggaccagttgcgtg
agcgcatacgctacttgcattacagtttacgaaccgaacaggcttatgtc
aactgggttcgtgccttcatccgtttccacggtgtgcgtcacccggcaac
cttgggcagcagcgaagtcgaggcatttctgtcctggctggcgaacgagc
gcaaggtttcggtctccacgcatcgtcaggcattggcggccttgctgttc
ttctacggcaaggtgctgtgcacggatctgccctggcttcaggagatcgg
aagacctcggccgtcgcggcgcttgccggtggtgctgacccccgatgaag
tggttcgcatcctcggttttctggaaggcgagcatcgtttgttcgcccag
gactctagctatagttctagtggttggctacattattgaagcatttatca
gggttattgtctcagagcatgcctgcaggcagctgcgcgctcgctcgctc
actgaggccgcccgggcgtcgggcgacctttggtcgcccggcctcagtga
gcgagcgagcgcgcagagagggagtggccaactccatcactaggggttcc
tgcggccgcacgcgtgttactagttattaatagtaatcaattacggggtc
attagttcatagcccatatatggagttccgcgttacataacttacggtaa
atggcccgcctggctgaccgcccaacgacccccgcccattgacgtcaata
atgacgtatgttcccatagtaacgccaatagggactttccattgacgtca
atgggtggagtatttacggtaaactgcccacttggcagtacatcaagtgt
atcatatgccaagtacgccccctattgacgtcaatgacggtaaatggccc
gcctggcattatgcccagtacatgaccttatgggactttcctacttggca
gtacatctacgtattagtcatcgctattaccatggtgatgcggttttggc
agtacatcaatgggcgtggatagcggtttgactcacggggatttccaagt
ctccaccccattgacgtcaatgggagtttgttttggcaccaaaatcaacg
ggactttccaaaatgtcgtaacaactccgccccattgacgcaaatgggcg

```
gtaggcgtgtacggtgggaggtctatataagcagagctcgtttagtgaac
cgtcagatcgcctggagacgccatccacgctgttttgacctccatagaag
acaccgggaccgatccagcctccaaccggttcgaacaggtaagcgcccct
aaaatccctttggcacaatgtgtcctgaggggagaggcagcgacctgtag
atgggacggggcactaaccctcagggtttggggttctgaatgtgagtat
cgccatgtaagcccagtatttggccaatctcagaaagctcctggctccct
ggaggatggagagagaaaaacaaacagctcctggagcaggagagtgctg
gcctcttgctctccggctccctctgttgccctctggtttctccccaggtt
gaattcgatatcggatccatcgataccgtcgacctcgagggggggcccgg
tacccaattcgccctatagtgagtcgtattacgcgcgcagcggccgacca
tggcccaacttgtttattgcagcttataatggttacaaataaagcaatag
catcacaaatttcacaaataaagcatttttttcactgcattctagttgtg
gtttgtccaaactcatcaatgtatcttatcatgtctggatctccggacca
cgtgcggaccgagcggccgcaggaaccctagtgatggagttggccactc
cctctctgcgcgctcgctcgctcactgaggccgggcgaccaaaggtcgcc
cgacgcccgggctttgcccgggcggcctcagtgagcgagcgagcgcgcag
ctgcctgcaggaagctgtaagcttgtcgagaagtactagaggatcataat
cagccataccacatttgtagaggttttacttgctttaaaaaacctcccac
acctcccctgaacctgaaacataaaatgaatgcaattgttgttgttaac
ttgtttattgcagcttataatggttacaaataaagcaatagcatcacaaa
tttcacaaataaagcatttttttcactgcattctagttgtggtttgtcca
aactcatcaatgtatcttatcatgtctggatctgatcactgatatcgcct
aggagatccgaaccagataagtgaaatctagttccaaactattttgtcat
ttttaattttcgtattagcttacgacgctacacccagttcccatctatt
tgtcactcttccctaaataatccttaaaaactccattccacccctccca
gttcccaactattttgtccgcccacagcggggcattttcttcctgttat
gttttaatcaaacatcctgccaactccatgtgacaaaccgtcatcttcg
gctactttttctctgtcacagaatgaaaattttctgtcatctcttcgtt
attaatgtttgtaattgactgaatatcaacgcttatttgcagcctgaatg
gcgaatg
```

The nucleic acid sequence for the vector V117-pFB-inCap2-Y444F-inRepOpt-Kan (depicted in FIG. 2) is provided below in SEQ ID NO: 22:

```
ttctctgtcacagaatgaaaattttctgtcatctcttcgttattaatgt
ttgtaattgactgaatatcaacgcttatttgcagcctgaatggcgaatgg
gacgcgccctgtagcggcgcattaagcgcggcgggtgtggtggttacgcg
cagcgtgaccgctacacttgccagcgccctagcgcccgctcctttcgctt
tcttcccttcctttctcgccacgttcgccggctttccccgtcaagctcta
aatcggggctcccttaggttccgatttagtgctttacggcacctcga
ccccaaaaaacttgattagggtgatggttcacgtagtgggccatcgccct
gatagacggtttttcgccctttgacgttggagtccacgttctttaatagt
ggactcttgttccaaactggaacaacactcaaccctatctcggtctattc
ttttgatttataagggattttgccgatttcggcctattggttaaaaatg
agctgatttaacaaaaatttaacgcgaattttaacaaaatattaacgttt
acaatttcctgatgcggtattttctccttacgcatctgtgcggtatttca
caccgcatatggtgcactctcagtacaatctgctctgatgccgcatagtt
aagccagccccgacacccgccaacacccgctgacgcgccctgacgggctt
gtctgctcccggcatccgcttacagacaagctgtgaccgtctccgggagc
tgcatgtgtcagaggttttcaccgtcatcaccgaaacgcgcgagacgaaa
gggcctcgtgatacgcctatttttataggttaatgtcatgataataatgg
tttcttagacgtcaggtggcacttttcggggaaatgtgcgcggaacccct
atttgtttattttctaaatacattcaaatatgtatccgctcatgagaca
ataaccctgataaatgcttcaataatattgaaaaaggaagagtatgattg
aacaagatggattgcacgcaggttctccggccgcttgggtggagaggcta
ttcggctatgactgggcacaacagacaatcggctgctctgatgccgccgt
gttccggctgtcagcgcaggggcgcccggttcttttttgtcaagaccgacc
tgtccggtgccctgaatgaactgcaggacgaggcagcgcggctatcgtgg
ctggccacgacgggcgttccttgcgcagctgtgctcgacgttgtcactga
agcgggaagggactggctgctattgggcgaagtgccggggcaggatctcc
tgtcatctcaccttgctcctgccgagaaagtatccatcatggctgatgca
atgcggcggctgcatacgcttgatccggctacctgcccattcgaccacca
agcgaaacatcgcatcgagcgagcacgtactcggatggaagccggtcttg
tcgatcaggatgatctggacgaagagcatcaggggctcgcgccagccgaa
ctgttcgccaggctcaaggcgcgcatgcccgacggcgaggatctcgtcgt
gacccatggcgatgcctgcttgccgaatatcatggtggaaaatggccgct
tttctggattcatcgactgtggccggctgggtgtggcggaccgctatcag
gacatagcgttggctacccgtgatattgctgaagagcttggcggcgaatg
ggctgaccgcttcctcgtgctttacggtatcgccgctcccgattcgcagc
gcatcgccttctatcgccttcttgacgagttcttctgagtaaccgtcaga
ccaagtttactcatatatactttagattgatttaaaacttcatttttaat
ttaaaaggatctaggtgaagatcctttttgataatctcatgaccaaaatc
ccttaacgtgagttttcgttccactgagcgtcagaccccgtagaaaagat
caaaggatcttcttgagatcctttttttctgcgcgtaatctgctgcttgc
aaacaaaaaaaccaccgctaccagcggtggtttgtttgccggatcaagag
ctaccaactctttttccgaaggtaactggcttcagcagagcgcagatacc
aaatactgtccttctagtgtagccgtagttaggccaccacttcaagaact
ctgtagcaccgcctacatacctcgctctgctaatcctgttaccagtggct
gctgccagtggcgataagtcgtgtcttaccgggttggactcaagacgata
gttaccggataaggcgcagcggtcgggctgaacggggggttcgtgcacac
agcccagcttggagcgaacgacctacaccgaactgagatacctacagcgt
gagcattgagaaagcgccacgcttcccgaagggagaaaggcggacaggta
```

-continued

```
tccggtaagcggcagggtcggaacaggagagcgcacgagggagcttccag
ggggaaacgcctggtatctttatagtcctgtcgggtttcgccacctctga
cttgagcgtcgattttttgtgatgctcgtcagggggcggagcctatggaa
aaacgccagcaacgcggcctttttacggttcctggccttttgctggcctt
ttgctcacatgttctttcctgcgttatccctgattctgtggataaccgt
attaccgcctttgagtgagctgataccgctcgccgcagccgaacgaccga
gcgcagcgagtcagtgagcgaggaagcggaagagcgcctgatgcggtatt
ttctccttacgcatctgtgcggtatttcacaccgcagaccagccgcgtaa
cctggcaaaatcggttacggttgagtaataaatggatgccctgcgtaagc
gggtgtgggcggacaataaagtcttaaactgaacaaaatagatctaaact
atgacaataaagtcttaaactagacagaatagttgtaaactgaaatcagt
ccagttatgctgtgaaaaagcatactggactttgtatggctaaagcaa
actcttcattttctgaagtgcaaattgcccgtcgtattaaagaggggcgt
ggccaagggcatggtaaagactatattcgcggcgttgtgacaatttaccg
aacaactccgcggccgggaagccgatctcggcttgaacgaattgttaggt
ggcggtacttgggtcgatatcaaagtgcatcacttcttcccgtatgccca
actttgtatagagagccactgcgggatcgtcaccgtaatctgcttgcacg
tagatcacataagcaccaagcgcgttggcctcatgcttgaggagattgat
gagcgcggtggcaatgccctgcctccggtgctcgccggagactgcgagat
catagatatagatctcactacgcggctgctcaaacctgggcagaacgtaa
gccgcgagagcgccaacaaccgcttcttggtcgaaggcagcaagcgcgat
gaatgtcttactacggagcaagttccgaggtaatcggagtccggctgat
gttgggagtaggtggctacgtctccgaactcacgaccgaaaagatcaaga
gcagcccgcatggatttgacttggtcagggccgagcctacatgtgcgaat
gatgcccatacttgagccacctaactttgttttagggcgactgccctgct
gcgtaacatcgttgctgctgcgtaacatcgttgctgctccataacatcaa
acatcgacccacggcgtaacgcgcttgctgcttggatgcccgaggcatag
actgtacaaaaaacagtcataacaagccatgaaaaccgccactgcgccg
ttaccaccgctgcgttcggtcaaggttctggaccagttgcgtgagcgcat
acgctacttgcattacagtttacgaaccgaacaggcttatgtcaactggg
ttcgtgccttcatccgtttccacggtgtgcgtcaccggcaaccttgggc
agcagcgaagtcgaggcatttctgtcctggctggcgaacgagcgcaaggt
ttcggtctccacgcatcgtcaggcattggcggccttgctgttcttctacg
gcaaggtgctgtgcacggatctgccctggcttcaggagatcggtagacct
cggccgtcgcgcgcttgccggtggtgctgacccccggatgaagtggttcg
catcctcggttttctggaaggcgagcatcgttgttcgcccaggactcta
gctatagttctagtggttggcctacgtacccgtagtggctatggcagggc
ttgccgccccgacgttggctgcgagccctgggccttcacccgaacttggg
ggttgggtggggaaaggaagaaacgcgggcgtattggtcccaatgggg
tctcggtggggtatcgacagagtgccagccctgggaccgaaccccgcgtt
tatgaacaaacgacccaacacccgtgcgttttattctgtctttttattgc
cgtcatagcgcgggttccttccggtattgtctccttccgtgtttcagtta
gcctcccccatctcccggtaccgcatgctccttcagagagagtgtcctcg
agccaatctgaaacaataccatcggcagccatacctgatttaaatcattt
attgttcaaagatgcagtcatccaaatccacattgaccagatcgcaggca
gtgcaagcgtctggcacctttcccatgatatgatgaatgtagcacagttt
ctgatacgccttttgacgacagaaacgggttgagattctgacacgggaa
agcactctaaacagtctttctgtccgtgagtgaagcagatatttgaattc
tgattcattctctcgcattgtctgcagggaaacagcatcagattcatgcc
cacgtgacgagaacatttgttttggtacctgtctgcgtagttgatcgaag
cttccgcgtctgacgtcgatggctgcgcaactgactcgcgcacccgtttg
ggctcacttatatctgcgtcactggggcgggtcttttcttggctccacc
cttttttgacgtagaattcatgctccacctcaaccacgtgatcctttgccc
accggaaaaagtctttgacttcctgcttggtgaccttcccaaagtcatga
tccagacgcgggtgagttcaaatttgaacatccggtcttgcaacggctg
ctggtgttcgaaggtcgttgagttcccgtcaatcacggcgcacatgttgg
tgttggaggtgacgatcacggagtcgggtctatctgggccgaggacttg
catttctggtccacgcgcaccttgcttcctccgagaatggctttggccga
ctccacgaccttggcggtcatcttcccctcctcccaccagatcaccatct
tgtcgacacagtcgttgaagggaaagttctcattggtccagtttacgcac
ccgtagaagggcacagtgtgggctatggcctccgcgatgttggtcttccc
ggtagttgcaggcccaaacagccagatggtgttcctcttgccgaacttt
tcgtggcccatcccagaaagacggaagccgcatattgggatcgtacccg
tttagttccaaaatttttataaatccgattgctggaaatgtcctccacggg
ctgctggcccaccaggtagtcggggcggttttagtcaggctcataatct
ttcccgcattgtccaaggcagccttgatttgggaccgcgagttggaggcc
gcattgaaggagatgtatgaggcctggtcctcctggatccactgcttctc
cgaggtaatccccttgtccacgagccacccgaccagctccatgtacctgg
ctgaagttttttgatctgatcaccggcgcatcagaattgggattctgattc
tctttgttctgctcctgcgtctgcgacacgtgcgtcagatgctgcgccac
caaccgtttacgctccgtgagattcaaacaggcgctgaaacaataggaag
ggagtggatgtcagtgtgtgctgcccggggggctctgactacaggtctccc
ccttcgcgcccgatggtgggacggtatgaataatccggaatatttatagg
ttttttttattacaaaactgttacgaaaacagtaaaatacttattatttg
cgagatggttatcatttttaattatctccatgatagatctctatcactgat
agggagtacttaccttaaatactgttccatattagtccacgcccactgga
gctcaggctgggttttggggagcaagtaattggggatgtagcactcatcc
accaccttgttcccgcctccggcgccatttctggtctttgtgaccgcgaa
ccagtttggcaaagtcggctcgatcccgcggtaaattctctgaatcagtt
tttcgcgaatctgactcaggaaacgtcccaaaaccatggatttcaccccg
gtggtttccacgagcacgtgcatgtggaagtagctctctcccttctcaaa
``` ttgcacaaagaaaagggcctccggggccttactcacacggcgccattccg
tcagaaagtcgcgctgcagcttctcggccacggtcagggtgcctgctca
atcagattcagatccatgtcagaatctggcggcaactcccattccttctc
ggccacccagttcacaaagctgtcagaaatgccgggcagatgctcgtcaa
ggtcgctggggaccttaatcacaatctcgtaaaacccggcatggcgggt
agggtgatcaagtcttcgtcgagtgattgtaaataaaatgtaatttacag
tatagtattttaattaatatacaaatgatttgataataattcttatttaa
ctataatatattgtgttgggttgaattaaaggtccgtagctttcgaatct
aggctcaagcagtgatcagatccagacatgataagatacattgatgagtt
tggacaaaccacaactagaatgcagtgaaaaaaatgctttatttgtgaaa
tttgtgatgctattgctttatttgtaaccattataagctgcaataaacaa
gttaacaacaacaattgcattcattttatgtttcaggttcaggggaggt
gtgggaggttttttaaagcaagtaaaacctctacaaatgtggtatggctg
attatgatcctctagtacttctcgacaagctgtagccatggaaactagat
aagaaagaaatacgcagagaccaaagttcaactgaaacgaattaaacggt
ttattgattaacaagcaattacagattacgagtcaggtatctggtgccaa
tggggcgaggctctgaatacacgccattagtgtccacagtaaagtccaca
ttaacagacttgttgtagttggaagtgtactgaatttcgggattccagcg
tttgctgttttccttctgcagctcccactcgatctccacgctgacctgtc
ccgtggagtactgtgtgatgaaggaagcaaactttgccgcactgaaggtg
gtcgaaggattcgcaggtaccggggtgttcttgatgagaatctgtggagg
agggtgtttaagtccgaatccacccatgaggggagagggtgaaaatgtc
cgtccgtgtgtggaatcttgcccagatgggcccctgaaggtacacatct
ctgtcctgccagaccatgcctggaagaacgccttgtgtgttgacatctgc
ggtagctgcttgtctgttgcctctctggaggttggtagatacagaaccat
actgctccgtagccacgggattggttgtcctgatttcctcttcgtctgta
atcatgaccttttcaatgtccacatttgttttctctgagccttgcttccc
aaagatgagaacccgctctgaggaaaaaacttttcttcatcgtccttgt
ggcttgccatggccgggccggattcaccagagagtctctgccattgagg
tggtacttggtagctccagtccacgagtattcactgttgttgttatccgc
agatgtctttgatactcgctgctggcggtaacagggtccaggaagccagt
tcctagactggtcccgaatgtcactcgctccggcctgagaaaactgaagc
cttgactgcgtggtggttccacttggagtgtttgttctgcttaagaaata
caggtactggtcgatgagaggattcatgagacggtccagactctggctgt
gagcgtagctgctgtggaaaggaacgtcctcaaaagtgtagctgaaggta
aagttgtttccggtacgcagcatctgagaaggaaagtactccaggcagta
aaatgaagagcgtcctactgcctgactcccgttgttcagggtgaggtatc
catactgtggcaccatgaagacgtctgctgggaacggcgggaggcatcct
tgatgcgccgagccgaggacgtacgggagctggtactccgagtcagtaaa
cacctgaaccgtgctggtaaggttattggcaatcgtcgtcgtaccgtcat
tctgcgtgacctctttgacttgaatgttaaagagcttgaagttgagtctc ttgggtcggaatcccagttgttgttgatgagtctttgccagtcacgtgg
tgaaaagtggcagtggaatctgttgaagtcaaaataccccaaggggtgc
tgtagccaaagtagtgattgtcgttcgaggctcctgattggctggaaatt
tgtttgtagaggtggttgttgtaggtgggcagggcccaggttcgggtgct
ggtggtgatgactctgtcgcccatccatgtggaatcgcaatgccaatttc
ccgaggaattacccactccgtcggcgccctcgttattgtctgccattggt
gcgccactgcctgtagccatcgtattagttcccagaccagaggggctgc
tggtggctgtccgagaggctgggggtcaggtactgagtctgcgtctccag
tctgaccaaaattcaatcttttcttgcaggctgctggcccgcctttccg
gttcccgaggaggagtctggctccacaggagagtgctctaccggcctctt
ttttcccggagccgtcttaacaggttcctcaaccaggcccagaggttcaa
gaaccctcttttcgcctggaagactgctcgtccgaggttgcccccaaaa
gacgtatcttcttaaggcgctcctgaaactccgcgtcggcgtggttgta
cttgaggtacgggttgtctccgctgtcgagctgccggtcgtaggctttgt
cgtgctcgagggccgcggcgtctgcctcgttgaccggctctcccttgtcg
agtccgttgaagggtccgaggtacttgtacccaggaagcacaagacccct
gctgtcgtccttatgccgctctgcgggctttggtggtggtgggccaggtt
tgagcttccaccactgtcttattccttcagagagagtgtcctcgagccaa
tctgaaacaataggaagggagtggatgtcagtgtgtgctgcccggggct
ctgactacaggtctccccccttcgcgcccgatggtgggacggtatgaataa
tccggaatatttataggttttttttattacaaaactgttacgaaaacagta
aaatacttatttatttgcgagatggttatcattttaattatctccatgat
agatctctatcactgatagggagtacttacctggaagataaccatcggca
gccatcttaacaggatccgcgcccgatggtgggacggtatgaataatccg
gaatatttataggttttttttattacaaaactgttacgaaaacagtaaaat
acttatttatttgcgagatggttatcattttaattatctccatgatctat
taatattccggagtatacctaggagatccgaaccagataagtgaaatcta
gttccaaactattttgtcatttttaatttttcgtattagcttacgacgcta
cacccagttcccatctatttttgtcactcttccctaaataatccttaaaaa
ctccatttccacccctcccagttcccaactattttgtccgcccacagcgg
ggcattttcttcctgttatgttttaatcaaacatcctgccaactccat
gtgacaaaccgtcatcttcggctacttt Any of a variety of other vectors adapted for expression of any light-sensitive protein in a cell of the eye, particularly within a retinal cell, more particularly within a non photoreceptor cell (e.g. amacrine cells, retinal ganglion cells, retinal bipolar cells, (ON or OFF cone retinal bipolar cells; rod bipolar cells)), are within the scope of the present invention. Gene delivery vectors can be viral (e.g., derived from or containing sequences of viral DNA or RNA, preferably packaged within a viral particle), or non-viral (e.g., not packaged within a viral particle, including "naked" polynucleotides, nucleic acid associated with a carrier particle such as a liposome or targeting molecule, and the like).

Therapeutic Uses

The advantages of using gene regulatory elements, such as those encompassed by the present invention, that direct the expression to a specific subset of retinal eyes is to accurately recapitulate the visual processing signals from the ON and OFF pathways to improve or restore photosensitivity, and thereby improving or restoring vision.

Visual information is processed through the retina through two pathways: an ON pathway which signals the light ON, and an OFF pathway which signals the light OFF. The existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells are hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cells) to ON or OFF cone bipolar cells.

Accordingly, a dual rhodopsin system can be used to recapitulate the ON and OFF pathways integral to visual processing and acuity. Briefly, a ChR2 or Chop2 protein can be specifically targeted to ON type retinal neurons (e.g., ON type ganglion cells and/or ON type bipolar cells), while a hypopolarizing light sensor (e.g., halorhodopsin or other chloride pump or proton pump, preferably Arch, ArchT, Jaws known in the art, as well as variants known in the art or yet to be identified) can be targeted to OFF type retinal neurons (e.g. OFF type ganglion cells and/or OFF type bipolar cells) to create ON and OFF pathways. An alternative approach to restore ON and OFF pathways in the retina is achieved by, expressing a depolarizing light sensor, such as ChR2, to rod bipolar cells or AII amacrine. In this approach, the depolarization of rod bipolar cells or AII amacrine cells can lead to the ON and OFF responses at the levels of cone bipolar cells and the downstream retinal ganglion cells. Thus, the ON and OFF pathways that are inherent in the retina are restored or maintained.

The present invention can be used in methods for increasing photosensitivity, increasing phototransduction, increasing visual evoked potential (VEP), or improving or restoring vision. Tests are known in the art for quantifying photosensitivity and visual evoked potential, including electroretinography (ERG) analysis. Visual and behavior tests can be utilized to determine improvements or restoration of vision. Behavior tests include maze tests and the swimming test. Visual tests, such as the Snellen chart and visual field testing, are utilized to determine improved or restored vision. Such tests can be readily performed by a clinical practitioner. As used herein, "increasing" is meant in reference to before treatment or in comparison to one that has not undergone treatment, e.g., ocular gene therapy.

The present invention can be formulated to a pharmaceutical composition or medicament suitable for administration into a subject or patient. Suitable routes of administration include, for example, intravitreal, intraocular, or subretinal injection. Preferably, the route of administration is by intravitreal injection. All retinal neurons, including retinal ganglion cells, bipolar cells, horizontal cells, amacrine cells, and photoreceptor cells are known to be reasonably well-accessible to intravitreal injection as disclosed herein. Intravitreal and/or subretinal injection can provide the necessary access to the bipolar cells, especially in circumstances in which the photoreceptor cell layer is absent due to degeneration.

Such formulations comprise a pharmaceutically and/or physiologically acceptable vehicle, diluent, carrier, or excipient, such as buffered saline or other buffers, e.g., HEPES, to maintain physiologic pH. For a discussion of such components and their formulation, see, generally, Gennaro, A. E., Remington: The Science and Practice of Pharmacy, Lippincott Williams & Wilkins Publishers; 2003 or latest edition). See also, WO00/15822. If the preparation is to be stored for long periods, it may be frozen, for example, in the presence of glycerol.

In one embodiment, the constructs or nucleic acid expression vectors described herein are packaged in adenoviral vectors for transgene delivery. An effective amount of rAAV virions carrying a transgene under the control of the modified mGluR6 promoter is preferably in the range of between about $10^{10}$ to about $10^{13}$ rAAV infectious units in a volume of between about 150 and about 800 μl per injection. The rAAV infectious units can be measured according to McLaughlin, S K et al., 1988, *J. Viral.* 62:1963. More preferably, the effective amount is between about $10^{10}$ and about $10^{12}$ rAAV infectious units and the injection volume is preferably between about 250 and about 500 μl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid(s) or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Ocular Disorders

The term treatment includes, but is not limited to, arresting, inhibiting, or reversing the progression of an ocular disease or disorder. Preferred indicators of successful treatment are the preservation of existing vision or improvement of vision compared to vision before treatment.

The ocular disorders for which the present nucleic acids and vectors, are intended and may be used to improve one or more parameters of vision include, but are not limited to, developmental abnormalities that affect both anterior and posterior segments of the eye. Anterior segment disorders include glaucoma, cataracts, corneal dystrophy, and keratoconus. Posterior segment disorders include blinding disorders caused by photoreceptor malfunction and/or death caused by retinal dystrophies and degenerations.

A nonlimiting list of ocular diseases that may benefit from the methods described herein include, but are not limited to, retinoblastoma, ocular melanoma, diabetic retinopathy, hypertensive retinopathy, any inflammation of the ocular tissues (i.e., chorioretinal inflammation, scleritis, keratitis, uveitis, etc.), or infection (i.e., bacterial or viral). Angiogenesis-related eye diseases include, but are not limited to age-related macular degeneration, diabetic retinopathy, corneal neovascularizing diseases, retinal angiomatous proliferation, polypoidal choroidal vasculopathy, ischemia-induced neovascularizing retinopathy, extreme or high myopia, and retinopathy of prematurity.

Retinal disorders include congenital stationary night blindness, macular degeneration, age-related macular degeneration, congenital cone dystrophies, and a large group of retinitis-pigmentosa (RP)-related disorders. These disorders include genetically pre-disposed death of photoreceptor cells—rods and cones in the retina—occurring at various ages. Among those are severe retinopathies, such as subtypes of RP itself that progresses with age and causes blindness in childhood and early adulthood and RP-associated diseases, such as genetic subtypes of Leber's congenital amaurosis (LCA), which frequently results in loss of vision during childhood, as early as the first year of life. The latter disorders are generally characterized by severe reduction, and often complete loss of photoreceptor cells, rods and cones. (Trabulsi, E I, ed., *Genetic Diseases of the Eye*, Oxford University Press, N Y, 1998).

Ocular neovascularization is a widespread cause of vision loss that may also be treated using the optimized enhancers, promoters, and vectors of the present invention. It can occur in a number of proliferative retinal diseases including, but not limited to, diabetic retinopathy, dry (atrophic) and wet (neovascular or exudative) age-related macular degeneration (AMD), retinal artery or vein occlusion, glaucoma, and other inherited retinal degenerations, uveitis, retinal detachment, and eye cancers (ocular melanoma and retinoblastoma), and retinopathy of prematurity (ROP).

In particular, the optimized enhancers, promoters, and vectors of the present invention useful for expressing transgenes for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by the transgenes expressed by the nucleic acids and vectors of the present invention.

Thus, the particular ocular disorder treated by the present invention may include the above-mentioned disorders and a number of diseases which have yet to be so characterized.

EXAMPLES

Example 1: Generation of Optimized mGluR6 Promoter Constructs

A series of AAV2 expression cassettes were constructed with the combination of sequences of the mGluR6 promoter, the 200 bp mGluR6 enhancer, and intron sequences of the mGluR6 gene, carrying a transgene. The transgene was either reporter mCherry or GFP-fused channelrhodopsin-2 (GFP-ChR2), ChR2 alone.

Two optimized mGluR6 promoter constructs are shown in FIG. 3 (I4) and FIG. 4 (I1a) for driving expression of a transgene. The transgene is, for example, a reporter gene, mCherry. The I4 construct comprises an optimized promoter with the 200 bp mGluR6 enhancer sequence located upstream of a 500 bp fragment of the mGluR6 promoter. The I1a construct comprises an optimized promoter with intron 4 of the mGluR6 gene located upstream of intron 3 of the mGluR6 gene, intron 3 of the mGluR6 gene located upstream of the 200 bp mGluR6 enhancer sequence, and the mGluR6 enhancer sequence located upstream of a 500 bp fragment of the mGluR6 promoter.

AAV2 serotype 2 vectors with an Y444F capsid mutation were packaged and affinity purified at Virovek (Hayward, Calif.).

Example 2: In Vivo Expression in the Retina

Recombinant AAV-mediated expression of a transgene by the two optimized mGluR6 promoters shown in FIGS. 3 and 4 were tested in mice.

Briefly, 1-month-old C57BL/6J mice were anesthetized by intraperitoneal injection of a mixture of 120 mg/kg ketamine and 15 mg/kg xylazine. Under a dissecting microscope, a small perforation was made in the temporal sclera region with a needle. A total of 1 µl viral vector solution at the concentration of $1 \times 10^{13}$ vg/ml was injected into the intravitreal space through the hole with a Hamilton syringe. One month after the injection, the mice were killed to examine the expression patterns of transgene.

Retinal whole-mounts or vertical sections were blocked for 1 h in a solution containing 5% Chemiblocker (membrane-blocking agent; Chemicon, Brica, Mass., USA), 0.5% Triton X-100 and 0.05% sodium azide (Sigma). The primary antibodies were diluted in the same solution and applied overnight, followed by incubation (1 h) in the secondary antibodies, which were conjugated to Alexa 594 (1:600, red fluorescence, Molecular Probes), Alexa 488 (1:600, green fluorescence, Molecular Probes). The following antibodies were used in this study: rabbit anti-mCherry (1:500, 632496, Clontech); rabbit anti-PKC (1:20000, 2056, Cell Signal).

All images were made using a Zeiss Axioplan 2 microscope with the Apotome oscillating grating to reduce out-of-focus stray light. Z-stack images were captured and image projections were made by collapsing individual z-stacks of optical sections into a single plane. To create the merged images for double labeling, the red and green or blue channels for each individual optical section were combined and the merged z-optical sections were collapsed into a single plane. The brightness and contrast were adjusted using Adobe Photoshop C54.

Figure 5:
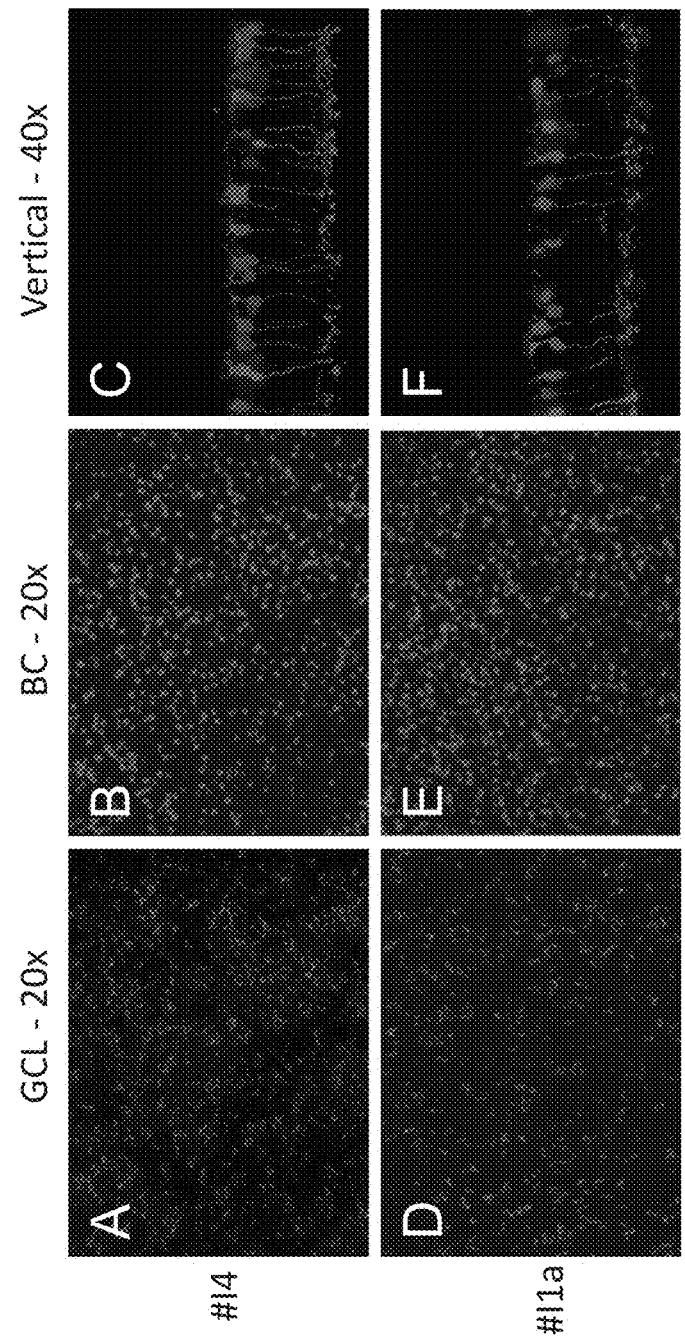
FIG. 5A-F is a series of immunofluorescence images demonstrating rAAV-mediated expression of transgene (mCherry) by two optimized mGluR6 promoter constructs (I4 and I1a). (A, D) Images were taken at the ganglion cell layer in retinal whole-mounts to visualize the axon terminals of rod bipolar cells. (B, E) Images were taken in inner nuclear layer in retinal whole-mounts to visualize the somas of rod bipolar cells. (C, F) The expression of transgene (mCherry) in rod bipolar cells is depicted in retinal vertical sections.

Retinal whole mounts from mice injected with I4 and I1a-containing virions are shown in FIG. 5. The mCherry expression at the axon terminals of bipolar cells was detected in the ganglion cell layer (FIGS. 5A and 5D), as well as the expression at the bipolar cell bodies in the inner nuclear layer (FIGS. 5B and 5D). FIGS. 5C and 5F demonstrate the mCherry staining viewed from retinal vertical sections. Thus, FIG. 5 shows that both optimized mGluR6 promoter constructs efficiently and selectively expressed the transgene in bipolar cells in the retinas of mice. Furthermore, the expression level of I1a was shown to be two to three times higher than that of I4.

Example 3: Transgene Expression Targeting

Figure 6:
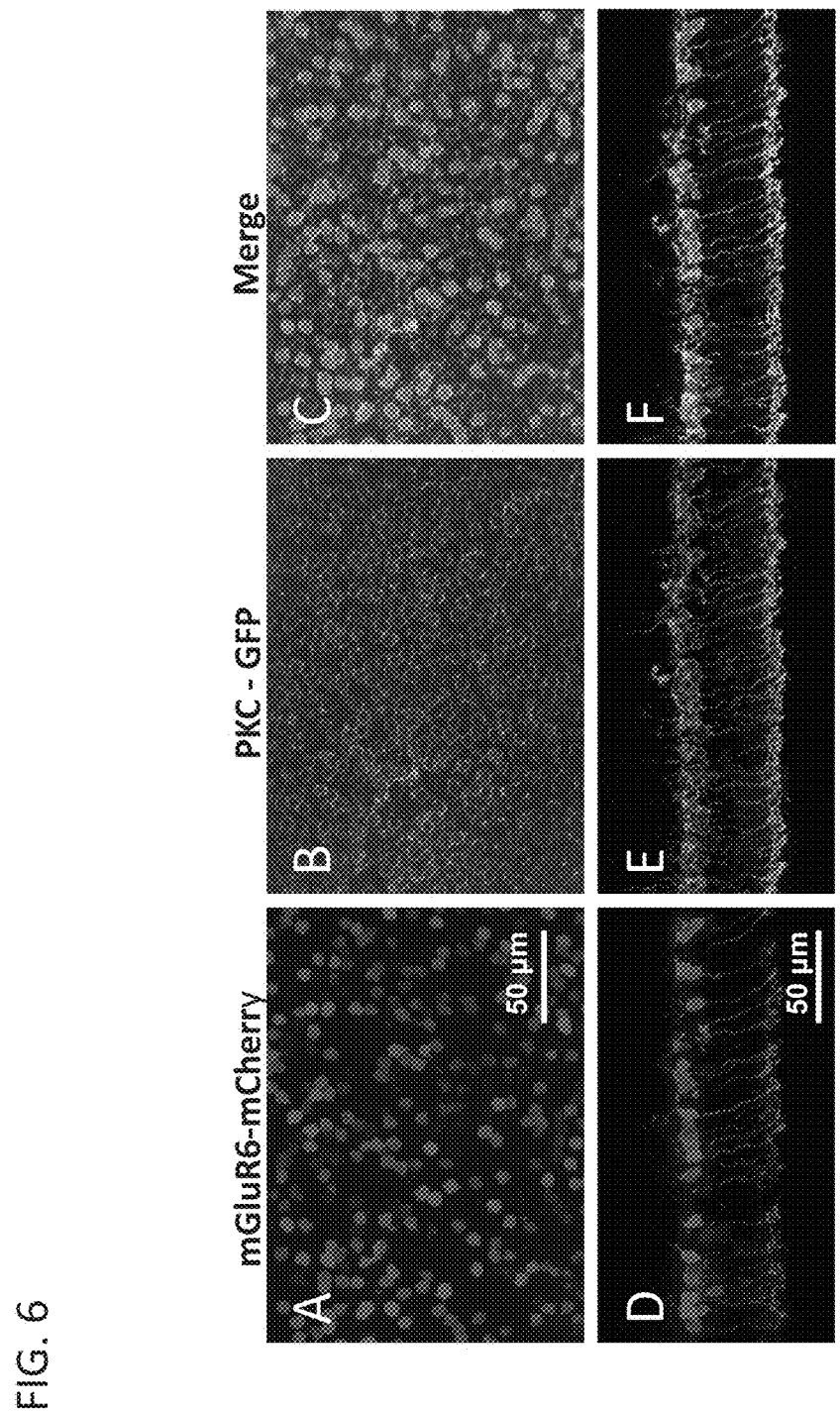
FIG. 6A-F is a series of immunofluorescence images demonstrating the expression of a transgene targeted to rod bipolar cells. The rAAV2/2 (Y444F)-mediated expression of mCherry driven by an optimized mChluR6 promoter is depicted in retinal whole-mount (A) and in retinal vertical section (D). Co-staining mCherry with anti-PKC (a rod bipolar cell marker) is also shown in retinal whole-mounts (A-C) and vertical sections (D-F).

Further immunostaining analysis demonstrated the targeting of transgene expression by the optimized mGluR6 promoters. Specifically, the retinal whole-mount sections obtained as described in Example 2 were co-stained with anti-PKC. PKC is a rod bipolar cell marker. mCherry and PKC staining in the retinal whole mount are shown in FIGS. 6A and 6B, respectively, while staining in vertical sections are shown in FIGS. 6D and 6E, respectively. The merged images in FIGS. 6C and 6F show that co-labeling between the mGluR6-driven mCherry-expressing cells and the PKC-expressing cells in up to 58% of the rod bipolar cells. These results indicate that the optimized mGluR6 is able to target transgene expression to rod bipolar cells after intravitreal injection.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts, and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated nucleic acid molecule comprising
   a. an mGluR6 enhancer or a variant thereof at least 70% identical to SEQ ID NO: 1 or SEQ ID NO: 2;
   b. an mGluR6 promoter or a variant thereof at least 70% identical to SEQ ID NO: 3, SEQ ID NO: 4, SEQ ID NO: 5, or SEQ ID NO: 6;
   c. an intron 4 of the mGluR6 gene or a variant thereof at least 70% identical to SEQ ID NO: 7 or SEQ ID NO. 8; and
   d. an intron 3 of the mGluR6 gene or a variant thereof at least 70% identical to SEQ ID NO: 9 or SEQ ID NO. 10.

2. The isolated nucleic acid molecule of claim 1, wherein said mGluR6 enhancer comprises the nucleic acid sequence of SEQ ID NO: 1 or SEQ ID NO: 2, wherein said mGluR6 promoter comprises the nucleic acid sequence of SEQ ID NO: 3, SEQ ID NO: 4, SEQ ID NO: 5, or SEQ ID NO: 6, wherein said intron 4 of the mGluR6 gene comprises the nucleic acid sequence of SEQ ID NO: 7 or SEQ ID NO: 8, and wherein said intron 3 of the mGluR6 gene comprises the nucleic acid sequence of SEQ ID NO: 9 or SEQ ID NO: 10.

3. The isolated nucleic acid molecule of claim 1, wherein the intron 4 of the mGluR6 gene is upstream of the intron 3 of the mGluR6 gene, wherein the intron 3 of the mGluR6 gene is upstream of the mGluR6 enhancer, and wherein the mGluR6 enhancer is upstream of the mGluR6 promoter.

4. A nucleic acid expression vector comprising the nucleic acid molecule of claim 1 operably linked to at least one transgene.

5. The nucleic acid expression vector of claim 4, wherein said mGluR6 enhancer comprises the nucleic acid sequence of SEQ ID NO: 1 or SEQ ID NO: 2, wherein said mGluR6 promoter comprises the nucleic acid sequence of SEQ ID NO: 3, SEQ ID NO: 4, SEQ ID NO: 5, or SEQ ID NO: 6, wherein said intron 4 of the mGluR6 gene comprises the nucleic acid sequence of SEQ ID NO: 7 or SEQ ID NO: 8, and wherein said intron 3 of the mGluR6 gene comprises the nucleic acid sequence of SEQ ID NO: 9 or SEQ ID NO: 10.

6. The nucleic acid expression vector of claim 4, wherein the intron 4 of the mGluR6 gene is upstream of the intron 3 of the mGluR6 gene, wherein the intron 3 of the mGluR6 gene is upstream of the mGluR6 enhancer, and wherein the mGluR6 enhancer is upstream of the mGluR6 promoter.

7. The nucleic acid expression vector of claim 4, wherein the vector is an adeno-associated virus vector or a recombinant adeno-associated virus (rAAV) vector.

8. The nucleic acid expression vector of claim 7, wherein the vector is a recombinant AAV1, AAV2, AAV3, AAV4, AAV5, AAV6, AAV7, AAV8, AAV9, AAV10, AAV11, or AAV12 vector.

9. The nucleic acid expression vector of claim 4, wherein the vector comprises a capsid protein comprising at least one mutation.

10. The nucleic acid expression vector of claim 9, wherein said at least one mutation is selected from the group consisting of:
    a tyrosine (Y) to phenylalanine (F) at amino acid position 444;
    a tyrosine (Y) to phenylalanine (F) at amino acid position 730;
    a tyrosine (Y) to phenylalanine (F) at amino acid positions 272, 444, 500, and 730;
    a threonine (T) to valine (V) at amino acid position 491; and
    a tyrosine (Y) to phenylalanine (F) at amino acid positions 272, 444, 500, 730, and a threonine (T) to valine (V) at amino acid position 491,
    wherein the amino acid positions correspond to amino acid positions of the AAV capsid protein.

11. The nucleic acid expression vector of claim 9, wherein the capsid protein comprises a peptide insert selected from the group consisting of SEQ ID NO: 35, SEQ ID NO: 36, and SEQ ID NO: 37.

12. The nucleic acid expression vector of claim 4, wherein the transgene is an opsin gene.

13. The nucleic acid expression vector of claim 12, wherein said opsin gene is selected from the group consisting of channelrhodopsin, melanopsin, pineal opsin, photopsins, halorhodopsin, bacteriorhodopsin and proteorhodopsin.

14. The nucleic acid expression vector of claim 4, wherein the transgene encodes a gene product that increases light sensitivity, increases light detection, increases photosensitivity, increases visual evoked potential, or restores vision in a retina.

15. A pharmaceutical composition comprising the nucleic acid expression vector of claim 4 and a pharmaceutically acceptable excipient.

16. A method for expressing a transgene in the eye comprising introducing into the eye the nucleic acid expression vector of any one of claims 4-14.

17. A method for expressing a transgene in the eye comprising introducing into the eye the pharmaceutical composition of claim 15.

* * * * *